US010858445B2

(12) United States Patent
Duby

(10) Patent No.: US 10,858,445 B2
(45) Date of Patent: Dec. 8, 2020

(54) METHODS OF TREATING TTP WITH IMMUNOGLOBULIN SINGLE VARIABLE DOMAINS AND USES THEREOF

(71) Applicant: Ablynx N.V., Zwijnaarde (BE)

(72) Inventor: Christian Duby, Brussels (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 510 days.

(21) Appl. No.: 15/319,467

(22) PCT Filed: Jun. 16, 2015

(86) PCT No.: PCT/EP2015/063493
§ 371 (c)(1),
(2) Date: Dec. 16, 2016

(87) PCT Pub. No.: WO2015/193326
PCT Pub. Date: Dec. 23, 2015

(65) Prior Publication Data
US 2017/0210822 A1 Jul. 27, 2017

Related U.S. Application Data

(60) Provisional application No. 62/030,817, filed on Jul. 30, 2014.

(30) Foreign Application Priority Data

Jun. 16, 2014 (NL) ..................................... 2013007

(51) Int. Cl.
*C07K 16/36* (2006.01)
*A61K 38/36* (2006.01)
*A61K 39/00* (2006.01)

(52) U.S. Cl.
CPC .............. *C07K 16/36* (2013.01); *A61K 38/36* (2013.01); *A61K 2039/505* (2013.01); *A61K 2039/545* (2013.01); *C07K 2317/24* (2013.01); *C07K 2317/565* (2013.01); *C07K 2317/567* (2013.01); *C07K 2317/569* (2013.01); *C07K 2317/76* (2013.01)

(58) Field of Classification Search
None
See application file for complete search history.

(56) References Cited

U.S. PATENT DOCUMENTS

| 7,270,976 B2* | 9/2007 | Greenfield | ............... | C12Q 1/37 435/23 |
| 7,807,162 B2* | 10/2010 | Silence | .................. | A61K 38/36 424/133.1 |
| 8,372,398 B2* | 2/2013 | Silence | .................. | A61K 38/36 424/133.1 |
| 2018/0155440 A1 | 6/2018 | Duby | | |
| 2018/0155441 A1 | 6/2018 | Duby | | |
| 2018/0155442 A1 | 6/2018 | Duby | | |
| 2018/0155443 A1 | 6/2018 | Duby | | |

FOREIGN PATENT DOCUMENTS

| EP | 0294025 A2 | 12/1988 | |
| EP | 0294025 A3 | 11/1989 | |
| IN | 255610 B | 3/2013 | |
| RU | 2364420 C2 | 8/2009 | |
| WO | WO 2006/030220 A1 | 3/2006 | |
| WO | WO-2006122825 A2 * | 11/2006 | ............. A61K 38/36 |
| WO | WO 2012/171031 A1 | 12/2012 | |

OTHER PUBLICATIONS

Van Audenhove et al., EBioMedicine. Jun. 2016;8:40-48. doi: 10.1016/j.ebiom.2016.04.028. Epub Apr. 30, 2016.*
Janeway et al., Immunobiology, 3rd edition, 1997, Garland Publishing Inc., pp. 3:1-3:11.*
Rudikoff et al., Proc Natl Acad Sci USA. Mar. 1982;79(6):1979-83.*
Edwards et al.,J Mol Biol. Nov. 14, 2003;334(1): 103-18.*
Llyod et al., Protein Eng Des Sel. Mar. 2009;22(3):159-68. doi: 10.1093/protein/gzn058. Epub Oct. 29, 2008.*
Goel et al., J Immunol. Dec. 15, 2004; 173(12):7358-67.*
Ghahroudi et al., FEBS Letters Sep. 15, 1997; 414(3): 521-526.*
Holz, JB, Transfus Apher Sci. Jun. 2012;46(3):343-6. doi: 10.1016/j.transci.2012.03.027. Epub Apr. 3, 2012.*
McLeod et al., Best Pract Res Clin Haematol. 2006;19(1):157-67.*
Callewaert et al., Evaluation of efficacy and safety of the anti-VWF Nanobody ALX-0681 in a preclinical baboon model of acquired thrombotic thrombocytopenic purpura. Blood. Oct. 25, 2012;120(17):3603-10. doi:10.1182/blood-2012-04-420943. Epub Sep. 4, 2012.
Cataland et al., Practical issues in ADAMTS13 testing and emerging therapies in thrombotic thrombocytopenic purpura. Semin Hematol. Oct. 2011;48(4):242-50. doi: 10.1053/j.seminhematol.2011.08.004.
Chapman et al., Therapy for thrombotic thrombocytopenia purpura: past, present, and future. Semin Thromb Hemost. Feb. 2014;40(1):34-40. doi:10.1055/s-0033-1363165. Epub Dec. 31, 2013.

(Continued)

*Primary Examiner* — Michael Szperka

(74) *Attorney, Agent, or Firm* — Wolf, Greenfield & Sacks, P.C.

(57) ABSTRACT

The present invention is based on the finding that administration of polypeptides comprising at least one Immunoglobulin single variable domains against vWF to human TTP patients provides a significant decrease in the time to response. The invention provides a polypeptide comprising at least one immunoglobulin single variable domain (ISVD) against von Willebrand Factor (vWF) for use in treating a vWF-related disease in a human in need thereof. The invention further relates to dosage unit forms, kits and medical uses for treating TTP.

20 Claims, 5 Drawing Sheets

Specification includes a Sequence Listing.

(56) References Cited

OTHER PUBLICATIONS

Holz, The TITAN trial—assessing the efficacy and safety of an anti-von Willebrand factor Nanobody in patients with acquired thrombotic thrombocytopenic purpura. Transfus Apher Sci. Jun. 2012;46(3):343-6. doi:10.1016/j.transci.2012.03.027. Epub Apr. 3, 2012.

Kremer Hovinga et al., Survival and relapse in patients with thrombotic thrombocytopenic purpura. Blood. Feb. 25, 2010;115(8):1500-11; quiz 1662. doi: 10.1182/blood-2009-09-243790. Epub Dec. 23, 2009.

Peyvandi et al., First results of the Phase II TITAN trial: anti-von Willebrand factor Nanobody® as adjunctive treatment for patients with acquired thrombotic thrombocytopenic purpura. Jul. 28, 2011. Retrieved from the Internet: http://www.ablynx.com/wp-content/uploads/2011/07/Peyvandi TITAN-study final.pdf on Jan. 21, 2015.

Peyvandi et al.: ADAMTS13 and anti-ADAMTS13 antibodies as markers for recurrence of acquired thrombotic thrombocytopenic purpura during remission. Haematologica. Feb. 2008;93(2):232-9. doi: 10.3324/haematol.11739. Epub Jan. 26, 2008.

Westwood et al., Rituzimab for thrombotic thrombocytopenic purpura: benefit of early administration during acute episodes and use of prophylaxis to prevent relapse. J Thromb Haemost. Mar. 2013;11(3):481-90. doi: 10.1111/jth.12114.

[No Author Listed] Study to Assess Efficacy and Safety of Anti-von Willebrand Factor Nanobody in Patients with Acquired Thrombotic Thrombocytopenic Purpura (TTP) (TITAN). NIH US National Library of Medicine. Jun. 28, 2010. https://clinicaltrials.gov/ct2/show/NCT01151423.

Cataland et al., Caplacizumab Treatment for Acquired Thrombotic Thrombocytopenic Purpura. N Engl J Med. Jan. 24, 2019;380(4):335-346. doi: 10.1056/NEJMoa1806311. Epub Jan. 9, 2019.

Sargentini-Maier et al., Clinical pharmacology of caplacizumab for the treatment of patients with acquired thrombotic thrombocytopenic purpura. Expert Rev Clin Pharmacol. Jun. 2019;12(6):537-545. doi: 10.1080/17512433.2019.1607293. Epub Apr. 28, 2019.

PCT/EP2015/063493, Dec. 29, 2016, International Preliminary Report on Patentability.

Gauer et al., Thrombocytopenia. Am Fam Physician. 2012;85(6):612-622.

Vanhoorelbeke et al., Animal models for thrombotic thrombocytopenic purpura. J Thromb Haemost. 2013;11 Suppl 1:2-10. doi:10.1111/jth.12255.

\* cited by examiner

Figure 1:
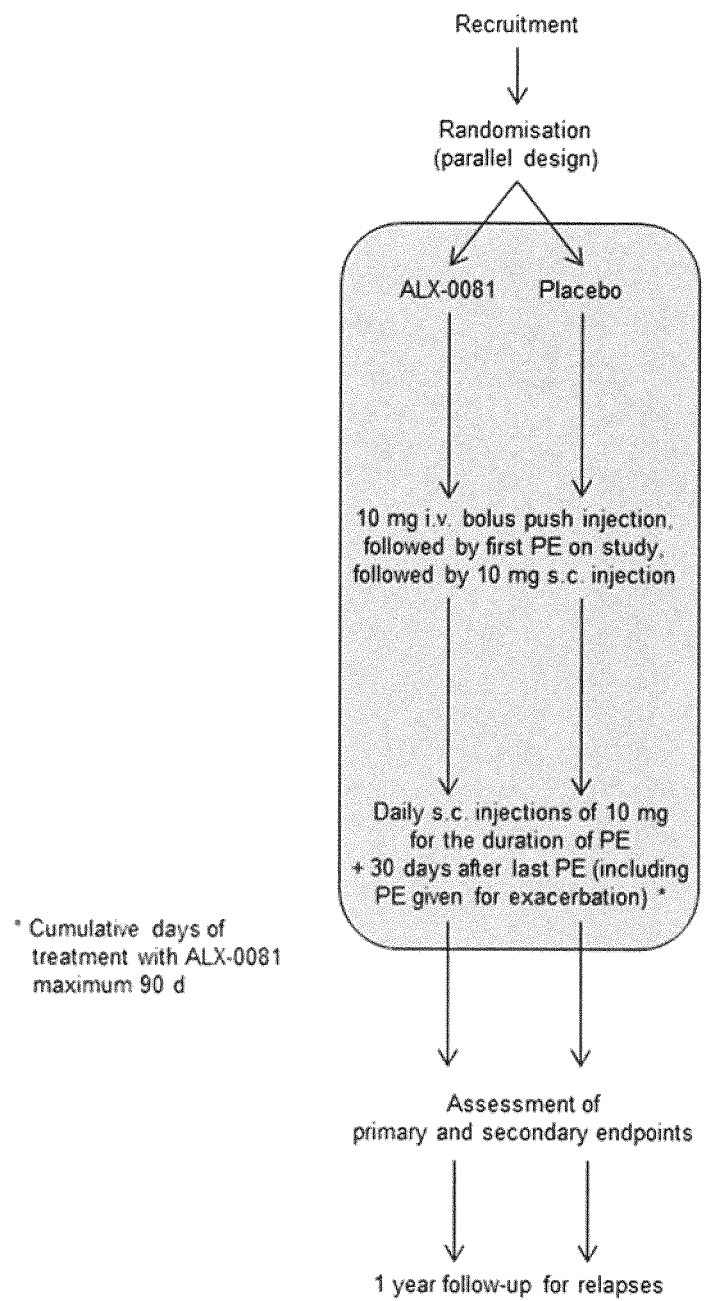

Figure 1: treatment flow chart

Figure 2:
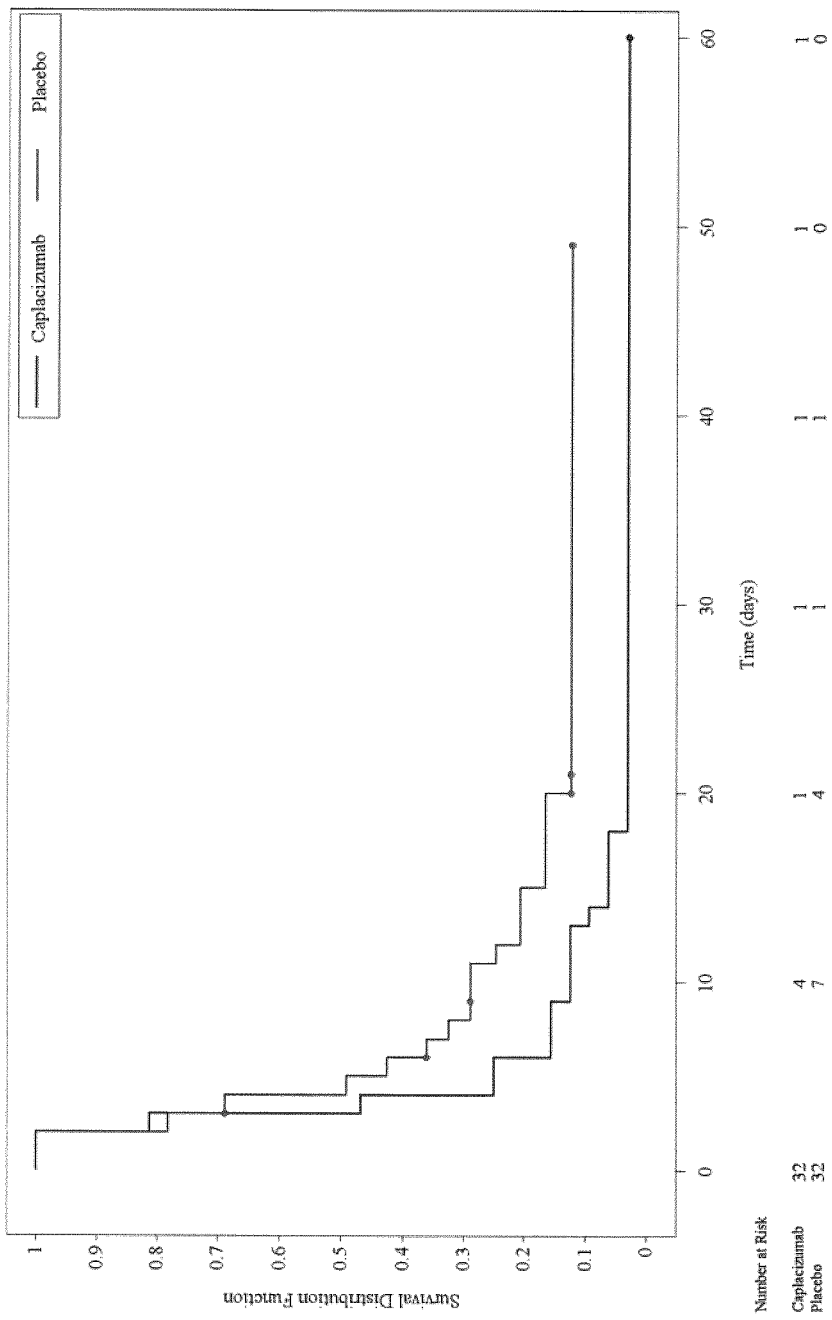

Figure 2 Time to first LDH normalisation curves (ITT population = subjects with abnormal high levels at baseline).

Figure 3:
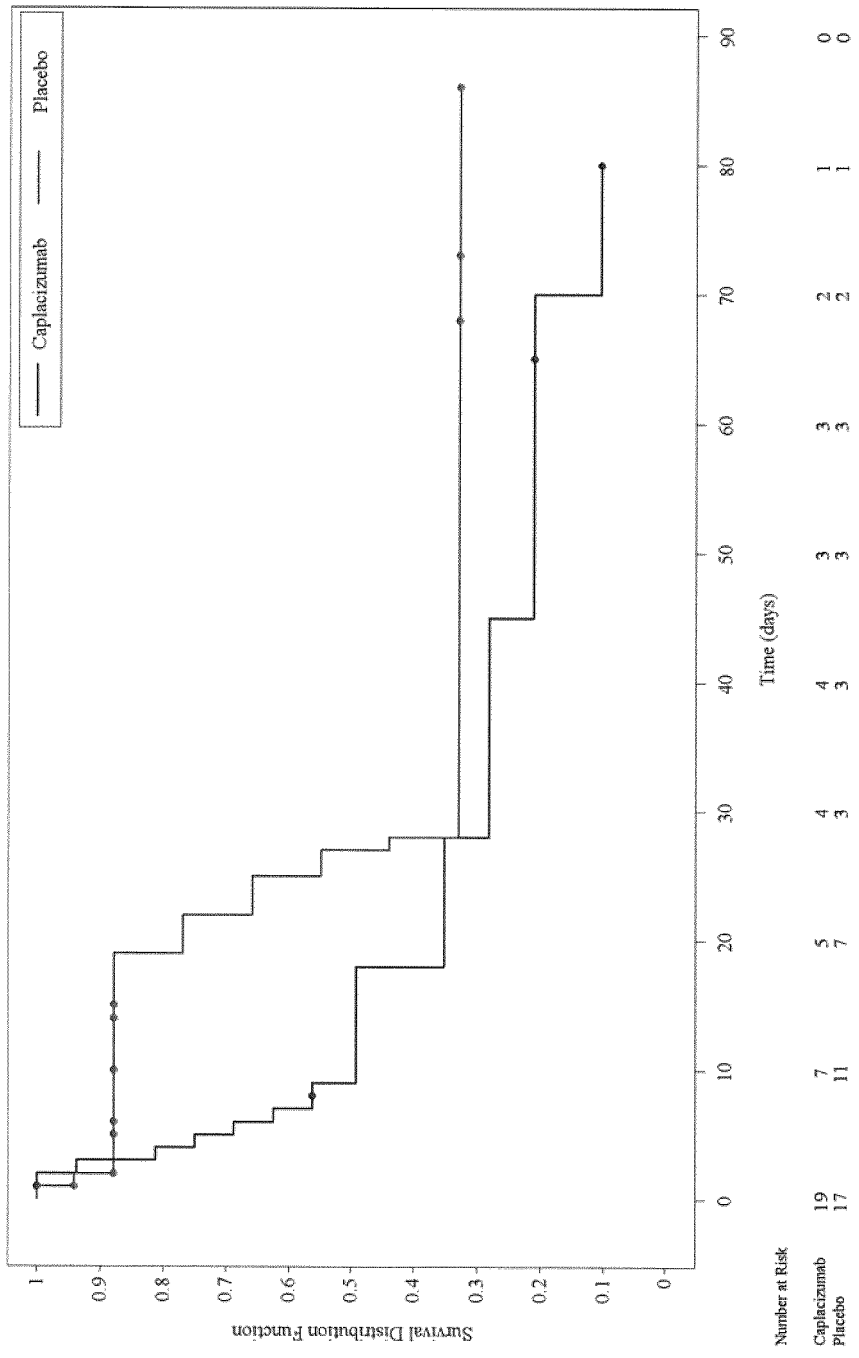

Figure 3: Time to Troponin T or I Normalization Curves for Subjects with Abnormal High Levels at Baseline in the Intent-To-Treat Population Figure 4: Time to Creatinine Normalization Curves for Subjects with Abnormal High Levels at Baseline in the Intent-To-Treat Population

METHODS OF TREATING TTP WITH IMMUNOGLOBULIN SINGLE VARIABLE DOMAINS AND USES THEREOF

RELATED APPLICATIONS

This application is a national stage filing under 35 U.S.C. § 371 of International Application No. PCT/EP2015/063493, filed Jun. 16, 2015, which was published under PCT Article 21(2) in English, and claims the benefit under 35 U.S.C. § 119(e) of U.S. provisional application Ser. No. 62/030,817, filed Jul. 30, 2014, the entire contents of each of which is incorporated by reference herein in its entirety.

1. FIELD OF THE INVENTION

The present invention is based on the finding that administration of polypeptides comprising at least one Immunoglobulin single variable domain against vWF to human TTP patients provides a significant decrease in the time to response and less complications. The invention provides a polypeptide comprising at least one immunoglobulin single variable domain (ISVD) against von Willebrand Factor (vWF) for use in treating a vWF-related disease in a human in need thereof. The invention further relates to dosage unit forms, kits and medical uses for treating TTP.

2. BACKGROUND OF THE INVENTION

2.1 Role of vWF in Platelet Aggregation

The multimeric plasma protein von Willebrand Factor (vWF) is essential for recruiting circulating platelets to the damaged vessel wall upon vascular injury. This recruitment is mediated through binding of the vWF A1-domain with the platelet receptor glycoprotein GPIb-IX-V.

Upon expression by endothelial cells, vWF is secreted into the circulation as ultra-large multimers or ultra-large vWF (ULvWF). These multimers are processed into smaller regular sized multimers through enzymatic cleavage by ADAMTS13. In these regular sized multimers of vWF, the GPIb-IX-V platelet receptor binding site in the A1 domain is cryptic and will not spontaneously react with platelets. A conformational activation of the GPIb-IX-V platelet receptor binding site in the A1 domain is triggered by immobilisation or under conditions of shear stress resulting in platelet adhesion and subsequently in thrombus formation.

2.2 Role of vWF and vWF Processing in Pathophysiology of TTP

Thrombotic thrombocytopenic purpura ("TTP") is a rare and life-threatening disease of the blood coagulation system, in which accumulation of ULvWF multimers has been implicated, leading to an increased risk of thrombus formation in small blood vessels due to excessive platelet aggregation. The condition is characterised by systemic platelet aggregation in the microcirculation, producing fluctuating ischaemia in many organs. If sustained, this may cause tissue infarction, associated with profound thrombocytopenia and erythrocyte fragmentation.

ULvWF multimers have the natural ability to spontaneously interact with the platelet receptor GPIb-IX-V. In healthy subjects, these ULvWF multimers are immediately processed into regular sized vWF multimers via cleavage by the vWF protease ADAMTS13. However, ADAMTS13 activity was found to be severely deficient in hereditary TTP as well as acquired idiopathic TTP. The majority of patients with TTP have autoantibodies against ADAMTS13 resulting in impaired processing of the ULvWF multimers. As a consequence, the A1 domain of the ULvWF is constitutively active and readily interacting with the GPIb-IX-V platelet receptor. This eventually results in formation of the characteristic blood clots found in the TTP patient population.

The current therapy of TTP with Plasma Exchange (abbreviated herein as "PE" or "PEX") and transfusion provides replacement ADAMTS13 and removes antibodies against the enzyme, thus progressively leading to a normalisation of ULvWF processing. However, this treatment requires multiple exchanges and transfusions over many days, during which time there is no direct pharmacological targeting of the active process of ULvWF-mediated platelet aggregation.

Although the introduction of PE and transfusion has significantly reduced the mortality rates from TTP over the last three decades, the condition still carries a significant risk of mortality and morbidity. The mortality rate of acute bouts in acute idiopathic TTP, in patients managed with the current therapies remains in the order of 10% to 30% (Vesely et al. Blood 2003; 102: 60-68; Afford et al. Br. J. Haematol. 2003; 120: 556-573; Sadler et al. Hematology. Am. Soc. Hematol. Educ. Program. 2004; 407-423). In the case of secondary TTP, PE and transfusion are recognised to be less effective and the mortality rate is considerably higher. In the cases when the disease is secondary to pregnancy, in which PE is regarded as reasonably effective the mortality rate of an acute bout of TTP is approximately 25%, rising to over 40% in cases with concurrent pre-eclampsia (Martin et al. Am. J. Obstet. Gynecol. 2008; 199: 98-104). However, in cases secondary to, for example, underlying malignancies or bone marrow transplant the mortality rate remains at 40% to 60% despite the use of such treatment regimens (Sadler et al. 2004 supra; Elliott et al. Mayo Clin. Proc. 2003; 78: 421-430; Kremer Hovinga and Meyer Curr. Opin. Hematol. 2008; 15: 445-450.)

Given the continuing significant level of mortality from TTP and the observed complications of PE and transfusion, there is a clear need for the development of additional therapeutic approaches to supplement, or potentially reduce the need for, these methods of treatment.

The research conducted into TTP over the past three decades has improved the understanding of the pathophysiology of the disease allowing for the potential development of novel agents targeting the underlying disease processes. Nevertheless, there are no currently approved therapies for TTP, and although there are newer therapies currently undergoing evaluation, the studies of these potential treatments are at a relatively early stage.

Immunoglobulin single variable domains (ISVDs) against vWF have been described in, for example WO2004/015425, WO2004/062551, WO2006/074947, WO2006/122825, WO2009/115614 and WO2011/067160.

It has been shown that ISVDs against vWF (e.g. ALX 0081) avidly bind to multimeric vWF, thereby blocking the interaction of any sizes and activation stages of multimeric vWF with the GPIb-IX-V platelet receptor. The interaction of ALX 0081 with vWF is highly specific and it does not interact with human blood cells or platelets. Furthermore, its interference with the platelet GPIb-IX-V receptor is selective through the binding of the vWF A1 domain and it does not affect the capacity of vWF to interact with fibrillar collagens or with collagen type VI. It has also been shown that ISVDs against vWF (e.g. ALX 0081) do not affect the activity of the (remaining) vWF-protease ADAMTS13, nor do they interfere with the binding of FVIII to vWF.

In a phase I study it has been shown that ALX 0081 is safe and well tolerated in healthy volunteers.

However, the human healthy volunteers are not predictive for the efficacy of ISVDs against vWF in general or ALX 0081 specifically in the underlying pathology of TTP patients. vWF is abnormal in quantity as well as quality in TTP patients. Although it is accepted that ULvWF does not function normally in hemostasis in TTP patients, the underlying mechanism is not understood. In TTP patients, higher vWF levels are expected during acute episodes (Lotta et al. 2011 J Thromb Haemost 9: 1744-51; Stufano et al. 2012 J Thromb Haemost 10:728-730).

Due to the lack of a relevant animal model, no in viva efficacy of ALX 0081 to neutralise ULvWF has been demonstrated.

Therefore, it remains to be elucidated whether polypeptides comprising at least one ISVD against vWF, such as ALX 0081, are beneficial in TTP patients, whether polypeptides comprising at least one ISVD against vWF, such as ALX 0081, have a positive effect over PE, and what an effective treatment and dose regimen would be.

There is a need for improved therapies for TTP patients.

3. SUMMARY OF THE INVENTION

The present invention is based on the unexpected finding that the administration of polypeptides comprising at least one ISVD against vWF to human TTP patients provides a decrease of 2 days in the time-to-response, objectified by a recovery of platelets ≥150,000/µL. Platelet count increase is a sign of diminished pathological platelet aggregation, thereby decreasing the thrombotic process initiated by the platelet-vWF complexes characteristic of this disease. The Hazard Ratio ("HR") of placebo over the polypeptide of the invention was an astonishing of 2.2 with 95% CI (1.28, 3.78), p=0.013. This response was confirmed up to 48 hours after the time-to-response. Hence, proof of concept of the polypeptide of the invention was demonstrated with statistically significant and clinically meaningful reduction of time to confirmed platelet response. Furthermore, there was a reduction in the number of exacerbations from 11 in the Placebo arm to 3 in the treatment arm. There were no deaths in the treatment arm compared to 2 deaths in the Placebo arm.

Moreover, the present clinical study with UP patients also demonstrates that the polypeptides of the present invention (e.g. ALX 0081) are well tolerated agents and, in particular, that the potential for the risk of bleeding appears to be present but low and manageable. The currently available data demonstrate, therefore, that the reduction in PE and transfusion and their associated complications are achieved without significant adverse effects from the use of the polypeptides of the invention itself. This represents a clear safety benefit for the use of the polypeptides of the invention in the treatment of patients with TTP.

Hence, the administration of polypeptides comprising at least one ISVD against vWF to human TTP patients provides an unexpectedly decreased time-to-response, a sustained and prolonged effect, reduced exacerbations, reduced hospitalization, reduced morbidity, reduced deaths and/or a reduced number of PEs.

The current therapy of TTP with PE and transfusion provides replacement ADAMTS13 and removes antibodies against the enzyme, thus progressively leading to a normalisation of ULvWF processing. However, this treatment requires multiple exchanges and transfusions over many days, during which time there is no direct pharmacological targeting of the active process of ULvWF-mediated platelet aggregation.

It has now furthermore unexpectedly been shown that the polypeptides of the present invention do not interfere with the enzyme replaced by plasma transfusion. It has been demonstrated that the polypeptides of the invention (e.g. ALX 0081) can be utilized, in combination with PE and transfusion, to directly inhibit the continuing formation of small thrombi and platelet consumption in the microvasculature. This permits more rapid control of the underlying thrombotic process and accompanying platelet consumption, with the benefits of a reduced degree of ischaemic and haemorrhagic complications. It also results in a more rapid clinical recovery and less morbidity with a shorter period and reduced number of PEs and transfusions. Indeed, an analysis on the specific and clinically relevant organ damage biomarkers LDH, troponin T or I and creatinine suggested that more rapidly curtailing microvascular tissue ischemia could be expected to have a clinical benefit. In addition, the demonstrated inhibition of ULvWF-mediated platelet interaction by the polypeptides of the invention (e.g. ALX 0081) and the observed antithrombotic effects raise the potential for its longer-term use after patients have recovered from an acute bout of TTP to prevent relapses of the disease. A reduced frequency of acute bouts of TTP represents a significant benefit, with a potential for a reduction in the mortality and morbidity associated with UP and a further reduction in the need for PE and transfusions over a patient's lifetime.

While a more rapid recovery from TTP and a reduction in exacerbations and relapses is a clear clinical benefit in terms of treatment efficacy, the reduction in the duration and frequency of PE and transfusion also provides additional benefits in terms of patient safety. Although PE and transfusion are currently regarded as the standard treatment in the management of TTP (Scully et al. Br. J. Haem. 2012; 158:323-335), the procedures carry the risk of significant complications. The PE procedure requires high fluid volumes and flow rates necessitating the use of central venous dual lumen haemodialysis catheters. Complications from the procedure include haemorrhage from catheter insertion, sepsis, catheter thrombosis, pneumothorax, fluid overload, hypoxia and hypotension (Fontana et al. Semin. Hematol. 2004; 41: 48-59; George J. Intensive Care Med. 2007; 22: 82-91; Howard et al. Transfusion 2006; 46: 154-156; Rizvi et al. Transfusion 2000; 40: 896-901; Nguyen et al. Transfusion 2009; 49: 392-394). Anaphylactoid reactions complicate 0.25% to 0.5% of procedures (Allford et al 2003 supra; George 2007 supra). In addition, the infusion of plasma containing blood products can cause a non-infective TRALI. This condition is recognized as one of the most frequent causes of transfusion-related fatalities with an incidence estimated to be 0.02% to 0.05% per plasma containing unit with a daily average of 17 plasma units, the daily risk can be calculated to a range of 0.34% to 0.85%. Most patients with UP require multiple PEs and transfusions. Patients with acute idiopathic UP require daily treatments, and an average of approximately 16 treatments is required to achieve remission (Allford et al. 2003 supra). In refractory cases the frequency of treatment may be increased to twice-daily (Allford et al. 2003 supra). In the case of patients with familial UP, regular prophylactic plasma infusions at two to three week intervals are recommended (Lammle et al. J. Thromb. Haemost. 2005; 3: 1663-1675). Anaphylaxis and TRALI thus represent clear risks to patients with TTP whose treatment requires such a frequency and regularity of PEs and transfusions. While it is thought that this risk may be lower if solvent/detergent (S/D) treated plasma is used instead of fresh frozen plasma, the use of large volumes of S/D plasma may be associated with an increased risk of venous thromboembolism (Afford et al. 2003 supra; Fontana et al. 2004 supra). Overall, it is estimated that approximately 30% to 40% of patients will experience adverse effects from PE and transfusion, and the mortality rate from the procedure is of the order of 2% to 3% (George et al. Semin. Hematol. 2004; 41: 60-67; George 2007 supra). Hence, the reduction in the duration and frequency of PE and transfusion also provides additional benefits in terms of patient safety.

Following recovery from a bout of TTP, many patients describe cognitive abnormalities for many years and report troublesome problems with memory, concentration, decreased energy and fatigue. Such symptoms have a negative impact on the quality of patients' daily lives. Furthermore, this deficit in quality of life may occur in all patients who have TTP, regardless of the aetiology and severity (Lewis et al. Transfusion 2009; 49: 118-124). It is thought that these symptoms may be reflective of the residual effects of tissue ischaemia. On this basis, it can be reasonably proposed that a more rapid recovery from TTP and the limitation of thrombus formation in the microvasculature that the polypeptides of the present invention, such as ALX 0081, provide, results in an improved longer-term outcome for the patients in terms of their quality of life.

Accordingly, the present invention provides methods for treating or alleviating vWF-related diseases in a subject by administering to the subject a polypeptide comprising at feast one ISVD against vWF, wherein the amount of the polypeptide administered is effective to reduce the time-to-response, to reduce exacerbations, to reduce hospitalization, to reduce ischemia, to reduce the death toll and/or to reduce the number of required PEs. The present invention provides specific dose ranges and dosing schedules for the polypeptides of the invention that result in one or more of these effects on vWF-related disease. In particular, the invention provides pharmacologically active agents, compositions, methods and/or dosing schedules that have certain advantages compared to the agents, compositions, methods and/or dosing schedules that are currently used and/or known in the art, including the requirement to less frequently give PE. These advantages will become clear from the further description below.

Accordingly, the present invention provides a polypeptide comprising at least one immunoglobulin single variable domain (ISVD) against von Willebrand Factor (vWF) for use in treating a vWF-related disease in a human in need thereof, comprising administering to said human a first dose of 1-80 mg, such as 5-40 mg, preferably 10 mg of said polypeptide.

The present invention provides a polypeptide as described herein, wherein said administering said polypeptide is followed within 5 min to 8 h by performing a first Plasma Exchange (PE).

The present invention provides a polypeptide as described herein, wherein said administering of said first dose is preceded by performing a preceded Plasma Exchange (PE), preferably within 36 h, such as within 32 h, 30 h, 28 h, 26 h, 24 h, 22 h, 20 h, 18 h, 16 h, 14 h, 12 h, 10 h, 8 h, for instance within 7 h, 6 h, 5 h, 4 h, 3 h, 3 h, 1 h, 45 min, 30 min, 20 min, 15 min, 10 min or even 5 min of said first PE.

The present invention provides a polypeptide as described herein, wherein said first PE is followed by administering a second dose of 1-80 mg, such as 5-40 mg, preferably 10 mg, of said polypeptide, preferably by subcutaneous injection, preferably within 1-60 min, more preferably within 30 min of said first PE.

The present invention provides a polypeptide as described herein, wherein said preceded PE is performed within 36 h, preferably 32, 30, 28, 26, 24, 22, 20, 18, or 16 h, preferably about 24 h of said first PE.

The present invention provides a polypeptide as described herein, wherein said polypeptide is administered parenterally, preferably by subcutaneous, intraperitoneal, intravenous or intramuscular injection, preferably by an intravenous (i.v.) bolus push injection.

The present invention provides a polypeptide as described herein, wherein said administering said polypeptide is followed by performing a PE within 5 min to 8 h, such as within 10 min to 6 h or 15 min to 4 h, for instance within 8 h, 7 h, 6 h, 5 h, 4 h, 3 h, 3 h, 1 h, 45 min, 30 min, 20 min, 15 min, 10 min or even 5 min.

The present invention provides a polypeptide as described herein, wherein said treating a vWF-related disease in a human in need thereof, further comprises:
(i) performing a PE; and (followed by)
(ii) administering a dose of 1-80 mg, such as 5-40 mg of said polypeptide 5 min to 4 h after said PE of step (i); and
(iii) optionally measuring the platelet count and/or ADAMTS13 activity of said patient,
wherein step (i) and step (ii) are repeated once per day, preferably until the platelet count of said patient is ≥150000/μl and/or said ADAMTS13 activity is at least 10% such as at least 15%, 20%, 25%, 30%, 35%, 45% or even 50% of the ADAMTS13 reference activity.

The present invention provides a polypeptide as described herein, further comprising administering once per day a dose of 1-80 mg, such as 5-40 mg, preferably 10 mg of said polypeptide for at least 5, 10, 15, 20, 25, 30, 40, 50 60, 90 or even 120 days after the platelet count of said patient is ≥150.000/μl for the first time.

The present invention provides a polypeptide as described herein, further comprising administering once per day a dose of 1-80 mg, such as 5-40 mg, preferably 10 mg of said polypeptide until said human enters remission.

The present invention provides a polypeptide as described herein, comprising administering said polypeptide until the ADAMTS13 activity is at least 10% such as at least 15%, 20%, 25%, 30%, 35%, 45% or even 50% of the ADAMTS13 reference activity.

The present invention provides a polypeptide as described herein, wherein said dose is about 1-80 mg, or 5-40 mg, such as 1, 2, 3, 4, 5, 6, 7, 8, 9, 10, 11, 12, 13, 14, 15, 16, 17, 18, 19, 20, 25, 30, 35, 40, 50, 60, 70 or 80 mg, preferably about 10 mg of said polypeptide.

The present invention provides a polypeptide as described herein, wherein said human suffers from an acute episode of TTP, an exacerbation of TTP or a relapse of TTP.

In a preferred aspect, the present invention provides a polypeptide comprising at least one immunoglobulin single variable domain (ISVD) against von Willebrand Factor (vWF) for use in treating a vWF-related disease in a human in need thereof, comprising
(1) optionally performing a preceded Plasma Exchange (PE);
(2) administering to said human a first dose of 1-80 mg, such as 5-40 mg, preferably 10 mg of said polypeptide, and if step (1) is performed preferably within 36 h, such as within 32 h, 30 h, 28 h, 26 h, 24 h, 22 h, 20 h, 18 h, 16 h, 14 h, 12 h, 10 h, 8 h, for instance within 7 h, 6 h, 5 h, 4 h, 3 h, 3 h, 1 h, 45 min, 30 min, 20 min, 15 min, 10 min or even 5 min of (the end of) step (1);

(3) performing a Plasma Exchange (PE), optionally within 5 min to 8 h, such as within 10 min to 6 h or 15 min to 4 h, for instance within 8 h, 7 h, 6 h, 5 h, 4 h, 3 h, 3 h, 1 h, 45 min, 30 min, 20 min, 15 min, 10 min or even 5 min of step (2);

(4) administering a further dose of 1-80 mg, such as 5-40 mg, preferably 10 mg of said polypeptide preferably within 5 min to 8 h, such as within 10 min to 6 h or 15 min to 4 h, for instance within 8 h, 7 h, 6 h, 5 h, 4 h, 3 h, 3 h, 1 h, 45 min, 30 min, 20 min, 15 min, 10 min or even 5 min of (the end of) step (3);

(5) repeating step (3) and step (4) once per day; optionally until the platelet count of said patient is ≥150000/µl and/or said ADAMTS13 activity is at least 10% such as at least 15%, 20%, 25%, 30%, 35%, 45% or even 50% of the ADAMTS13 reference activity.

(6) optionally administering once per day a dose of 1-80 mg, such as 5-40 mg, preferably 10 mg of said polypeptide for at least 5, 10, 15, 20, 25, 30, 40, 50 60, 90 or even 120 days after the platelet count of said patient is ≥150.000/µl for the first time or until the ADAMTS13 activity is at least 10% such as at least 15%, 20%, 25%, 30%, 35%, 45% or even 50% of the ADAMTS13 reference activity.

In addition, the present invention provides a polypeptide comprising two anti-human vWF ISVDs for use in preventing (the symptoms of) a relapse of an vWF-related disease in a human, by administering to the human 1-80 mg, such as 5-40 mg, preferably 10 mg doses of said polypeptide.

The present invention provides a polypeptide as described herein, wherein said ISVD against vWF comprises at least one immunoglobulin single variable domain binding to SEQ ID NO: 20.

The present invention provides a polypeptide as described herein, wherein said ISVD against vWF comprises a heavy chain variable domain which is derived from a conventional four-chain antibody or a heavy chain variable domain which is derived from a heavy chain antibody or a Nanobody.

The present invention provides a polypeptide as described herein, wherein said Nanobody is a VHH.

The present invention provides a polypeptide as described herein, wherein said the ISVD against vWF essentially consists of 4 framework regions (FR1 to FR4, respectively) and 3 complementarity determining regions (CDR1 to CDR3, respectively), in which:
a) CDR1 comprises or essentially consists of:
  the amino acid sequence YNPMG; or
  an amino acid sequence that has 2 or only 1 amino acid difference(s) with the amino acid sequence YNPMG;
and
b) CDR2 comprises or essentially consists of:
  the amino acid sequence AISRTGGSTYYPDSVEG; or
  an amino acid sequence that has at least 80%, preferably at least 90%, more preferably at least 95%, even more preferably at least 99% sequence identity with the amino acid sequence AISRTGGSTYYPDSVEG; or
  an amino acid sequence that has 2 or only 1 amino acid difference(s) with the amino acid sequence AISRTGGSTYYPDSVEG;
and
c) CDR3 comprises or essentially consists of:
  the amino acid sequence AGVRAEDGRVRTLPSEYTF; or
  an amino acid sequence that has at least 80%, preferably at least 90%, more preferably at least 95%, even more preferably at least 99% sequence identity with the amino acid sequence AGVRAEDGRVRTLPSEYTF; or
  an amino acid sequence that has 2 or only 1 amino acid difference(s) with the amino acid sequence AGVRAEDGRVRTLPSEYTF.

The present invention provides a polypeptide as described herein, in which:
a) CDR1 is YNPMG (SEQ ID NO: 20);
b) CDR2 is AISRTGGSTYYPDSVEG (SEQ ID NO: 21); and
c) CDR3 is AGVRAEDGRVRTLPSEYTF (SEQ ID NO: 22).

The present invention provides a polypeptide as described herein, wherein the ISVD against vWF is represented by SEQ ID NO: 19 (12A02H1).

The present invention provides a polypeptide as described herein, comprising or consisting of at least two ISVDs against vWF.

The present invention provides a polypeptide as described herein, wherein each ISVD of said at least two ISVDs against vWF essentially consists of 4 framework regions (FR1 to FR4, respectively) and 3 complementarity determining regions (CDR1 to CDR3, respectively), in which:
a) CDR1 comprises or essentially consists of:
  the amino acid sequence YNPMG; or
  an amino acid sequence that has 2 or only 1 amino acid difference(s) with the amino acid sequence YNPMG;
and
b) CDR2 comprises or essentially consists of:
  the amino acid sequence AISRTGGSTYYPDSVEG; or
  an amino acid sequence that has at least 80%, preferably at least 90%, more preferably at least 95%, even more preferably at least 99% sequence identity with the amino acid sequence AISRTGGSTYYPDSVEG; or
  an amino acid sequence that has 2 or only 1 amino acid difference(s) with the amino acid sequence AISRTGGSTYYPDSVEG;
and
c) CDR3 comprises or essentially consists of:
  the amino acid sequence AGVRAEDGRVRTLPSEYTF; or
  an amino acid sequence that has at least 80%, preferably at least 90%, more preferably at least 95%, even more preferably at least 99% sequence identity with the amino acid sequence AGVRAEDGRVRTLPSEYTF; or
  an amino acid sequence that has 2 or only 1 amino acid difference(s) with the amino acid sequence AGVRAEDGRVRTLPSEYTF.

The present invention provides a polypeptide as described herein, in which each ISVD against vWF essentially consists of 4 framework regions (FR1 to FR4, respectively) and 3 complementarity determining regions (CDR1 to CDR3, respectively), in which:
a) CDR1 is YNPMG (SEQ ID NO: 20);
b) CDR2 is AISRTGGSTYYPDSVEG (SEQ ID NO: 21); and
c) CDR3 is AGVRAEDGRVRTLPSEYTF (SEQ ID NO: 22).

The present invention provides a polypeptide as described herein, wherein said polypeptide comprises or consists of SEQ ID NO:s 1-19, preferably SEQ ID NO: 19.

The present invention provides a polypeptide as described herein, wherein said ISVD against vWF is a single chain polypeptide comprising one or more immunoglobulin single variable domains.

The present invention provides a polypeptide as described herein, wherein said ISVD against vWF is monovalent or multivalent.

The present invention provides a polypeptide as described herein, wherein said ISVD against vWF is monospecific or multispecific.

The present invention provides a polypeptide as described herein, wherein one or more immunoglobulin single variable domains are CDR-grafted, humanized, camelized, de-immunized, or selected by phage display.

The present invention provides a polypeptide as described herein, wherein said ISVD against vWF comprises an amino acid sequence which is at least 90% identical to SEQ ID NO: 1.

The present invention provides a polypeptide as described herein, comprising two anti-human vWF immunoglobulin single variable domains (ISVDs) and an anti-human serum albumin (HSA) ISVD The present invention provides a polypeptide as described herein, wherein said polypeptide is formulated in a pharmaceutically acceptable formulation.

The present invention provides a polypeptide as described herein, wherein said formulation comprises a citrate or phosphate buffer with a pH in the range of 5.0 to 7.5.

The present invention provides a polypeptide as described herein, wherein said formulation is suitable for parenteral administration, such as one or more selected from intravenous injection, subcutaneous injection, intramuscular injection or intraperitoneal injection.

The present invention provides a polypeptide as described herein, wherein said formulation is in liquid, lyophilized, spray-dried, reconstituted lyophilized or frozen form.

The present invention provides a kit or an article of manufacture, comprising a container containing the polypeptide as described herein or the formulation as described herein, and instructions for use.

The present invention provides a kit or article of manufacture as described herein, wherein the formulation is present in a vial or an injectable syringe.

The present invention provides a kit or article of manufacture as described herein, wherein the formulation is present in a prefilled injectable syringe.

The present invention provides a kit or article of manufacture as described herein, wherein the syringe or a vial is composed of glass, plastic, or a polymeric material chosen from a cyclic olefin polymer or copolymer.

The present invention provides a formulation comprising:
(a) a vWF binder at a concentration from about 0.1 mg/mL to about 80 mg/mL;
(b) an excipient chosen from sucrose, glycine, mannitol, trehalose or NaCl at a concentration of about 1% to about 15% (w/v);
(c) Tween-80 at a concentration of about 0.001% to 0.5% (v/v); and
(d) a buffer chosen from citrate buffer at a concentration of about 5 mM to about 200 mM such that the pH of the formulation is about 6.0 to 7.0 and a phosphate buffer at a concentration of about 10 mM to about 50 mM such that the pH of the formulation is about 6.5 to 7.5,
for use in treating a vWF-related disease in a human in need thereof, by administering to the human a 1-80 mg, such as 5-40 mg dose, preferably 10 mg of said polypeptide, wherein said dose is followed within 5 min to 8 h, such as 15 min to 4 h by a first Plasma Exchange (PE).

The present invention provides a pharmaceutical unit dosage form suitable for parenteral administration to a patient, preferably a human patient, comprising a polypeptide as described herein or a formulation as described herein.

The present invention provides a polypeptide as described herein, wherein said vWF-related disease is chosen from acute coronary syndrome (ACS), transient cerebral ischemic attack, unstable or stable angina pectoris, stroke, myocardial infarction or thrombotic thrombocytopenic purpura (TTP).

The present invention provides a method for the treatment of a human patient susceptible to or diagnosed with a disease characterized by a vWF-related disease, comprising administering an effective amount of a polypeptide comprising at least one immunoglobulin single variable domain (ISVD) against von Willebrand Factor (vWF) to the human patient.

The present invention provides a method of treating or preventing a vWF-related disease, such as TTP, comprising administering to a human, 1-80 mg, such as 5-40 mg, preferably 10 mg dose of a polypeptide comprising at least one immunoglobulin single variable domain (ISVD) against von Willebrand Factor (vWF), thereby reducing one or more symptoms associated with the vWF-related disease.

The present invention provides a treatment as described herein, wherein said administering a polypeptide as described herein is followed within 5 min to 8 h, such as 15 min to 4 h by performing a first Plasma Exchange (PE).

The present invention provides a treatment as described herein, wherein said administering of a polypeptide as described herein is preceded by performing a preceded Plasma Exchange (PE), within 36 h, preferably 32, 30, 28, 26, 24, 22, 20, 18, or 16 h, preferably about 24 h of said first PE.

The present invention provides a treatment as described herein, wherein said first PE is followed by administering a second dose of 1-80 mg, such as 5-40 mg, preferably 10 mg of a polypeptide as described herein within 5 min to 8 h, such as within 10 min to 6 h or 15 min to 4 h, for instance within 8 h, 7 h, 6 h, 5 h, 4 h, 3 h, 3 h, 1 h, 45 min, 30 min, 20 min, 15 min, 10 min or even 5 min, for instance wherein said second dose of said polypeptide is administered within 1-60 min, such as 30 min of said first PE, preferably by subcutaneous injection.

The present invention provides a treatment as described herein, further comprising:
(i) performing a PE; (followed by)
(ii) administering a dose of 1-80 mg such as 5-40 mg, preferably 10 mg of a polypeptide as described herein 15 min to 4 h after said PE of step (i); and
(iii) optionally measuring the platelet count and/or ADAMTS13 activity of said patient, wherein step (i) and step (ii) are repeated once per day optionally until the platelet count of said patient is ≥150000/μl and/or the ADAMTS13 activity is at least 10% such as at least 15%, 20%, 25%, 30%, 35%, 45% or even 50% of the ADAMTS13 reference activity.

The present invention provides also a treatment as described herein, further comprising administering once per day a dose of 1-80 mg, such as 5-40 mg, preferably 10 mg of a polypeptide as described herein for at least 5, 10, 15, 20, 25, or even 30 days after the platelet count of said patient is ≥150.000/μl.

The present invention provides a treatment as described herein, further comprising administering once per day a dose of 1-80 mg, such as 5-40 mg, preferably 10 mg of a polypeptide as described herein until said human enters remission.

The present invention provides a treatment as described herein, comprising administering said polypeptide until the ADAMTS13 activity is at least 10% such as at least 15%, 20%, 25%, 30%, 35%, 45% or even 50% of the ADAMTS13 reference activity.

In an embodiment, the present invention relates to a method for reducing the risk of and/or preventing an acute episode of a vWF-related disease in a human in need thereof, comprising or consisting of: (i) administering to said human a dose of 5-40 mg, preferably 10 mg, of a polypeptide comprising at least one immunoglobulin single variable domain (ISVD) against von Willebrand Factor (vWF); wherein administration of said polypeptide reduces the risk of and/or prevents an acute episode of a vWF-related disease. Preferably, said risk is reduced by a factor 1.2, 1.3, 1.4, 1.5, 1.6, 1.75, 1.8, 2 or more, such as 3, 4, 5, 6, 7, 8, 9, or even 10, or even more such as 20, 50 or even 100. Preferably, said risk is reduced by 10% or even more such as 20%, 30%, 40%, 50%, 60% or more, such as 80% or even 100%.

In an embodiment, the present invention relates to a method as described herein, wherein said step (i) of administering the polypeptide of the invention is repeated for at least 1, 2, 3, 4, 5, 6, 7, 8, 9, or 10 times, or even more than 10 times, such as 20 times, preferably more than 30 times or even more.

In an embodiment, the present invention relates to a method as described herein, wherein said step (i) of administering the polypeptide of the invention is repeated for at least 1, 2, 3, 4, 5, 6, 7, 8, 9, or 10 days, or even more than 10 days, such as 20 days, preferably more than 30 days, such as 2 months, 3 months, 4 months, 5 months, 6 months or even more.

In an embodiment, the present invention relates to a method as described herein, wherein said dose is administered 1 time per day or two times per day.

In an embodiment, the present invention relates to a method as described herein, further comprising
(ii) measuring the ADAMTS13 activity of said patient;
(iii) comparing said ADAMTS13 activity with a reference ADAMTS13 activity; and
(iv) if said ADAMTS13 activity is lower than 30%, such as 20%, 15% or 10% of said reference ADAMTS13 activity, then repeating said step (i) of administering the polypeptide of the invention.

In an embodiment, the present invention relates to a method as described herein, wherein said ADAMTS13 activity of said patient is measured every day, or every 2, 3, 4, 5, 6, 7, 8, 9, or 10 days, preferably at least once every week.

In an embodiment, the present invention relates to a method as described herein, wherein step (i) of administering the polypeptide of the invention is repeated until said ADAMTS13 activity is at least 10%, 15%, such 20%, or even 30% or higher of said reference ADAMTS13 activity.

In an embodiment, the present invention relates to a method as described herein, wherein step (i) is repeated until said ADAMTS13 activity is at least 10%, 15%, such as 20% or 30% of said reference ADAMTS13 activity on at least 2 consecutive measurements. Preferably, said 2 consecutive measurements are at least 24 h, more preferably 48 h apart, such as at least 3 days apart, or even more such as, 4, 5, 6, or even 7 days apart, preferable a week apart.

In an embodiment, the present invention relates to a method as described herein, wherein said step (i) of administering the polypeptide of the invention is repeated for at least at least 1, 2, 3, 4, 5, 6, 7, 8, 9, or 10 days, or even more than 10 days, such as 20 days, preferably more than 30 days or even more, after said ADAMTS13 activity is at least 10% or 15%, such as 20% or 30% of said reference activity on at least 2 consecutive measurements.

In an embodiment, the present invention relates to a method as described herein, further comprising
measuring the ADAMTS13 activity of said patient;
comparing said ADAMTS13 activity with a reference ADAMTS13 activity; and
if said ADAMTS13 activity is ≥10%, such as more than 15%, or more than 20% or 30% of said reference ADAMTS13 activity, then repeating said step (i) of administering the polypeptide of the invention for at most 30 days, such as at most 20 days, or even 15, 10, 9, 8, 7, 6, 5, 4, 3, 2 days or even 1 day.

In an embodiment, the present invention relates to a method for reducing the risk of and/or preventing an acute episode of a vWF-related disease in a human in need thereof, comprising at least the following steps:
(i) measuring the ADAMTS13 activity of said patient;
(ii) comparing said ADAMTS13 activity with a reference ADAMTS13 activity; and
(iii) if said ADAMTS13 activity is lower than 30%, 20%, 15% or 10% of said reference activity, then administering to said human a dose of 5-40 mg of a polypeptide comprising at least one immunoglobulin single variable domain (ISVD) against von Willebrand Factor (vWF);

In an embodiment, the present invention relates to a method as described herein, wherein
the risk of organ damage, ischaemic damage and/or microthrombi formation is reduced by 10%, 20%, 30%, preferably by at least 40%, or even at least 50%, such as 60%, 70%, 80%, 90% or even to 100%;
the risk of organ damage, ischaemic damage and/or microthrombi formation is reduced by a factor 1.2. 1.3, 1.4, 1.5, 1.75, 2 or more, such as 3, 4, 5, 6, 7, 8, 9, or even 10, or even more such as 20, 50 or even 100;
organ damage, ischaemic damage and/or microthrombi formation is reduced preferably by at least 10%, 20%, 30%, 40%, or even at least 50%, such as 60%, 70%, 80%, 90% or even to 100%;
organ damage, ischaemic damage and/or microthrombi formation is reduced by a factor, 2 or more, such as 3, 4, 5, 6, 7, 8, 9, or even 10, or even more such as 20, 50 or even 100;
organ damage markers, such as LDH levels, troponin T, troponin I levels, and/or creatinine levels, return to at least 40%, or even at least 50%, such as 60%, 70%, 80%, 90% or even to 100% of normal levels;
organ damage markers, such as LDH levels, troponin T, troponin I levels, and/or creatinine levels, improve by at least 20%, such 30% or even higher, such as 40%, or even at least 50%, such as 60%, 70%, 80%, 90% or even to 100% of normal levels. Preferably, said organ damage, such as LDH levels, troponin T, troponin I levels, and/or creatinine levels, markers improve in less than 30 days of treatment, preferably, in less than 20 days of treatment, such as, less than 15, 10, 9, 8, 7, 6, 5, 4, 3, 2 days or even within 1 day.
the number of platelets is kept at ≥150000/µl.
the risk of exacerbations is reduced by at least 10%, 20%, 30%, 40%, or even at least 50%, such as 60%, 70%, 80%, 90% or even to 100%;
the risk of exacerbations is reduced by a factor, 2 or more, such as 3, 4, 5, 6, 7, 8, 9, or even 10, or even more such as 20, 50 or even 100;

mortality due to said vWF related disease is reduced by 10%, 20%, 30%, preferably by at least 40%, or even at least 50%, such as 60%, 70%, 80%, 90% or even to 100%;

mortality due to said vWF related disease is reduced by a factor 1.2, 1.3, 1.4, 1.5, 1.6, 1.75, 1.8, 2 or more, such as 3, 4, 5, 6, 7, 8, 9, or even 10, or even more such as 20, 50 or even 100.

In an embodiment, the present invention relates to a method as described herein, further comprising measuring the platelet number; and if said platelet number is lower than 150,000/µl, then repeating said step (i) of administering the polypeptide of the invention.

In an embodiment, the present invention relates to a method as described herein, wherein said platelet number of said patient is measured every day, or every 2, 3, 4, 5, 6, 7, 8, 9, or 10 days, preferably at least every week.

In an embodiment, the present invention relates to a method as described herein, wherein step (i) of administering the polypeptide of the invention is repeated until said platelet number is at least 150,000/µl.

In an embodiment, the present invention relates to a method as described herein, wherein step (i) of administering the polypeptide of the invention is repeated until said platelet number is at least 150,000/µl on at least 2 consecutive measurements. Preferably, said 2 consecutive measurements are at least 24 h, more preferably 48 h apart, such as at least 3 days apart, or even more such as, 4, 5, 6, or even 7 days apart, preferable a week apart.

In an embodiment, the present invention relates to a method as described herein, wherein said step (i) of administering the polypeptide of the invention is repeated for at least at least 1, 2, 3, 4, 5, 6, 7, 8, 9, or 10 days, or even more than 10 days, such as 20 days, preferably more than 30 days or even more, after said platelet number is at least 150,000/µl on at least 2 consecutive measurements. Preferably, said 2 consecutive measurements are at least 24 h, more preferably 48 h apart, such as at least 3 days apart, or even more such as, 4, 5, 6, or even 7 days apart, preferably a week apart.

In an embodiment, the present invention relates to a method as described herein, further comprising measuring the platelet number of said patient; and if said platelet number ≥150,000/µl, then repeating said step (i) of administering the polypeptide of the invention for at most 30 days, such as at most 20 days, or even 15, 10, 9, 8, 7, 6, 5, 4, 3, 2 days or even 1 day.

In an embodiment, the present invention relates to a method for reducing the risk of and/or preventing an acute episode of a vWF-related disease in a human in need thereof, comprising at least the following steps:
(i) measuring the platelet number of said patient; and
(ii) if said platelet number is lower than 150,000/µl, then administering to said human a dose of 5-40 mg of a polypeptide comprising at least one immunoglobulin single variable domain (ISVD) against von Willebrand Factor (vWF);
wherein administration of said polypeptide reduces the risk of and/or prevents an acute episode of a vWF-related disease.

In an embodiment, the present invention relates to a method for treating an acute episode of a vWF-related disease, such as TTP, in a human in need thereof, comprising at least the following steps;
(i) administering to said human a first dose of 5-40 mg, preferably 10 mg of a polypeptide comprising at least one immunoglobulin single variable domain (ISVD) against von Willebrand Factor (vWF);

(ii) performing a first Plasma Exchange (PE), preferably within 5 min to 8 h of step (i).

In an embodiment, the present invention relates to a method for treating an acute episode of a vWF-related disease, such as TTP, in a human in need thereof, as described herein, wherein step (i), i.e. administering to said human the polypeptide of the invention, is preceded by performing a preceding PE, preferably within 24 h of step (ii), i.e. performing a first PE.

In an embodiment, the present invention relates to a method for treating an acute episode of a vWF-related disease, such as TTP, in a human in need thereof, comprising at least the following steps: (i) performing a Plasma Exchange (PE); (ii) administering to said human a dose of 5-40 mg, preferably 10 mg of a polypeptide comprising at least one immunoglobulin single variable domain (ISVD) against von Willebrand Factor (vWF). Preferably said step (i), i.e. performing a PE, and said step (ii) i.e. administering to said human said polypeptide of the invention, are repeated once or twice per day, for at most for 1, 2, 3, 4, 5, 6, or 7 days.

In an embodiment, the present invention relates to a method for treating an acute episode of a vWF-related disease, such as TTP, in a human in need thereof, as described herein, wherein step (ii) i.e. administering to said human said polypeptide of the invention, is performed within 15 min to 4 h of step (i), i.e. performing a PE.

In an embodiment, the present invention relates to a method for treating an acute episode of a vWF-related disease, such as TTP, in a human in need thereof, as described herein, further comprising measuring the platelet count of said human, preferably after step (ii) i.e. administering to said human said polypeptide of the invention; and if said platelet count is <150,000/µl, repeating said step (i) i.e. performing a PE, and said step (ii) i.e. administering to said human said polypeptide.

In an embodiment, the present invention relates to a method for treating an acute episode of a vWF-related disease, such as TTP, in a human in need thereof, as described herein, further comprising measuring the platelet count of said human [preferably after step (ii) i.e. administering to said human said polypeptide of the invention]; and repeating step (i), i.e. performing a PE, and step (ii) i.e. administering to said human said polypeptide, [once/twice per day] until said platelet number is at least 150,000/µl on at least 2 consecutive measurements. Preferably, said 2 consecutive measurements are at least 24 h, more preferably 48 h apart, such as at least 3 days apart, or even more such as, 4, 5, 6, or even 7 days apart, preferable a week apart.

In an embodiment, the present invention relates to a method for treating an acute episode of a vWF-related disease, such as TTP, in a human in need thereof, as described herein, further comprising administering once per day a dose of 5-40 mg, preferably 10 mg of said polypeptide for at least 1-30 days after the platelet count of said human was for the first time ≥150.000/µl.

In an embodiment, the present invention relates to a method for treating an acute episode of a vWF-related disease, such as TTP, in a human in need thereof, as described herein, further comprising measuring the ADAMTS13 activity of said human, preferably after step (ii) i.e. administering to said human said polypeptide.

In an embodiment, the present invention relates to a method for treating an acute episode of a vWF-related disease, such as TTP, in a human in need thereof, as described herein, wherein step (i), i.e. performing a PE, and step (ii) i.e. administering to said human said polypeptide of the invention, are repeated until the ADAMTS13 activity is [for the first time] more than 15%, or 20% or even 30% of a reference ADAMTS13 activity.

In an embodiment, the present invention relates to a method for reducing the risk of and/or preventing ischaemic damage, organ damage and/or microthrombi formation [causable by a vWF-related disease] in a human in need thereof, comprising at least the following step: (i)
administering to said human a dose of 5-40 mg/day, preferably 10 mg/day of a polypeptide comprising at least one immunoglobulin single variable domain (ISVD) against von Willebrand Factor (vWF); wherein administration of said polypeptide reduces the risk of and/or prevents ischaemic damage, organ damage and/or microthrombi formation by 10%, 20%, 30%, preferably by at least 40%, or even at least 50%, such as 60%, 70%, 80%, 90% or even to 100%. Preferably, administration of said polypeptide reduces the risk of and/or prevents ischaemic damage, organ damage and/or microthrombi formation by a factor 1.2, 1.3, 1.4, 1.5, 1.6, 1.75, 1.8, 2 or more, such as 3, 4, 5, 6, 7, 8, 9, or even 10, or even more such as 20, 50 or even 100.

In an embodiment, the present invention relates to a method wherein said step (i) of administering said polypeptide is repeated for at least 1, 2, 3, 4, 5, 6, 7 days, or even longer such as 1 week, 2 weeks, 3 weeks, or even longer such as 1 month or even 2 months In an embodiment, the present invention relates to a method further comprising measuring ADAMTS13 activity of said patient, preferably once per week.

In an embodiment, the present invention relates to a method wherein said step (i) of administering said polypeptide is repeated for at least 1, 2, 3, 4, 5, 6, 7 days, or even longer such as 1 week, 2 weeks, 3 weeks, or even longer such as 1 month or even 2 months when the ADAMTS13 activity is [for the first time]≥10%, such as more than 15%, or even more than 20% of a reference ADAMTS13 activity.

In an embodiment, the present invention relates to a method of treating a symptom of a vWF-related disease, such as TTP, in a human suffering from said disease, comprising administering to the subject a polypeptide of the invention, in an amount effective to treat the symptom of a vWF-related disease in a human suffering from said disease.

In an embodiment, the present invention relates to a method of inhibiting in a human the onset or progression of a vWF-related disease, such as TTP, the inhibition of which is effected by binding of a polypeptide comprising at least one immunoglobulin single variable domain (ISVD) against von Willebrand Factor (vWF) to vWF, comprising administering to the human at a predefined interval effective inhibitory doses of said polypeptide, wherein each administration of the polypeptide delivers to the human from 0.1 mg per kg to 25 mg per kg of the human's body weight, so as to thereby inhibit the onset or progression of the disease in the human.

In an embodiment, the present invention relates to a method of reducing the likelihood of a human contracting ischaemic organ damage by a vWF-related disease, which comprises administering to the human at a predefined dose a polypeptide comprising at least one immunoglobulin single variable domain (ISVD) against von Willebrand Factor (vWF), wherein each administration of the antibody delivers to the human from 0.1 mg per kg to 25 mg per kg of the human's body weight, so as to thereby reduce the likelihood of the human contracting ischaemic organ damage.

4. FIGURE LEGENDS

FIG. 1 Treatment flow chart.

FIG. 2 Time to first LDH normalisation curves (ITT population=subjects with abnormal high levels at baseline).

FIG. 3 Time to Troponin T or I Normalization Curves for Subjects with Abnormal High Levels at Baseline in the Intent-To-Treat Population.

Figure 4:
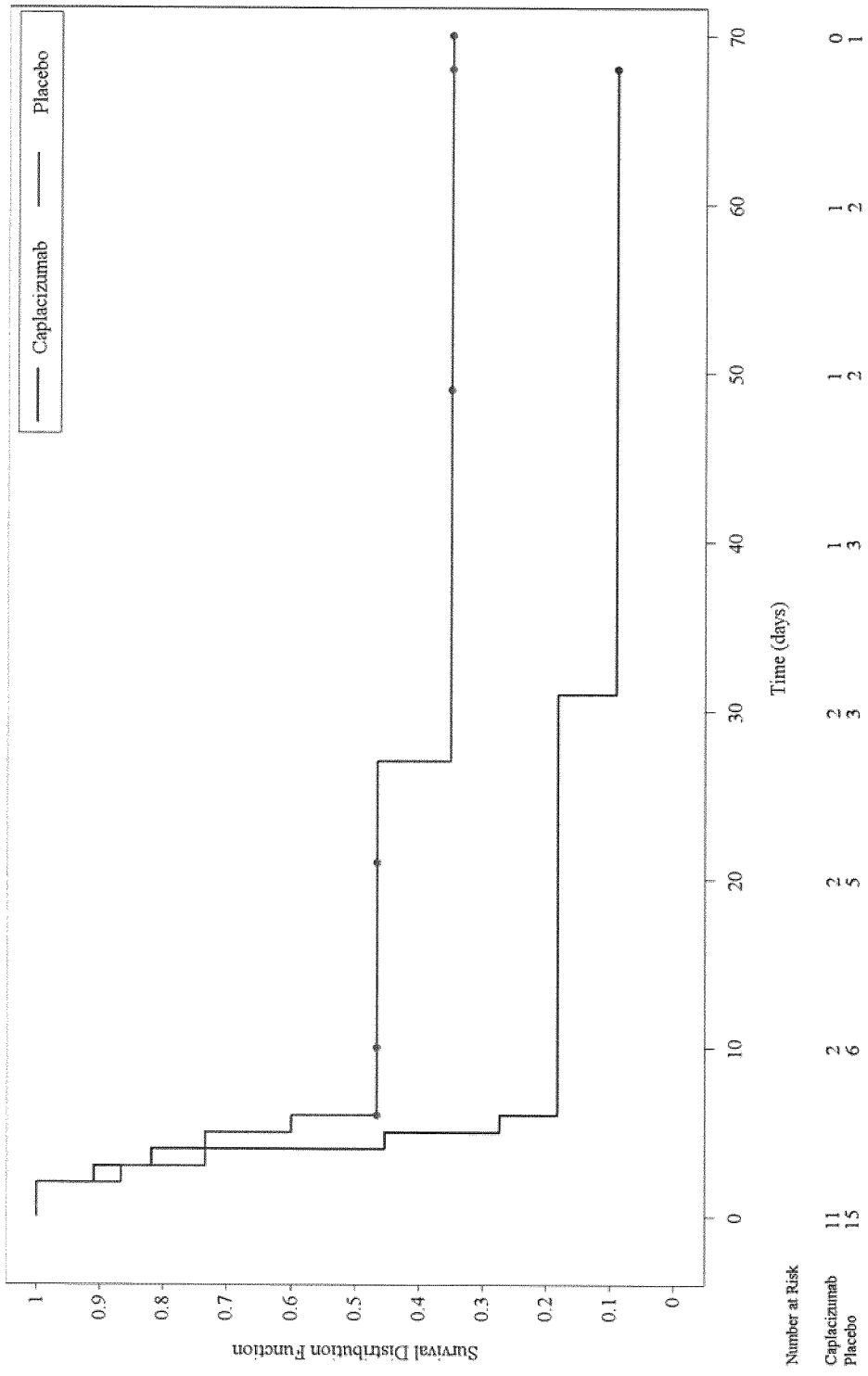

FIG. 4 Time to Creatinine Normalization Curves for Subjects with Abnormal High Levels at Baseline in the Intent-To-Treat Population.

Figure 5:
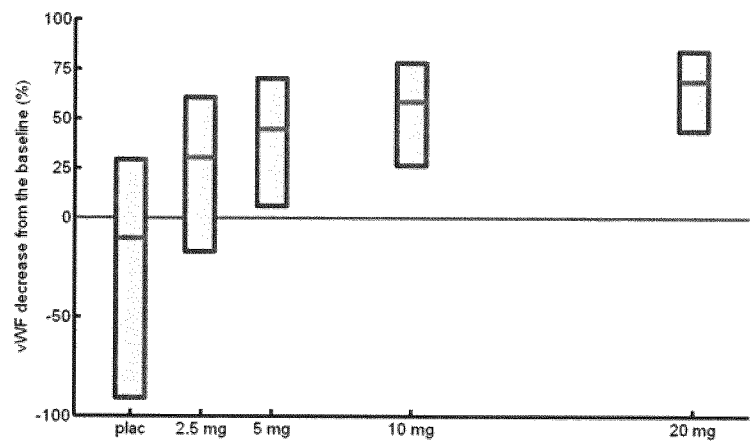

FIG. 5: vWF levels in TTP patients: Model-predicted % decrease from baseline of free vWF levels at the end of period 2 as a function of the daily dose level, including patients treated with placebo. Median, 25th and 75th percentiles are indicated.

Figure 6:
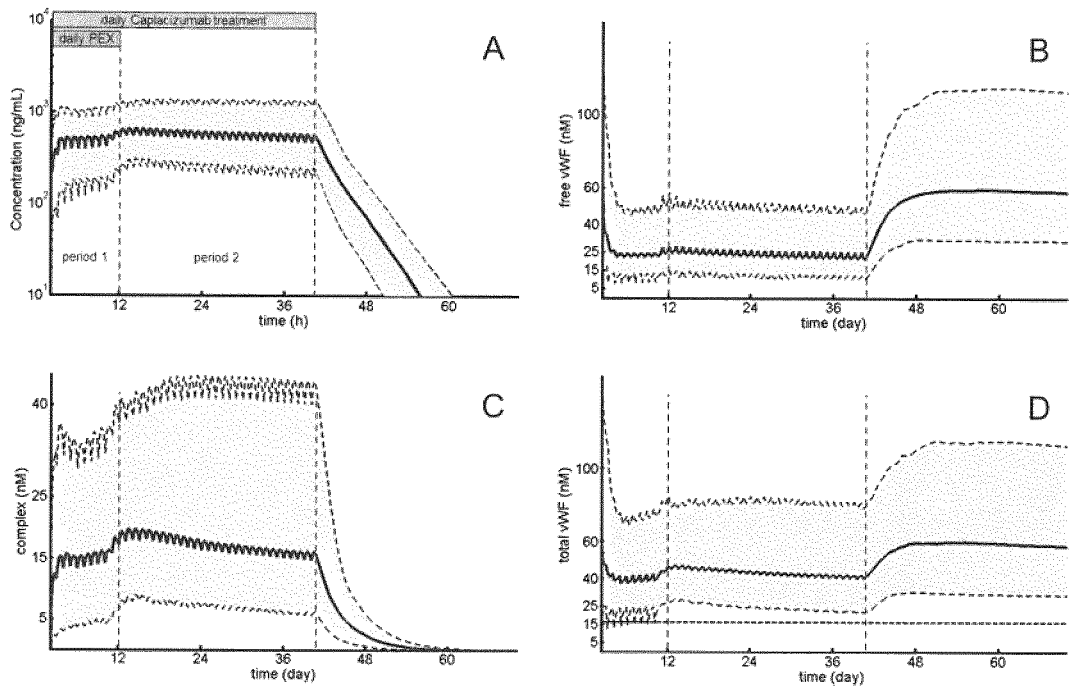

FIG. 6: PK/PD-Model of caplacizumab and free, total and complexed vWF: (A) Model-predicted caplacizumab concentration profiles after daily s.c. administration during period 1 and period 2 (with and without concomitant daily PE). (B) Model-predicted free vWF levels during a daily 10 mg s.c. administration of caplacizumab and after the treatment period. (C) Estimated complex caplacizumab-vWF levels during a daily 10 mg s.c. administration of caplacizumab and after the treatment period. (D) Model-predicted total vWF levels during a daily 10 mg s.c. administration of caplacizumab and after the treatment period. Median profiles, 5th and 95th percentiles are shown.

5. DETAILED DESCRIPTION

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 15%, more preferably within 10%, and most preferably within 5% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

The therapeutic potential of the polypeptides of the invention, such as ALX 0081, in a TTP setting was demonstrated by in vitro experiments using plasma from TTP patients in flow chamber experiments. In these experiments, endothelial cells were stimulated to produce ULvWF strings on their surface (see Example 7.2). It was demonstrated that the polypeptides of the invention, such as ALX 0081, were able to inhibit platelet-vWF interactions and particularly ULvWF mediated platelet interaction in vitro and were also shown to have no impact on ADAMTS13 function. In particular, it was demonstrated that the polypeptides of the invention, such as ALX 0081, are able to interact with vWF in both its active (i.e. functional for interaction with GPIb-IX-V as regular size multimers and as ultra-large multimers) and in its inactive stage (regular size multimers prior to conformational change of A1 domain). The study demonstrated a proof of concept that the polypeptides of the invention, such as ALX 0081, can be used to treat TTP patients. It also proves that the polypeptides of the invention, such as ALX 0081, do not interfere with the ADAMTS13 activity.

The present invention is at least partly based on the finding that the administration to human TTP patients of polypeptides comprising at least one ISVD against vWF (also referred to herein as "polypeptide(s) of the invention") provides an unexpected decrease of 2 days in the time-to-response. The time-to-response was objectified by the time necessary for the recovery of platelets to ≥150,000/μL. In addition, the invention provides an unexpectedly sustained and prolonged effect, reduced exacerbations, reduced hospitalization, reduced morbidity, a reduced number of required PEs, reduced ischaemia, reduced organ damage and reduced death toll.

Therefore, the invention relates to the use of the polypeptides of the invention to treat or ameliorate a vWF-related disease in a patient by an unexpectedly large decrease in the time-to-response, demonstrated by an accelerated platelet recovery. The invention also provides for less frequent PEs, while still maintaining the platelet recovery in the human patient at unexpectedly prolonged periods of time. Accordingly, methods are provided for decreasing the time-to-response in a human patient by administering to the patient a polypeptide of the invention, wherein the amount of the polypeptide administered is effective to change one or more disease markers of TTP, such as the number of platelets, thrombocytopenia, neurocognitive function, disintegrin-like and metalloprotease with thrombospondin repeats 13 (ADAMTS13) levels and anti-ADAMTS13 antibody titres, ADAMTS13 activity levels, cardiac marker (Troponin T or Troponin I), BNP (brain natriuretic peptide) or N-terminal pro brain natriuretic peptide (NT proBNP), and Brain damage markers (such as NSE (neuron specific enolase) and Sβ100 (S100beta)), preferentially an increase in the number of platelets.

In addition, the polypeptide of the invention when administered to a human TTP patient was safe as examined by safety laboratory markers, such as RICO, vWF and FVIII chromogene. Although there was a potential for an increased bleeding risk, this was wholly manageable.

The markers can be measured using standard methods known to and used by the skilled person, such as various immunologically based assays, including enzyme-linked immunosorbent assays (ELISA; also known as an enzyme immunoassay (EIA)), radioimmunoassays or immunoenzymetric assays. Chemical, colorimetric and enzymatic based assays also may be used when suitable.

Accordingly the present invention provides a polypeptide comprising at least one ISVD against vWF for use in treating a vWF-related disease in a human in need thereof, by administering to the human a 5-40 mg dose of said polypeptide, wherein said dose is followed within 15 min to 4 h by a first Plasma Exchange (PE).

The polypeptides of the invention were administered as adjunctive treatment at specific times relative to the PE procedures to treat or prevent (e.g., reduce or ameliorate one or more symptoms associated with) a vWF-related disease, e.g., TTP.

The term "treating" refers to administering a therapy in an amount, manner, and/or mode effective to improve a condition, symptom, or parameter associated with a disease or to prevent progression of a disease, to either a statistically significant degree or to a degree detectable to one skilled in the art. In the case of therapeutic use, the treatment may improve, cure, maintain, or decrease duration of, the disease or condition in the subject. In therapeutic uses, the subject may have a partial or full manifestation of the symptoms. In a typical case, treatment improves the disease or condition of the subject to an extent detectable by a physician, or prevents worsening of the disease or condition. For instance, the clinical features and signs in an acute episode of TTP as depicted in Table 1 or as provided in the TTP treatment guidelines (Scully et al. 2012 supra) improve. For instance, due to the treatment, the platelet count normalizes, the ADAMTS13 autoantibody titre decreases and/or the ADAMTS13 activity increases, all as known in the art and/or further detailed herein (cf. infra). An effective amount, manner, or mode can vary depending on the subject and may be tailored to the subject.

As used herein, the term "preventing" means to mitigate a symptom of the referenced disorder. In particular, said term encompasses the complete range of therapeutically positive effects of administrating a polypeptide of the invention to a subject including reduction of, alleviation of, and relief from, a vWF related disorder, e.g. TTP, and symptoms thereof. The term "prevention" includes the prevention or postponement of development of the disease, prevention or postponement of development of symptoms and/or a reduction in the severity of such symptoms that will or are expected to develop. These further include ameliorating existing symptoms, preventing additional symptoms and ameliorating or preventing the underlying causes of symptoms.

As used herein, the terms "subject" and "patient" are used interchangeably. As used herein, the terms "subject" and "subjects" refer to an animal, e.g., a mammal including a non-primate (e.g., a cow, pig, horse, donkey, goat, camel, cat, dog, guinea pig, rat, mouse, sheep) and a primate (e.g., a monkey, such as a cynomolgus monkey, gorilla chimpanzee and a human). A "patient" preferably refers to a human. Said patient can include elderly, adults, adolescents and children, from any age, for instance children ranging from the age of 2 years to less than 12 years, adolescents ranging from 12 years to less than 18 years, adults ranging from 18 years to less than 65 years, and elderly from 65 years and up.

Non-limiting examples of vWF-related diseases that can be treated include, but are not limited to, e.g. acute coronary syndrome (ACS), transient cerebral ischemic attack, unstable or stable angina pectoris, stroke, myocardial infarction, thrombotic thrombocytopenic purpura (TTP) and Upshaw-Schülman syndrome, preferably TTP.

The PE procedures to treat or prevent a vWF-related disease, such as e.g., TTP have been described in the Guidelines on the diagnosis and management of TTP and other thrombotic microangiopathies (Scully et al. 2012 supra), which is explicitly incorporated herein by reference. Complete remission is defined as normal platelet count, i.e. ≥150,000/µl, and optionally the absence of exacerbations (cf. Scully et al. 2012, supra).

As used herein the "time-to-response" is the time between the first treatment of a patient having an acute TTP episode and a platelet count of ≥150,000/µl, in which the first treatment is a PE or the administration of a polypeptide of the invention, or both, whichever is the earliest.

The term "Plasma exchange" ("PE") refers to a therapeutic procedure used to treat a variety of diseases, including TTP, through the bulk removal of plasma, i.e. a procedure in which a large volume of plasma is removed, usually 1-1.5 plasma volumes, which is replaced with a replacement fluid (Winters 2012 Hematology ASH Education Book 1:7-12). Through the bulk removal and replacement of plasma, PE removes pathologic substances such as auto antibodies against ADAMTS13 and ULvWF, but also some platelets. Plasma is used as a replacement fluid to replace ADAMTS13 when treating thrombotic thrombocytopenic purpura (McLeod Best Pract Res Clin Haematol. 2006; 19:157-167). The bulk removal and replacement of plasma also has implications for laboratory testing, making patient testing intricate.

Because PE involves the bulk removal of plasma, anything circulating in the plasma will be removed. Hence, this procedure is nonselective, removing both normal and pathologic plasma components, but also any medicaments to treat TTP administered before PE.

The person skilled in the art is well acquainted in determining the number of platelets. Platelet counts can be done by any method known in the art, such as manually using a hemocytometer or with an automated analyzer, e.g. electronic counting. Counts can also be estimated during blood smear examination. The microscopic method uses a phase contrast microscope to view blood on a hemacytometer slide. Electronic counting of platelets is the most common method. There are two types of electronic counting, voltage-pulse and electro-optical counting systems. For instance, the ADVIA hematology analyzer can be used for obtaining platelet counts and verify the obtained count by estimating counts on a Wright's-stained blood smear. The ADVIA measures platelets by flow cytometry based on principles of light scattering. For instance, platelets are identified by their size (<30 FL, low angle light scatter) and refractive index (n=1.35 to n=1.40 or high angle light scatter).

In various patients following an acute episode of TTP, the polypeptide of invention comprising at least one ISVD against vWF, e.g. ALX 0081, was administered after said patient had received a PE ("preceding PE"; a PE preceding the administration of the first dose of the polypeptide of the invention). It was observed that in the group of subjects which received a preceding PE (also indicated as "one PEX prior to randomization"), the median of the time-to-response was unexpectedly decreased by 2 days from 4.31 days for the Placebo arm to 2.44 days for the treatment arm: 43% reduction (Table 5; PEX prior to Randomization=YES).

Accordingly, the present invention relates to performing a PE (preceding PE) to a patient in need thereof, e.g. a patient with an acute episode of TTP, followed by a next PE within 24 h of said preceding PE, and administering a polypeptide of the invention ("first dose") about 8 h, 7 h, 6 h, 5 h, 4 h, 3 h, 3 h, 1 h, 45 min, 30 min, 20 min, 15 min, 10 min or even 5 min before starting said next PE, such as from 6 h to 15 min before starting said next PE (the "first PE"). In the present invention, the term "first dose" means the first administration of a polypeptide of the invention to a patient in need thereof, e.g. after an acute episode or every acute episode of TTP.

In an embodiment, an administration of the polypeptide of the invention to a patient, preferably a first dose is followed within 5 min to 8 h, such within 10 min to 6 h or 15 min to 4 h, for instance within 8 h, 7 h, 6 h, 5 h, 4 h, 3 h, 3 h, 1 h, 45 min, 30 min, 20 min, 15 min, 10 min or even 5 min by a PE.

In the present invention, the term "first PE" means the first PE performed after (or in some cases concurrent with) administration to a patient of a first dose of the polypeptide of the invention. The polypeptide of the invention can be administered or used for administration in the form of a liquid solution (e.g., injectable and infusible solutions). Such compositions can be administered by a parenteral mode (e.g., subcutaneous, intraperitoneal, or intramuscular injection), or by inhalation. The phrases "parenteral administration" and "administered parenterally" as used herein mean modes of administration other than enteral and topical administration, usually by injection, and include, subcutaneous (s.c.) or intramuscular administration, as well as intravenous (i.v.), intracapsular, intraorbital, intracardiac, intradermal, intraperitoneal, transtracheal, subcuticular, subcapsular, subarachnoid, intraspinal, epidural and intrasternal injection and infusion. Preferably the second or further doses of the polypeptides of the invention described herein are administered subcutaneously.

Preferably, the administration of the first dose of a polypeptide of the invention following an acute episode of TTP is an intravenous bolus injection, e.g. delivering the polypeptide through an intravenous line, administered all at once, over a period of a minute or two. Even more preferably, the administration of the first dose of a polypeptide of the invention following an acute episode of TTP is an intravenous push injection, e.g. delivering the polypeptide through an intravenous line, administered all at once, over a period of about 30 seconds or less.

It was surprisingly found that the polypeptides of the invention administered before PE (even without a preceding PE), in which time there is no direct pharmacological targeting of the active process of ULvWF-mediated platelet aggregation and it can be expected that said PE removes the polypeptide, were still able to reduce the median of the time-to-response by an unexpectedly large decrease of 2 days from 4.92 days for the Placebo arm to 3.00 days for the Caplacizumab arm: 39% reduction (Table 5: PEX prior to Randomization=NO).

The inventors considering that the polypeptide of the invention is safe to use as was demonstrated in previous studies in healthy volunteers and the present study with TTP patients (cf. Example 7.5.3), that TTP might be hard to diagnose, especially acute bouts of TTP, and that any time lost before starting a treatment results in adversities, concluded that this finding has the benefit that a treatment with the polypeptide of the invention can already be started timely, even before the patient enters a hospital, such as e.g. in an ambulance. Preferably, the polypeptide of the invention such as ALX 081 is administered by an intravenous push injection, since this can easily be performed outside hospitals, thus saving valuable time.

Accordingly, the present invention relates to administering to a patient in need thereof, such as e.g. patients with acute episodes (acute bouts) of TTP, a polypeptide of the invention about 8 h, 7 h, 6 h, 5 h, 4 h, 3 h, 3 h, 1 h, 45 min, 30 min, 20 min, 15 min, 10 min or even 5 min before starting PE, such as from 6 h to 15 min before starting PE ("first dose").

In an embodiment, the administration of a first dose of a polypeptide of the invention following an acute episode of TTP is followed by a PE ("first PE"). This first PE, whether or not preceded by a preceding PE, is followed by administration of a second or further dose of the polypeptide of the invention ("second dose" or "further dose"). Preferably, the second dose or further dose is administered within 120, 90 or 60 min, such as within 1-60 min, for instance, within 50, 45, 40, 35, 30, 25, 20, 15, 10, 5, 4, 3, 2 or even 1 min after the first PE. In some cases it may be advantageous to administer the second or further dose together or concurrently with the replacement fluid, e.g. the plasma of the PE.

In additional embodiments, a first dose, a second dose or further dose of the polypeptide of the invention is about 1, 2, 3, 4, 5, 6, 7, 8, 9, 10, 11, 12, 13, 14, 15, 16, 17, 18, 19, 20, 25, 30, 35, or 40, 50, 60, 70 or 80 mg, preferably 5-40 mg even more preferably 10 mg, which can be administered to a patient in need thereof, preferably per day. For administration to juvenile patients, such as e.g. children and adolescents, the dose may be adjusted to the weight of the patient. In particular embodiments the dose is about 0.01, 0.025, 0.05, 0.075, 0.1, 0.12, 0.14, 0.15, 0.16, 1.08, 0.2, 0.22, 0.24 or 0.25 mg/kg, preferably 0.143 mg/kg which corresponds to a 10 mg dose in a 70 kg adult.

In an embodiment, the present invention relates to the administration of about 5 to 40 mg, preferably 10 mg of a polypeptide of the invention, e.g. ALX 0081, within 1-60 min after a PE procedure, e.g. the first PE, the second PE or a further PE.

In an embodiment, the polypeptide of the invention, e.g. ALX 0081, is administered once per day or twice per day to a TTP patient in need thereof, preferably a patient with a platelet count below 100,000/µl plasma and/or a patient with an ADAMTS13 activity of ≤10% such as ≤5%:

In a further embodiment, a TTP patient in need thereof is treated with
(i) PE; and
(ii) a dose of 5-40 mg preferably 10 mg of said polypeptide 60 min to 1 min after said PE of step (i),
wherein step (i) and step (ii) are repeated once or twice per day until the platelet count of said patient is at least 50,000/µl plasma, such as 75,000, 100,000, 125,000 or even 150,000 per µl plasma.

In some cases it may be advantageous to repeat step (i) and step (ii) for a minimum of two days after complete remission (a platelet count of ≥150,000/µl plasma).

In an embodiment, 5-40 mg of the polypeptide of the invention is administered daily or twice daily for at least 5, 10, 15, 20, 25, 30, 60, 90 or even 120 days after the platelet count of said patient is ≥150.000/µl plasma, particularly when the ADAMTS13 activity of said patient is ≤10% such as ≤5%, or after the last PE.

When evaluating the data according to stratification (1 PEX prior to Randomization: YES & NO), an overall Hazard Ratio for the overall population aggregates to 2.197 with a p value=0.013. This Hazard Ratio means that at any time, subjects receiving the polypeptide of the invention have more than twice the rate of achieving the primary endpoint of confirmed platelet recovery in comparison to subjects on Placebo. In addition, this platelet recovery is achieved 2 days faster in the treatment group.

Hence, the administration of polypeptides comprising at least one ISVD against vWF, such as ALX 0081, to human TTP patients following an acute episode of TTP provides an unexpected decrease in the time-to-response, independent of the order of administration of said polypeptide and said PE, e.g. whether the PE is performed before or after the administration of the first dose of the polypeptide of the invention.

It was further surprisingly found that the number of exacerbations decreased from 11 in the Placebo group to 3 in the Caplacizumab group. Hence, there are 3 times more exacerbations in the placebo group (i.e. TTP patients receiving PE and a placebo instead of the polypeptide of the invention) compared to the treatment group (i.e. TTP patients receiving PE and the polypeptide of the invention; also indicated as Caplacizumab group). The term "exacerbation" as used herein refers to a recurrent thrombocytopenia following a confirmed platelet response and requiring a re-initiation of daily PE treatment after 1 day but ≤30 days after the last PE.

This indicates that the polypeptide of the invention, such as ALX 0081, can be solely responsible for treating and/or alleviating (the symptoms of) TTP.

Accordingly, the present invention relates to a polypeptide comprising at least one ISVD against vWF, such as ALX 0081, for use in treating a vWF-related disease, such as TTP, in a human in need thereof, by administering to the human a dose of 1-80 mg or 5-40 mg, such as 1, 2, 3, 4, 5, 6, 7, 8, 9, 10, 11, 12, 13, 14, 15, 16, 17, 18, 19, 20, 25, 30, 35, 40, 50, 60, 70 or 80 mg, preferably 10 mg of said polypeptide.

Based on this surprising observation, a further optimized treatment protocol was designed by the present inventors, in essence based on the idea that the distribution of confirmed platelet response time is shorter and not skewed and biased to the right (longer time to response) in the CAP arm in comparison to the placebo arm. In the further optimized treatment protocol, all subjects are treated with a fixed PE treatment period, which is set for 3-5 days, such as 3 days or 4 days or 5 days, preferably 3 days. In this case, the PE treatment period can be independent of the recovery of platelets (≥150,000/µl). In the further optimized treatment protocol, the burden for the patient and the costs are decreased.

Accordingly, the present invention relates to a polypeptide comprising at least one ISVD against vWF, such as ALX 0081, for use in treating a vWF-related disease in a human in need thereof, comprising: (i) performing a PE; and (ii) administering a dose of 5-40 mg, such as 10 mg of the polypeptide of the invention 15 min to 4 h after said PE of step (i), wherein step (i) and step (ii) are repeated once per day for 3-5 days, such as 3 days, 4 days or 5 days, preferably 3 days; followed by further comprising administering once per day a dose of 5-40 mg, such as 10 mg of said polypeptide for at least 10 days, such as at least 20 days or at least 30 days and/or for at least 10 days, such as at least 20 days or at least 30 days after the platelet count of said patient was for the first time ≥150.000/µl.

In the present study, for up to one year TTP patients have been followed-up for remission. The term "remission" as used herein refers to as confirmed platelet response and the absence of exacerbation. The term "confirmed platelet response" as used herein refers to the time-to-response of treatment as defined by a recovery of platelets ≥150,000/μL, which response must be confirmed at 48 hours after the initial reporting of platelet recovery above 150,000/μL by a de novo measure of platelets ≥150,000/μL, and preferably LDH ≤2×ULN.

As demonstrated in herein (Example 7.5.5; Table 8), overall, 29 patients in the treatment group went into remission, compared to 18 patients in the placebo group. Hence, the treatment arm presents 1.6× more subjects with complete remission versus the Placebo arm.

As noted above, the platelet count is the primary means for assessing remission. Measurement of ADAMTS13 activity in patients with a history of classical TTP is important because low levels have been shown to be predictive of relapse. However, it is unclear at present (and the data is conflicting) as to whether the titre of an inhibitory antibody to ADAMTS13 is significant i.e. are those individuals with a high titre anti-ADAMTS13 antibody more likely to relapse than those with a low titre. The person skilled in the art appreciates that current tests of ADAMTS13 are performed under static conditions and do not always accurately reflect the physiological changes that occur in vivo (http://practical-haemostasis.com/Miscellaneous/Miscellaneous%20Tests/adamts13_assays.html).

The present inventors now unexpectedly observed that remission appears more pronounced for the subgroup of subjects with low Baseline ADAMTS13 activity (i.e. less than 10%, such as less than 5%), when starting treatment, e.g. administering the first dose, of the polypeptide of the invention, such as ALX 0081 (cf. Example 7.5.8).

Accordingly, the present invention relates to a polypeptide comprising at least one ISVD against vWF for use in treating a vWF-related disease in a human in need thereof, by administering to said human a first dose of 1-40 mg, preferably 10 mg of said polypeptide, until the platelet count of said human is ≥150000/μl. In a preferred aspect, said human has an ADAMTS13 activity of less than 10%, such as less than 5% when administering said polypeptide.

In the present study, for up to one year TTP patients have been followed-up for relapses. The term "relapse" as used herein refers to a de novo event of TTP that occurs later than 30 days after the last daily PE, e.g. 0-2 days after the TTP patient showed complete remission. The "later than 30 days" date coincides with the last administration of the polypeptide of the invention in the present study.

Although the polypeptide of the invention was not administered anymore, it has been found that the number of relapses in the Caplacizumab group equaled the number of relapses in the Placebo group (see Table 7, in Example 7.5.4).

The inventors observed that in both treatment arms, relapses are more prominent in patients with a baseline ADAMTS13 activity of <10%, such as <5%, even though the ADAMTS13 activity was only available in a subset of the patients. The inventors hypothesized (without being bound to any theory) that this may indicate that patients with baseline ADAMTS13 activity of <10%, such as <5% are more prone to relapses (or exacerbations), when stopping administration of the polypeptide of the invention, such as ALX 0081.

In particular, the data support the use of ADAMTS13 activity as predictive marker for recurrences of UP and its potential for treatment decisions. ADAMTS13 activity is able to predict relapses which occur shortly after stopping caplacizumab treatment. These relapses are considered as relapses of the presenting TTP episode (unresolved disease activity, based on continuously low ADAMTS13 activity). A 30-day treatment period (post PE) with caplacizumab has demonstrated a significant impact on the number of exacerbations. Hence, extending the caplacizumab treatment period for those patients at risk for relapse (i.e. with underlying disease activity based on ADAMTS13 activity) will maintain the protective effects of caplacizumab until the underlying disease is adequately treated and resolved. Conversely, precautionary treatment with caplacizumab will reduce the risk of a—new—acute episode of TTP.

Hence, treatment with polypeptide of the invention, such as ALX 0081, should be continued for longer periods compared to patients with higher activity. The polypeptide of the invention should be administered to a TTP patient to reduce the risk of and/or prevent the chance of relapse(s) until the ADAMTS13 activity was at least 10%, such at least 15%, 20%, 25%, 30%, 35%, 40%, 45%, or even 50% compared to the normal or reference activity.

Accordingly, the present invention relates to a polypeptide comprising at least one immunoglobulin single variable domain (ISVD) against von Willebrand Factor (vWF) for use in reducing the risk of and/or preventing an acute episode of a vWF-related disease, e.g. TTP, in a human in need thereof, comprising a step (i): administering to said human a dose of 5-40 mg, preferably 10 mg, of said polypeptide. Preferably, said risk is reduced by a factor of at least 1.2, 1.3, 1.4, 1.5, 1.6, 1.75, 1.8, 2 or more, such as 3, 4, 5, 6, 7, 8, 9, or even 10, or even more such as 20, 50 or even 100. Preferably said risk is reduced by 10% or even more such as 20%, 30%, 40%, 50%, 60% or more, such as 80% or even 100%.

Accordingly, the present invention relates to a polypeptide as described herein, wherein said step (i) of administering to said human said polypeptide is repeated for at least 1, 2, 3, 4, 5, 6, 7, 8, 9, or 10 times, or even more than 10 times, such as 20 times, preferably more than 30 times or even more.

The method according to claim 1, wherein said step (i) of administering to said human said polypeptide is repeated for at least 1, 2, 3, 4, 5, 6, 7, 8, 9, or 10 days, or even more than 10 days, such as 20 days, preferably more than 30 days, such as 2 months, 3 months, 4 months, 5 months, 6 months or even more.

Accordingly, the present invention relates to a polypeptide as described herein, wherein said dose is administered 1 time per day or two times per day.

Accordingly, the present invention relates to a polypeptide as described herein, further comprising
(ii) measuring the ADAMTS13 activity of said patient;
(iii) comparing said ADAMTS13 activity with a reference ADAMTS13 activity; and
(iv) if said ADAMTS13 activity is lower than 30%, such as 20%, 15%, 10% or 5% of said reference ADAMTS13 activity, then repeating said step (i) of administering to said human said polypeptide.

Accordingly, the present invention relates to a polypeptide as described herein, wherein said ADAMTS13 activity of said patient is measured every day, or every 2, 3, 4, 5, 6, 7, 8, 9, or 10 days, preferably at least once every week.

Accordingly, the present invention relates to a polypeptide as described herein, wherein step (i) is repeated until said ADAMTS13 activity is at least 5%, 10%, 15%, such 20%, or even 30% or higher of said reference ADAMTS13 activity.

Accordingly, the present invention relates to a polypeptide as described herein, wherein step (i) of administering to said human said polypeptide is repeated until said ADAMTS13 activity is at least 5%, 10%, 15%, such as 20% or 30% of said reference ADAMTS13 activity on at least 2 consecutive measurements. Preferably, said 2 consecutive measurements are at least 24 h, more preferably 48 h apart, such as at least 3 days apart, or even more such as, 4, 5, 6, or even 7 days apart, preferably a week apart.

Accordingly, the present invention relates to a polypeptide as described herein, wherein said step (i) of administering to said human said polypeptide is repeated for at least at least 1, 2, 3, 4, 5, 6, 7, 8, 9, or 10 days, or even more than 10 days, such as 20 days, preferably more than 30 days or even more, after said ADAMTS13 activity is at least 5%, at least 10%, at least 15%, such as 20% or at least 30% of said reference activity on at least 2 consecutive measurements.

Accordingly, the present invention relates to a polypeptide comprising at least one immunoglobulin single variable domain (ISVD) against von Willebrand Factor (vWF) for use in reducing the risk of and/or preventing an acute episode of a vWF-related disease, such as TTP, in a human in need thereof, comprising step (i): administering to said human a dose of 5-40 mg, preferably 10 mg of said polypeptide, further comprising
    measuring the ADAMTS13 activity of said patient;
    comparing said ADAMTS13 activity with a reference ADAMTS13 activity; and
    if said ADAMTS13 activity is ≥5%, such as ≥10%, or even ≥15%, or more than 20% or 30% of said reference ADAMTS13 activity, then repeating said step (i) for at most 30 days, such as at most 20 days, or even 15, 10, 9, 8, 7, 6, 5, 4, 3, 2 days or even 1 day.

Accordingly, the present invention relates to a polypeptide comprising at least one immunoglobulin single variable domain (ISVD) against von Willebrand Factor (vWF) for use in reducing the risk of and/or preventing an acute episode of a vWF-related disease, such as TTP, in a human in need thereof, comprising at least the following steps;
(i) measuring the ADAMTS13 activity of said patient;
(ii) comparing said ADAMTS13 activity with a reference ADAMTS13 activity; and
(iii) if said ADAMTS13 activity is lower than 30%, 20%, 15%, 10% or 5% of said reference activity, then administering to said human a dose of 5-40 mg, preferably 10 mg of said polypeptide comprising at least one immunoglobulin single variable domain (ISVD) against von Willebrand Factor (vWF).

As used herein, reducing risk or incidence includes decreasing the probability or incidence of an indication, symptom or result of vWF-related disease, such as TTP, for a subject compared to a relevant, e.g. untreated, control population, or in the same subject prior to treatment according to the invention.

An indication, symptom or result of a vWF-related disease, such as TTP, as used herein includes organ damage, ischaemic damage, microthrombi formation, exacerbations, mortality, relapses, one or more disease markers of a vWF related disease, such as TTP, include the number of platelets, thrombocytopenia, neurocognitive function, ADAMTS13 levels and anti-ADAMTS13 antibody titres, ADAMTS13 activity levels, cardiac marker (Troponin T or Troponin I), BNP (brain natriuretic peptide) or N-terminal pro brain natriuretic peptide (NT proBNP), creatinine, and Brain damage markers (such as NSE (neuron specific enolase) and Sβ100 (S100beta)), preferentially organ damage markers, such as LDH levels, troponin T and/or troponin I levels, and/or creatinine levels.

The reduced risk or incidence can include delaying or preventing the onset of an indication, symptom or result of vWF-related disease, such as TTP. Risk or incidence can also be reduced if the severity of an indication, symptom or result of vWF-related disease, such as TTP, is reduced to a level such that it is not of clinical relevance. That is, the indication, symptom or result of a vWF-related disease, such as TTP, may be present but at a level that does not endanger the life, activities, and/or wellbeing of the subject. In some circumstances the occurrence of the vWF-related disease, such as UP, is reduced to the extent that the subject does not present any signs of the vWF-related disease, such as TTP, during and/or after the treatment period.

It will be appreciated that no actual proof of reduced risk for an individual can be obtained because if treatment is provided then it cannot be said whether an indication, symptom or result of a vWF-related disease, such as TTP, would have occurred, or would have occurred sooner in the absence of such treatment. Thus, the concept of risk and, increased or reduced risk refer to statistical values only. Further, reduction of risk of an indication, symptom or result of a vWF-related disease, such as TTP, can be reflected in a reduction in the severity of an indication, symptom or result of a vWF-related disease, such as TTP, as well as in the absence of observation or delay in observation of an indication, symptom or result of a vWF-related disease, such as TTP.

It will be appreciated that the polypeptide of the invention reduces the risk of and/or preventing an acute episode of a vWF-related disease, such as TTP. Hence, the indication, symptom or result of a vWF-related disease, such as TTP, is also reduced. Given the pathophysiology of acquired TTP whereby ULvWF strings consume platelets in the formation of microthrombi, it was reasoned that the recovery of platelet counts is an indirect measure of prevention of further microthrombi formation. The morbidity and the acute mortality associated with acquired TTP is a result of these microthrombi.

Indeed, this reasoning is supported by the normalization of organ damage markers. In particular, the results indicate that the organ damage markers, such as troponin I and T, LDH and creatinine, return faster to normal levels in subjects receiving the polypeptide of the invention, e.g. ALX 0081, than in subjects receiving placebo (cf. Example 7.5.7).

Hence, the results suggest that a faster normalization rate of these organ damage markers is linked to a better clinical outcome, i.e. a reduced risk of and less organ damage due to organ ischemia caused by microthrombi.

Accordingly, the present invention relates to a method as described herein, wherein
    the risk of organ damage, ischaemic damage and/or microthrombi formation is reduced by 10%, 20%, 30%, preferably by at least 40%, or even at least 50%, such as 60%, 70%, 80%, 90% or even to 100% (e.g. absence of organ damage, ischaemic damage and/or microthrombi formation due to the vWF-related disease);
    the risk of organ damage, ischaemic damage and/or microthrombi formation is reduced by a factor 1.2, 1.3, 1.4, 1.5, 1.6, 1.75, 1.8, 2 or more, such as 3, 4, 5, 6, 7, 8, 9, or even 10, or even more such as 20, 50 or even 100;
    organ damage, ischaemic damage and/or microthrombi formation is reduced preferably by at least 10%, 20%, 30%, 40%, or even at least 50%, such as 60%, 70%, 80%, 90% or even to 100%;
    organ damage, ischaemic damage and/or microthrombi formation is reduced by a factor 1.2, 1.3, 1.4, 1.5, 1.6, 1.75, 1.8, 2 or more, such as 3, 4, 5, 6, 7, 8, 9, or even 10, or even more such as 20, 50 or even 100;

organ damage markers, such as LDH levels, troponin T, troponin I levels, and/or creatinine levels, return to at least 40%, or even at least 50%, such as 60%, 70%, 80%, 90% or even to 100% of normal levels;

organ damage markers, such as LDH levels, troponin T, troponin I levels, and/or creatinine levels, improve by at least 20%, such 30% or even higher, such as 40%, or even at least 50%, such as 60%, 70%, 80%, 90% or even to 100% of normal levels. Preferably, said organ damage, such as LDH levels, troponin T, troponin I levels, and/or creatinine levels, markers improve in less than 30 days of treatment, preferably, in less than 20 days of treatment, such as, less than 15, 10, 9, 8, 7, 6, 5, 4, 3, 2 days or even within 1 day.

the number of platelets is kept at ≥150000/µl.

the time to platelet normalization (≥150000/µl) is reduced by at least 10%, 20%, 30%, 35%, 39%, preferably by at least 40%, or even at least 50%, such as 60%, 70%, 80%.

the risk of exacerbations is reduced by at least 10%, 20%, 30%, 40%, or even at least 50%4, such as 60%, 70%, 80%, 90% or even to 100%;

the risk of exacerbations is reduced by a factor, 2 or ore such as 3, 4, 5, 6, 7, 8, 9, or even 10, or even more such as 20, 50 or even 100;

mortality due to said vWF related disease is reduced by 10%, 20%, 30%, preferably by at east 40%, or even at least 50%, such as 60%, 70%, 80%, 90% or even to 100%;

mortality due to said vWF related disease is reduced by a factor, 2 or more, such as 3, 4, 5, 6, 7, 8, 9, or even 10, or even more such as 20, 50 or even 100; and/or remission is increased by a factor 1.2, 1.3, 1.4, 1.5, 1.6, 1.75, 1.8, 2 or more, such as 3, 4, 5, 6, 7, 8, 9 or even 10, or even more such as 20, 50 or even 100.

The term "reference activity" as used herein, refers to the average ADAMTS13 activity of 5 healthy subjects in the assay performed, which is set at 100%. For instance, in a FRETS-vWF73 assay, the calibration curve generated using a normal human plasma pool, in which the slope of the regression curve is calculated for each calibration sample, and used to generate the calibration curve (trend line: y=ax+b; with x=ADAMTS13 (%) and y=delta RFU/delta time). The ADAMTS13 activity (%) of a sample is then calculated as: (y−b)×1/a. Indeed, in general the patients that relapsed had a lower ADAMTS13 activity than the patients who did not relapse.

Accordingly, the present invention relates to a polypeptide for reducing the risk of and/or preventing ischaemic damage, organ damage and/or microthrombi formation, for instance causable by a vWF-related disease, such as TTP, in a human in need thereof, comprising at least the following step (i) administering to said human a dose of 5-40 mg/day, preferably 10 mg/day of a polypeptide comprising at least one immunoglobulin single variable domain (ISVD) against von Willebrand Factor (vWF); wherein administration of said polypeptide reduces the risk of and/or prevents ischaemic damage, organ damage and/or microthrombi formation by at least 10%, 20%, 30%, preferably by at least 40%, or even at least 50%, such as 60%, 70%, 80%, 90% or even to 100%. Preferably, administration of said polypeptide reduces the risk of and/or prevents ischaemic damage, organ damage and/or microthrombi formation by a factor 1.2, 1.3, 1.4, 1.5, 1.6, 1.75, 1.8, 2 or more, such as 3, 4, 5, 6, 7, 8, 9, or even 10, or even more such as 20, 50 or even 100.

Accordingly, the present invention relates to a polypeptide for reducing the risk of and/or preventing ischaemic damage, organ damage and/or microthrombi formation as described herein, wherein said step (i) of administrating said polypeptide is repeated for at least 1, 2, 3, 4, 5, 6, 7 days, or even longer such as 1 week, 2 weeks, 3 weeks, or even longer such as 1 month or even 2 months.

Accordingly, the present invention relates to a polypeptide for reducing the risk of and/or preventing ischaemic damage, organ damage and/or microthrombi formation as described herein, further comprising measuring ADAMTS13 activity of said patient, preferably once per week.

Accordingly, the present invention relates to a polypeptide for reducing the risk of and/or preventing ischaemic damage, organ damage and/or microthrombi formation as described herein, wherein said step (i) of administrating said polypeptide is repeated for at least 1, 2, 3, 4, 5, 6, 7 days, or even longer such as 1 week, 2 weeks, 3 weeks, or even longer such as 1 month or even 2 months when the ADAMTS13 activity is [for the first time] ≥5%, such as ≥10%, or even ≥15% of a reference ADAMTS13 activity.

Accordingly, the present invention relates to a polypeptide of the invention for treating a symptom of a vWF-related disease, such as TTP, in a human suffering from said disease, comprising administering to the subject a polypeptide of the invention, in an amount effective to treat the symptom of a vWF-related disease in a human suffering from said disease.

Accordingly, the present invention relates to a polypeptide of the invention for inhibiting in a human the onset or progression of a vWF-related disease, such as TTP, the inhibition of which is effected by binding of a polypeptide comprising at least one immunoglobulin single variable domain (ISVD) against von Willebrand Factor (vWF) to vWF, comprising administering to the human at a predefined interval effective inhibitory doses of said polypeptide, wherein each administration of the antibody delivers to the human from 0.1 mg per kg to 25 mg per kg of the human's body weight, so as to thereby inhibit the onset or progression of the disease in the human.

Accordingly, the present invention relates to a polypeptide for reducing the likelihood of a human contracting ischaemic organ damage by a vWF-related disease, which comprises administering to the human at a predefined dose a polypeptide comprising at least one immunoglobulin single variable domain (ISVD) against von Willebrand Factor (vWF), wherein each administration of the antibody delivers to the human from 0.1 mg per kg to 25 mg per kg of the human's body weight, so as to thereby reduce the likelihood of the human contracting ischaemic organ damage.

Modeling based on these results indicates that maintaining administering polypeptides for prolonged times of the invention would be efficacious in preventing acute episodes. This advantageous profile results in a decreased health hazard. Hence, it can be concluded that the polypeptide of the invention prevents relapses.

Accordingly, the present invention relates to administering the polypeptide of the invention every 1, 2, 3, 4, 5, 6 7 days or even 2, 4, 6, or 8 weeks at doses ranging from 1-80 mg, such as 5-40 mg, preferably in preventing acute episodes of TTP, Particular efficacious doses are 10-20 mg. In particular embodiments, the dose comprises about 1, 2, 3, 4, 5, 6, 7, 8, 9, 10, 11, 12, 13, 14, 15, 16, 17, 18, 19, 20, 25, 30, 35, 40, 50, 60, 70 or 80 mg, preferably 10 mg of a polypeptide comprising at least one ISVD against vWF, such as ALX 0081.

In an embodiment the present invention relates to a method of preventing relapse in a TTP patient, comprising
(1) measuring ADAMTS13 activity from a TTP patient by an assay, such as a direct or an indirect assay;
(2) comparing said activity of step (1) with a reference value (normal value); and
(3) if the ADAMTS13 activity of step (1) is less than 15%, such as less than 10% and less than 5%, of the reference value, then administering the polypeptide of the invention, e.g. ALX 0081,
thereby preventing relapse.

Preliminary results suggest that administration of the first dose of the polypeptide of the invention before the first PE already results in an increase in the number of platelets.

Accordingly, the present invention relates to administering the polypeptide of the invention in a patient in need thereof, such as e.g. a patient experiencing an acute episode of TTP, a dose of about 1, 2, 3, 4, 5, 6, 7, 8, 9, 10, 11, 12, 13, 14, 15, 16, 17, 18, 19, 20, 25, 30, 35, 40, 50, 60, 70 or 80 mg, preferably 10 mg of a polypeptide comprising at least one ISVD against vWF, such as ALX 0081.

The polypeptides of invention comprising at least one ISVD against vWF, e.g. ALX 0081, can be administered to a subject (e.g., a human subject) alone or combination with a second agent, e.g., a second therapeutically or pharmacologically active agent, to treat or prevent (e.g., reduce or ameliorate one or more symptoms associated with) a vWF-related disease, e.g., TTP.

Non-limiting examples of agents that can be co-formulated with the polypeptides of invention comprising at least one ISVD against vWF, e.g. ALX 0081, include, for example, adjunctive immunosuppressive treatment (e.g. corticosteroids such as (methyl)prednisolone or (methyl)prednisone; or rituximab), antiplatelet agents (e.g. aspirin), supportive therapy with red cell transfusion or folate supplementation, treatment with vincristine or cyclosporin, anti-autoADAMTS13 antibodies, or ADAMTS13. Such combination therapies may advantageously utilize lower dosages of the administered therapeutic agents, thus avoiding possible toxicities or complications associated with the various monotherapies.

In an embodiment, the present invention relates to a combination therapy of the polypeptide of the invention together with an immunosuppressive treatment, in particular rituximab, which efficiently prevents relapses in TTP patients. Preferably, the combination therapy is provided until the ADAMTS13 activity is at least ≥5%, such as ≥10%, >15%, >20%, 25%, 30%, 35%, 40%, 45% or even normalised such as ≥50% of the normal activity, TTP remains a diagnosis based on clinical history, examination of the patient and the blood film. ADAMTS13 assays help to confirm the diagnosis and monitor the course of the disease and possible need for additional treatments. Acute episodes of TTP can be diagnosed according to Table 1 and the guidelines of, for instance, Scully et al. (2012 supra)

TABLE 1

| Clinical features and signs in acute episode of TTP. | |
| --- | --- |
| Thrombocytopenia | Epistaxis, bruising, petechiae, gingival bleeding, haematuria, menorrhagia, gastrointestinal bleeding, retinal haemorrhage and haemoptysis |
| Central neurological—often flitting and variable 70-80% | Confusion, headache, paresis, aphasia, dysarthria, visual problems, encephalopathy, coma ( 10%) |
| Fever (>37.5° C.) | |
| Non-specific symptoms | Pallor, jaundice, fatigue, arthralgia or myalgia |
| Jaundice | Resulting from microangiopathic haemolytic anaemia |
| Renal Impairment | Proteinuria, microhaematuria |
| Cardiac | Chest pain, heart failure, hypotension |
| Gastro-intestinal tract | Abdominal pain |

The efficacy of any particular polypeptide of the invention or dosing regimen may be determined by methods available to those of skill in the art. Briefly, during a clinical trial, the patients may be observed by medical personnel and the state of disease is assessed by any combination of criteria. The improvement of a patient's disease state is determined based on these criteria at numerous time points and the combination of these determinations on a patient population is plotted to assess the efficacy of treatment.

In exemplary embodiments, assessment of efficacy may be measured by any or all of the criteria set forth below:

Time-to-response of treatment, defined by a recovery of platelets ≥150,000/µL. This response must be confirmed at 48 hours after the initial reporting of platelet recovery above 150,000/µL by a de novo measure of platelets ≥150,000/µL and preferably by LDH ≤2×ULN Number of subjects with complete remission Number of (subjects with) exacerbations of TTP and time to first exacerbation of TTP. Exacerbation is defined as recurrent thrombocytopenia following a response and requiring a re-initiation of daily PE treatment after ≥1 day but ≤30 days after the last daily PE.

Number of subjects relapsing of TTP (defined as de novo event of TTP that occurs later than 30 days after the last daily PE) for a maximum of 1 year, and time to first relapse of TTP Daily PE data, including serious adverse events (SAEs) related to daily PE treatment Neurocognitive function, as measured by a neurocognitive test battery, at complete remission and at 1 year follow up. This test will be preceded by the Glasgow Coma Score to measure the state of consciousness of the subject Improvement of organ dysfunction and improvement of TTP related signs and symptoms Total mortality within the daily PE treatment period and within the subsequent study drug treatment period (including tapering)

Determination of biomarkers of TTP including but not limited to a disintegrin-like and metalloprotease with thrombospondin repeats 13 (ADAMTS13) levels and anti-ADAMTS13 antibody titres.

The person skilled in the art is familiar to determine the efficacies.

For instance, ADAMTS13 activity can be evaluated using electrophoresis of vWF multimers to detect ultra-large multimers uncleaved by the protease (Moake et al. (1982) The New England journal of medicine 307, 1432-1435; Furlan, et al. (1997) Blood 89, 3097-3103 7, 8). ADAMTS13 activity can be tested employing FRETS-vWF73, a fragment of vWF chemically modified to emit fluorescence when cleaved by ADAMTS13. In the assay, FRETS-vWF73 is added to a sample of the patient's plasma, and the change in fluorescence is measured over time to determine ADAMTS13 activity. If an inhibitor is present, it is frequently a neutralizing IgG antibody directed against ADAMTS13, which can be measured by ELISA (Kokame et al. (2005) British journal of haematology 129, 93-100). Alternatively or in addition, ADAMTS13 activity can be determined as described in for instance Vesely et al. (2003, supra), Fontana et al. (2004, supra) or Remuzzi et al. (Blood 2002; 100: 778-7852002). For instance, indirect ADAMTS13 activity assays involve the detection of cleavage of products either of a full-length VWF molecule or a VWF fragment that encompasses the ADAMTS13 cleavage site in the A2 domain of VWF. (1) Collagen Binding Assays. Normal plasma or purified VWF is incubated with the test plasma sample in the presence of BaCl2 and 1.5M urea which denatures the VWF. VWF is cleaved by ADAMTS13 and residual VWF is measured by its binding to collagen Type III. The bound VWF is quantitated using an ELISA assay with a conjugated anti-VWF antibody. (2) Ristocetin-Induced Aggregation. This is similar to the collagen-binding assay above but residual VWF is measured by ristocetin-induced platelet aggregation using a platelet aggregometer. (3) Functional ELISA assays. In this assay, a recombinant VWF fragment is immobilised onto an ELISA plate using an antibody to a tag on the VWF. The VWF fragment encodes the A2 domain and the ADAMTS13 cleavage site at Tyr1605-Met1606 and is tagged with S-transferase [GST]-histidine [GST-VWF73-His]. Plasma is added to the immobilised GST-VWF73-His fragment and cleavage of the immobilised fragment occurs at the ADAMTS13 cleavage site. The residual, cleaved VWF fragment is measured by using a second monoclonal antibody that recognises only the cleaved VWF fragment and not the interact fragment. ADAMTS13 activity is, therefore, inversely proportional to the residual substrate concentration. This method forms the basis for the TECHNOZYM® ADAMTS13 Activity ELISA.

The person skilled in the art is familiar in determining autoantibodies against ADAMTS13, for instance, anti-ADAMTS13 autoantibodies can be determined by ELISA, such as the TECHNOZYM® ADAMTS13 INH ELISA (Technoclone).

The person skilled in the art is familiar in determining of Ristocetin Cofactor activity in human samples, for instance, the Ristocetin Cofactor can be determined by the vW Select of Bio/Data corp. on an aggregometer PAP-8E analyzer (Bio/Data corp.).

The person skilled in the art is familiar in determining Factor VIII in human samples, for instance using Coamatic Factor VIII (Chromogenix) on a STA-R evolution analyzer (Diagnostica Stago).

The person skilled in the art is familiar in determining von Willebrand Factor antigen in human samples, for instance using a immunoturbidometric assay (e.g. using a STA Lia test vWF:Ag) on a STA-R evolution analyzer (Diagnostica Stago).

The person skilled in the art is familiar in determining LDH levels. Most methods are based on a lactate dehydrogenase-based enzymatic analysis on a spectrophotometer. A convenient review is provided by Medbø et al. (2000) "Examination of four different instruments for measuring blood lactate concentration". Scand J Clin Lab Invest 60:367-380. Various companies provide assays, such as Abnova (Catalog Number KA1653) which measures the catalysis by LDH of the interconversion of lactate and pyruvate, i.e. a non-radioactive colorimetric LDH assay based on the reduction of the tetrazolium salt MTT in a NADH-coupled enzymatic reaction to a reduced form of MTT which exhibits an absorption maximum at 565 nm. The intensity of the purple color formed is directly proportional to the enzyme activity. Similarly, in the Sigma Aldrich kit (MAK066-1KT), LDH reduces NAD to NADH, which is specifically detected by colorimetric (450 nm) assay. Normal values are provided in the Table 1.1 below.

The person skilled in the art is familiar in determining troponin I and T. In general, troponin T and I are measured by immunoassay methods, which are available on many different immunoassay platforms, e.g. DPC Immulite, Abbott AxSYM, Bayer ACS:Centaur, Ortho Vitros, Roche Elecsys, third generation. A convenient review is provided by Wu et al. (1999) National Academy of Clinical Biochemistry Standards of Laboratory Practice: recommendations for the use of cardiac markers in coronary artery diseases. Clin Chem. July 1999; 45(7):1104-21. Normal values are provided in the Table 1.1 below.

The person skilled in the art is familiar in determining creatinine. A convenient review is provided by Peake and Whiting "Measurement of Serum Creatinine—Current Status and Future Goals" Clin Biochem Rev. 2006 November; 27(4): 173-184. For instance, creatinine levels can be determined by Abcam Creatinine Assay Kit (ab65340) or Bio-Vision's Creatinine Assay Kit. In the assay, creatinine is converted to creatine by creatininase, creatine is converted to sarcosine, which is specifically oxidized to produce a product which reacts with a probe to generate red color ($\lambda$max=570 nm) and fluorescence (Ex/Em=538/587 nm). Normal values are provided in the Table 1.1 below. Since the amount of creatinine in the blood increases with muscle mass, men usually have higher creatinine levels than do women.

TABLE 1.1

| Test | Specimen | Conventional Units | SI Units |
| --- | --- | --- | --- |
| | normal values | | |
| Creatinine | Serum | 0.7-1.3 mg/dL | 61.9-115 µmol/L |
| Lactate dehydrogenase (LDH) | Serum | 60-160 U/L | 1-1.67 µkat/L |
| Troponin I | Plasma | <0.1 ng/mL | <0.1 µg/L |
| Troponin T | Serum | ≤0.03 ng/mL | ≤0.03 µg/L |

It will be appreciated that the normal values provided in Table 1.1 can vary from lab to lab, between men and women, and by age. Nevertheless, the person skilled in the art will consider that depending on the assay used, the normal values provided by the manufacturer can normally be used as a reference, or alternatively, the normal values as assessed by the clinician in the specific setting.

The polypeptides of the invention typically comprise at least one ISVD against vWF. The immunoglobulin single variable domains of the present invention bind to and/or have affinity for vWF. In the context of the present invention, "vWF" includes, but is not limited to, cynomolgus, baboon, pig, guinea pig, mouse, and/or human vWF and most preferred human vWF, i.e. SEQ ID NO: 20 or Gen Bank entry: NP_000543.

Preferably, the ISVD against vWF essentially consists of 4 framework regions (FR1 to FR4, respectively) and 3 complementarity determining regions (CDR1 to CDR3, respectively), in which:
a) CDR1 comprises or essentially consists of:
   the amino acid sequence YNPMG; or
   an amino acid sequence that has 2 or only 1 amino acid difference(s) with the amino acid sequence YNPMG;
and
b) CDR2 comprises or essentially consists of:
   the amino acid sequence AISRTGGSTYYPDSVEG; or
   an amino acid sequence that has at least 80%, preferably at least 90%, more preferably at least 95%, even more preferably at least 99% sequence identity with the amino acid sequence AISRTGGSTYYPDSVEG; or
   an amino acid sequence that has 2 or only 1 amino acid difference(s) with the amino acid sequence AISRTGGSTYYPDSVEG;
and
c) CDR3 comprises or essentially consists of:
   the amino acid sequence AGVRAEDGRVRTLPSEYTF; or
   an amino acid sequence that has at least 80%, preferably at least 90%, more preferably at least 95%, even more preferably at least 99% sequence identity with the amino acid sequence AGVRAEDGRVRTLPSEYTF; or
   an amino acid sequence that has 2 or only 1 amino acid difference(s) with the amino acid sequence AGVRAEDGRVRTLPSEYTF.

Even more preferably, the ISVD against vWF essentially consists of 4 framework regions (FR1 to FR4, respectively) and 3 complementarity determining regions (CDR1 to CDR3, respectively), in which:
a) CDR1 is YNPMG (SEQ ID NO: 20);
b) CDR2 is AISRTGGSTYYPDSVEG (SEQ ID NO: 21); and
c) CDR3 is AGVRAEDGRVRTLPSEYTF (SEQ ID NO: 22).

Even more preferably, the ISVD against vWF is represented by SEQ ID NO: 19 (12A02H1).

Preferably, the polypeptides of the invention comprise or consist of at least two ISVDs against vWF.

Even more preferably, the polypeptides of the present invention comprise or consist of two ISVDs against vWF defined by SEQ ID NO:s 1-18, and most preferably SEQ ID NO: 1 (ALX 0081; INN Caplacizumab). ALX 0081 is a bivalent Nanobody, consisting of two identical monovalent building blocks, that target vWF.

The polypeptides comprising at least one ISVD against vWF, e.g. SEQ ID NO:s 1-19, may be used in a treatment of a vWF-related disease, in particular thrombotic thrombocytopenic purpura (TTP).

The terms "polypeptide" and "amino acid sequence" are used interchangeably herein.

Thus, for example, suitable polypeptides for use in the invention may include the compounds in Table A-1, e.g. SEQ ID NO: 1-19 or 20-22, or a compound having 80% or more, more preferably 85% or more, most preferred 90%, 95%, 96%, 97%, 98%, 99% or more, amino acid sequence identity to a compound in Table A-1 (see Definition section for "sequence identity").

Preferably the ISVD against vWF for use in the polypeptides of the invention are 12A02H1-like compounds. For the purposes of the present description a 12A02H1-like compound is a compound which comprises 12A02H1 (i.e. SEQ ID NO: 19) or a compound having 80% or more, more preferably 85% or more, most preferably 90%, 95%, 96%, 97%, 98%, 99% or more, amino acid sequence identity to 12A02H1 (SEQ ID NO: 19). A particularly preferred polypeptide comprising two ISVDs against vWF is ALX 0081 (SEQ ID NO: 1).

Immunoglobulin single variable domains, such as camelid VHH domains, camelized VH domains or humanized VHH domains, represent a rapidly growing class of therapeutics. For example, immunoglobulin single variable domains against vWF have been described in WO2004/015425, WO2004/062551, WO2006/074947, WO2006/122825, WO2009/115614, and WO2011/067160. Further preferred immunoglobulin single variable domains for use in the polypeptides of the invention include the improved Nanobodies described in WO06/122825.

Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as VHH domains or VH/VL domains, respectively). In addition, the term "sequence" as used herein (for example in terms like "immunoglobulin sequence", "antibody sequence", "variable domain sequence", "VHH sequence" or "protein sequence"), should generally be understood to include both the relevant amino acid sequence as well as nucleic acids or nucleotide sequences encoding the same, unless the context requires a more limited interpretation.

The term "immunoglobulin single variable domain" ("ISVD"), interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In contrast, the binding site of an immunoglobulin single variable domain is formed by a single VH or VL domain. Hence, the antigen binding site of an immunoglobulin single variable domain is formed by no more than three CDRs.

The term "immunoglobulin single variable domain" hence does not comprise conventional immunoglobulins or their fragments which require interaction of at least two variable domains for the formation of an antigen binding site. This is also the case for embodiments of the invention which "comprise" or "contain" an immunoglobulin single variable domain. In the context of the present invention, such embodiments exclude conventional immunoglobulins or their fragments. Thus, a polypeptide or a composition that "comprises" or "contains" an immunoglobulin single variable domain may relate to e.g. constructs comprising more than one immunoglobulin single variable domain. Alternatively, there may be further constituents other than the immunoglobulin single variable domains, e.g. auxiliary agents of different kinds, protein tags, colorants, dyes, etc. However, these terms do comprise fragments of conventional immunoglobulins wherein the antigen binding site is formed by a single variable domain.

Generally, single variable domains will be amino acid sequences that essentially consist of 4 framework regions (FR1 to FR4 respectively) and 3 complementarity determining regions (CDR1 to CDR3 respectively). Such single variable domains and fragments are most preferably such that they comprise an immunoglobulin fold or are capable for forming, under suitable conditions, an immunoglobulin fold. As such, the single variable domain may for example comprise a light chain variable domain sequence (e.g. a VL-sequence) or a suitable fragment thereof; or a heavy chain variable domain sequence (e.g. a VH-sequence or VHH sequence) or a suitable fragment thereof; as long as it is capable of forming a single antigen binding unit (i.e. a functional antigen binding unit that essentially consists of the single variable domain, such that the single antigen binding domain does not need to interact with another variable domain to form a functional antigen binding unit, as is for example the case for the variable domains that are present in for example conventional antibodies and scFv fragments that need to interact with another variable domain—e.g. through a VH/VL interaction—to form a functional antigen binding domain).

In one embodiment of the invention, the immunoglobulin single variable domains are light chain variable domain sequences (e.g. a VL-sequence), or heavy chain variable domain sequences (e.g. a VH-sequence); more specifically, the immunoglobulin single variable domains can be heavy chain variable domain sequences that are derived from a conventional four-chain antibody or heavy chain variable domain sequences that are derived from a heavy chain antibody (e.g. a VHH).

For a general description of heavy chain antibodies and the variable domains thereof, reference is inter alia made to the prior art cited herein, as well as to the prior art mentioned on page 59 of WO 08/020079 and to the list of references mentioned on pages 41-43 of the International application WO 06/040153, which prior art and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. In WO 08/101985 and WO 08/142164.

For example, the single variable domain or immunoglobulin single variable domain (or an amino acid sequence that is suitable for use as an immunoglobulin single variable domain) may be a (single) domain antibody (or an amino acid sequence that is suitable for use as a (single) domain antibody), a "dAb" or dAb (or an amino acid sequence that is suitable for use as a dAb) or a Nanobody (as defined herein, and including but not limited to a VHH sequence); other single variable domains, or any suitable fragment of any one thereof. For a general description of (single) domain antibodies, reference is also made to the prior art cited herein, as well as to EP 0 368 684. For the term "dAb's", reference is for example made to Ward et al. 1989 (Nature 341 (6242): 544-6), to Holt et al. 2003 (Trends Biotechnol. 21(11): 484-490); as well as to for example WO 04/068820, WO 06/030220, WO 06/003388 and other published patent applications of Domantis Ltd. It should also be noted that, although less preferred in the context of the present invention because they are not of mammalian origin, single variable domains can be derived from certain species of shark (for example, the so-called "IgNAR domains", see for example WO 05/18629).

In particular, the immunoglobulin single variable domain may be a Nanobody® (as defined herein) or a suitable fragment thereof. [Note: Nanobody®, Nanobodies® and Nanoclone® are registered trademarks of Ablynx N.V.] For a general description of Nanobodies, reference is made to the further description below, as well as to the prior art cited herein, such as e.g. described in WO 08/020079 (page 16).

The amino acid sequence and structure of an immunoglobulin sequence, in particular an immunoglobulin single variable domain can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively.

The total number of amino acid residues in an immunoglobulin single variable domain can be in the region of 110-120, is preferably 112-115, and is most preferably 113, It should however be noted that parts, fragments, analogs or derivatives of an immunoglobulin single variable domain are not particularly limited as to their length and/or size, as long as such parts, fragments, analogs or derivatives meet the further requirements outlined herein and are also preferably suitable for the purposes described herein.

Thus, in the meaning of the present invention, the term "immunoglobulin single variable domain" or "single variable domain" comprises peptides which are derived from a non-human source, preferably a camelid, preferably a camel heavy chain antibody. They may be humanized, as previously described, e.g. In WO 08/101985 and WO 08/142164. Moreover, the term comprises polypeptides derived from non-camelid sources, e.g. mouse or human, which have been "camelized", as previously described, e.g. In WO 08/101985 and WO 08/142164.

The term "immunoglobulin single variable domain" encompasses immunoglobulin sequences of different origin, comprising mouse, rat, rabbit, donkey, human and camelid immunoglobulin sequences. It also includes fully human, humanized or chimeric immunoglobulin sequences. For example, it comprises camelid immunoglobulin sequences and humanized camelid immunoglobulin sequences, or camelized immunoglobulin single variable domains, e.g. camelized dAb as described by Ward et al (see for example WO 94/04678 and Davies and Riechmann 1994, Febs Lett. 339: 285 and 1996, Protein Engineering 9: 531).

All the ISVDs against vWF (or vWF binders) mentioned above are well known from the literature. This includes their manufacture (see in particular e.g. WO2006/122825 but also WO2004/062551). For example, ALX 0081 is prepared as described e.g. In WO2006/122825 or WO2009/115614.

The immunoglobulin single variable domains provided by the invention are preferably in isolated form or essentially isolated form, or form part of a protein or polypeptide of the invention, which may comprise or essentially consist of one or more immunoglobulin single variable domains and which may optionally further comprise one or more further amino acid sequences (all optionally linked via one or more suitable linkers). For example, and without limitation, the one or more immunoglobulin single variable domains may be used as a binding unit in such a protein or polypeptide, which may optionally contain one or more further amino acid sequences that can serve as a binding unit (i.e. against one or more other targets than cell associated antigens), so as to provide a monovalent, multivalent or multispecific polypeptide of the invention, respectively, all as described herein. Such a protein or polypeptide may also be in isolated or essentially isolated form. Thus, according to the invention, immunoglobulin single variable domains comprise constructs comprising two or more antigen binding units in the form of single domains, as outlined above. For example, two (or more) immunoglobulin single variable domains with the same or different antigen specificity can be linked to form e.g. a bivalent, trivalent or multivalent construct. By combining immunoglobulin single variable domains of two or more specificities, bispecific, trispecific etc. constructs can be formed. For example, a polypeptide according to the invention may comprise two immunoglobulin single variable domains directed against target A, and one immunoglobulin single variable domain against target B, making it bivalent for A and monovalent for B. Such constructs and modifications thereof, which the skilled person can readily envisage, are all encompassed by the present invention. In particular embodiments, the invention relates to bi-paratopic constructs comprising at least two immunoglobulin single variable domains directed to different epitopes within the same target antigen.

All these molecules are also referred to as "polypeptide of the invention", which is synonymous with "immunoglobulin sequences" or "immunoglobulin single variable domains" of the invention.

In addition, the term "sequence" as used herein (for example in terms like "immunoglobulin sequence", "antibody sequence", "variable domain sequence", "$V_{HH}$-sequence" or "protein sequence"), should generally be understood to include both the relevant amino acid sequence as well as nucleic acid sequences or nucleotide sequences encoding the same, unless the context requires a more limited interpretation.

According to one non-limiting embodiment of the invention, the immunoglobulin sequences, Nanobody® or polypeptide of the invention is glycosylated. According to another non-limiting embodiment of the invention, the immunoglobulin sequences, Nanobody® or polypeptide of the invention is non-glycosylated.

As mentioned supra, the present invention relates to polypeptides typically comprising at least one, such as 2 or more ISVDs against vWF, i.e. ISVDs that bind and/or have affinity for an antigen as defined herein, e.g. von Willebrand Factor (vWF) and preferably human vWF (SEQ ID NO: 20).

In the context of the present invention, "binding to and/or having affinity for" a certain antigen has the usual meaning in the art as understood e.g. In the context of antibodies and their respective antigens.

In particular embodiments of the invention, the term "binds to and/or having affinity for" means that the immunoglobulin sequence specifically interacts with an antigen, and is used interchangeably with immunoglobulin sequences "against" the said antigen.

The term "specificity" refers to the number of different types of antigens or antigenic determinants to which a particular immunoglobulin sequence, antigen-binding molecule or antigen-binding protein (such as a Nanobody® or a polypeptide of the invention) can bind. The specificity of an antigen-binding protein can be determined based on affinity and/or avidity. The affinity, represented by the equilibrium constant for the dissociation of an antigen with an antigen-binding protein (KD), is a measure for the binding strength between an antigenic determinant and an antigen-binding site on the antigen-binding protein: the lesser the value of the KD, the stronger the binding strength between an antigenic determinant and the antigen-binding molecule (alternatively, the affinity can also be expressed as the affinity constant (KA), which is 1/KD). As will be clear to the skilled person (for example on the basis of the further disclosure herein), affinity can be determined in a manner known per se, depending on the specific antigen of interest. Avidity is the measure of the strength of binding between an antigen-binding molecule (such as a Nanobody® or polypeptide of the invention) and the pertinent antigen. Avidity is related to both the affinity between an antigenic determinant and its antigen binding site on the antigen-binding molecule and the number of pertinent binding sites present on the antigen-binding molecule.

Typically, immunoglobulin sequences of the present invention (such as the amino acid sequences, Nanobodies® and/or polypeptides of the invention) will bind to their antigen with a dissociation constant (KD) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant (KA) of $10^5$ to $10^{12}$ liter/moles or more, and preferably $10^7$ to $10^{12}$ liter/moles or more and more preferably $10^8$ to $10^{12}$ liter/moles), and/or bind to cell associated antigens as defined herein with a kon-rate of between $10^2$ $M^{-1}$ $s^{-1}$ to about $10^7$ $M^{-1}$ $s^{-1}$, preferably between $10^3$ $M^{-1}$ $s^{-1}$ and $10^7$ $M^{-1}$ $s^{-1}$, more preferably between $10^4$ $M^{-1}$ $s^{-1}$ and $10^7$ $M^{-1}$ $s^{-1}$, such as between $10^5$ $M^{-1}$ $s^{-1}$ and $10^7$ $M^{-1}$ $s^{-1}$; and/or bind to cell associated antigens as defined herein with a koff rate between 1 $s^{-1}$ (t½=0.69 s) and $10^{-6}$ $s^{-1}$ (providing a near irreversible complex with a t½ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Any KD value greater than $10^{-4}$ M (or any KA value lower than $10^4$ $M^{-1}$) is generally considered to indicate non-specific binding.

Preferably, a monovalent immunoglobulin sequence of the invention will bind to the desired antigen with an affinity less than 500 nM, preferably less than 200 nM, more preferably less than 10 nM, such as less than 500 pM.

Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant (KD) may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more than $10^{-4}$ moles/liter or $10^{-3}$ moles/liter (e.g., of $10^{-2}$ moles/liter). Optionally, as will also be clear to the skilled person, the (actual or apparent) dissociation constant may be calculated on the basis of the (actual or apparent) association constant (KA), by means of the relationship [KD=1/KA].

The affinity denotes the strength or stability of a molecular interaction. The affinity is commonly given as by the KD, or dissociation constant, which has units of mol/liter (or M). The affinity can also be expressed as an association constant, KA, which equals 1/KD and has units of (mol/liter)$^{-1}$ (or M$^{-1}$). In the present specification, the stability of the interaction between two molecules (such as an amino acid sequence, immunoglobulin sequence, Nanobody® or polypeptide of the invention and its intended target) will mainly be expressed in terms of the KD value of their interaction; it being clear to the skilled person that in view of the relation KA=1/KD, specifying the strength of molecular interaction by its KD value can also be used to calculate the corresponding KA value. The KD-value characterizes the strength of a molecular interaction also in a thermodynamic sense as it is related to the free energy (DG) of binding by the well-known relation DG=RT·ln(KD) (equivalently DG=−RT·ln(KA)), where R equals the gas constant, T equals the absolute temperature and ln denotes the natural logarithm.

The KD for biological interactions, such as the binding of the immunoglobulin sequences of the invention to the cell associated antigen as defined herein, which are considered meaningful (e.g. specific) are typically in the range of $10^{-10}$ M (0.1 nM) to $10^{-5}$ M (10000 nM). The stronger an interaction is, the lower is its KD.

The KD can also be expressed as the ratio of the dissociation rate constant of a complex, denoted as koff, to the rate of its association, denoted kon (so that KD=koff/kon and KA=kon/koff). The off-rate koff has units s$^{-1}$ (where s is the SI unit notation of second). The on-rate kon has units M$^{-1}$ s$^{-1}$.

As regards immunoglobulin sequences of the invention, the on-rate may vary between $10^2$ M$^{-1}$ s$^{-1}$ to about $10^7$ M$^{-1}$ s$^{-1}$, approaching the diffusion-limited association rate constant for bimolecular interactions. The off-rate is related to the half-life of a given molecular interaction by the relation t½=ln(2)/koff. The off-rate of immunoglobulin sequences of the invention may vary between $10^{-6}$ s$^{-1}$ (near irreversible complex with a t½ of multiple days) to 1 s$^{-1}$ (t½=0.69 s).

The affinity of a molecular interaction between two molecules can be measured via different techniques known per se, such as the well-known surface plasmon resonance (SPR) biosensor technique (see for example Ober et al., Intern. Immunology, 13, 1551-1559, 2001) where one molecule is immobilized on the biosensor chip and the other molecule is passed over the immobilized molecule under flow conditions yielding kon, koff measurements and hence KD (or KA) values. This can for example be performed using the well-known Biacore instruments.

It will also be clear to the skilled person that the measured KD may correspond to the apparent KD if the measuring process somehow influences the intrinsic binding affinity of the implied molecules for example by artefacts related to the coating on the biosensor of one molecule. Also, an apparent KD may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (J. Immunol. Methods, 77, 305-19, 1985). This method establishes a solution phase binding equilibrium measurement and avoids possible artefacts relating to adsorption of one of the molecules on a support such as plastic.

However, the accurate measurement of KD may be quite labour-intensive and as consequence, often apparent KD values are determined to assess the binding strength of two molecules. It should be noted that as long as all measurements are made in a consistent way (e.g. keeping the assay conditions unchanged) apparent KD measurements can be used as an approximation of the true KD and hence in the present document KD and apparent KD should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an IC50 value is obtained corresponding to the concentration of A at which the signal measured for C in absence of A is halved. Provided KD ref, the KD of the reference molecule, is known, as well as the total concentration cref of the reference molecule, the apparent KD for the interaction A-B can be obtained from following formula: KD=IC50/(1+cref/KD ref). Note that if cref<<KD ref, KD≈IC50. Provided the measurement of the IC50 is performed in a consistent way (e.g. keeping cref fixed) for the binders that are compared, the strength or stability of a molecular interaction can be assessed by the IC50 and this measurement is judged as equivalent to KD or to apparent KD throughout this text.

The present invention relates to immunoglobulin single variable domains described in, or obtainable by the methods as disclosed in WO2004/015425, WO2004/062551, WO2006/074947, WO2006/122825, WO2009/115614, or WO2011/067160, all in the name of the present applicant.

The invention also encompasses optimized variants of these amino acid sequences. Generally, an "optimized variant" of an amino acid sequence according to the invention is a variant that comprises one or more beneficial substitutions such as a substitutions increasing i) the degree of "humanization", ii) the chemical stability, and/or iii) the level of expression; while the potency (measured e.g. by the potency assay as described in the experimental part of WO2006/122825 remains comparable (i.e. within a 10% deviation) to the wild type 12A02 (as defined in WO2006/122825) or comparable to the variant 12A02H1 (SEQ ID NO: 19), also as defined in WO2006/122825. Preferably, compared to the wild-type sequence of 12A02, an amino acid sequence of the invention contains at least one such substitution, and preferably at least two such substitutions, and preferably at least three humanizing substitutions and preferably at least 10 such humanizing substitutions.

In a particular aspect, the amino acid sequences of the invention contain a total of between 1 and 15, preferably between 2 and 14, such as between 9 and 13, e.g. 10, 11 or 12 amino acid substitutions compared to the wild-type sequence 12A02. As mentioned, these differences preferably at least comprise one and preferably at least two, such as three, four or five or ten humanizing substitutions, and may optionally comprise one or more further substitutions (such as any one of, or any suitable combination of any two or more of, the further substitutions (a) to (c) as mentioned herein). Again, based on the disclosure herein and optionally after a limited degree of trial and error, the skilled person will be able to select (a suitable combination of) one or more such suitable humanizing and/or further substitutions.

The present invention encompasses polypeptide sequences that are highly similar to any of the specific examples provided herein, or any of the specific examples defined by reference above. Highly similar means an amino acid identity of at least 90%, e.g. 95, 97, 98 or 99%. The highly similar polypeptide sequences will have the same function as the sequence they are derived from, i.e. they will bind to vWF, more specifically bind to and inhibit interaction between vWF and platelets.

In a particular embodiment, the invention relates to sequences highly similar to any one of SEQ ID NO:s 1-19, in particular SEQ ID NO: 1. However, for each variant sequence stability in the formulation as defined herein has to be evaluated, such that the invention in particular refers to variants or highly similar sequences which are stable in the formulations as defined herein.

Methods to generate polypeptide sequences of the invention are widely known and include e.g. recombinant expression or synthesis. The skilled person is well acquainted with suitable expression technology, e.g. suitable recombinant vectors and host cells, e.g. bacterial or yeast host cells. The skilled person is also well acquainted with suitable purification techniques and protocols.

The present invention provides also formulations of polypeptides comprising at least one immunoglobulin single variable domain against vWF, e.g. ALX 0081, which are stable, and preferably suitable for pharmaceutical uses, including the preparation of medicaments (also called "pharmaceutical formulation of the invention" or "formulation(s) of the invention").

In particular embodiments, the formulation comprises one or more polypeptides selected from SEQ ID NO:s 1-19, preferably SEQ ID NO: 1.

The term "pharmaceutical formulation" refers to a preparation which is in such form as to permit the biological activity of the active ingredient (the polypeptide of the invention) to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

The term "excipient" as used herein refers to an inert substance which is commonly used as a diluent, vehicle, preservative, lyoprotectant, surfactant, binder, carrier or stabilizing agent for compounds which impart a beneficial physical property to a formulation. The skilled person is familiar with excipients suitable for pharmaceutical purposes, which may have particular functions in the formulation, such as lyoprotection, stabilization, preservation, etc.

A "sterile" formulation is aseptic or free or essentially free from all living microorganisms and their spores. This is readily accomplished by filtration through sterile filtration membranes.

A "stable" formulation is one in which the protein therein essentially retains its physical stability and/or chemical stability and/or biological activity upon storage. Preferably, the formulation essentially retains its physical and chemical stability, as well as its biological activity upon storage.

The storage period is generally selected based on the intended shelf-life of the formulation. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. In certain embodiments, the formulation is stable at about 40° C. for at least about 1, 2, 3, 4, 5, 6, 7, 8, or more weeks. Furthermore, the formulation is preferably stable following freezing (to, e.g., −20° C. or −70° C.) and thawing of the formulation, for example following 1, 2 3, 4, or 5 cycles of freezing and thawing. Stability can be evaluated qualitatively and/or quantitatively in a variety of different ways known by the person skilled in the art. Stability studies showed that ALX 0081 is stable at −20° C. for at least 3 years.

The formulation comprises an aqueous carrier. The aqueous carrier is in particular a buffer.

As used herein, "buffer" refers to a buffered solution that resists changes in pH by the action of its acid-base conjugate components. The formulation of the invention comprises a buffer selected from at least one of citrate or phosphate buffer, preferably a citrate buffer. As determined previously, these buffers enhance the stability of the vWF binders.

The formulation according to the invention comprises a citrate buffer at a concentration in the range of 5-200 mM, preferably 7.5-80 mM, even more preferably 10-50, e.g. 10, 15, 20, 25 or 30 mM, and most preferably 20 mM, wherein each value is understood to optionally encompass a range of ±5 mM. Alternatively, the formulation according to the invention may comprise a phosphate buffer at a concentration in the range of 5-200 mM, preferably 5-80 mM, more preferably 7.5-60 mM, even more preferably 10-40, e.g. 10, 15, 20, 25 or 30 mM, and most preferably 10 mM, wherein each value is understood to optionally encompass a range of ±5 mM. It will be understood that a lower concentration of the buffer has an effect on the final osmolality, and correspondingly on the additional solutes that may have to be added.

The pH of the formulation of the invention is in the range 5.0 to 7.5, wherein each value is understood to encompass a range of ±0.2. The most advantageous pH will depend on the buffer comprised in the formulation. Hence, the invention relates particularly to a formulation comprising a phosphate buffer, which preferably has a pH in the range of 6.5 to 7.5, preferably 6.9, 7.0, 7.1, e.g. 7.1. It was shown that a formulation comprising a citrate buffer was outstandingly suitable for storage and use. Hence, the present invention relates to a formulation comprising a citrate buffer, which preferably has a pH between 6.0 and 7.0, more preferably 6.1, 6.2, 6.3, 6.4, 6.5, 6.6, 6.7, 6.8 or 6.9, e.g. 6.5, wherein each value is understood to optionally encompass a range of ±0.2.

The formulations of the invention will comprise the polypeptides of the invention, in particular the immunoglobulin single variable domains or polypeptides comprising at least one immunoglobulin single variable domain against vWF, such as ALX 0081, at a concentration that is suitable for clinical purposes, which includes concentrations used in stock solutions for dilution prior to use on the patient. Apart from improved stabilization, the formulations of the invention enable high concentrations of the polypeptides comprising at least one ISVD against vWF, such as ALX 0081.

Typical concentrations of the active agent, e.g. polypeptides comprising at least one ISVD against vWF such as ALX 0081, in formulations of the invention comprise the non-limiting examples of concentrations in the range of 0.1 to 150 mg/mL, such as 1-100 mg/mL, 5-80 mg/mL, or 10-40 mg/mL, preferably 10 mg/mL, wherein each value is understood to optionally encompass a range of ±20% (e.g. a value of 10 optionally encompasses a range of 8 to 12 mg/mL).

In a further embodiment of the invention, the formulation according to any aspect of the invention may further comprise a detergent or surfactant.

Herein, a "surfactant" refers to a surface-active agent, preferably a nonionic surfactant. Examples of surfactants herein include polysorbate; poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT® series (Mona Industries, Inc., Paterson, N.J.); polyethyl glycol, polypropyl glycol, and copolymers of ethylene and propylene glycol (e.g. Pluronics, PF68 etc.); etc. In one embodiment, the surfactant herein is polysorbate 80. Preferred suitable detergents or surfactants for use with the invention include, but are not limited to, polyoxyethylene sorbitan fatty acid esters e.g. polysorbate-20, -40, -60, -65, -80 or -85. Common brand names for polysorbates include Alkest, Canarcel and Tween. The skilled person knows further non-limiting examples of detergents, such as those listed e.g. In WO2010/077422. In a preferred embodiment, the detergent is a non-ionic detergent. More specifically, the detergent is polysorbate-80, also designated Tween-80 hereafter. The skilled person can readily determine a suitable concentration of detergent for a formulation of the invention. Typically, the concentration will be as low as possible, whilst maintaining the beneficial effects of the detergents, e.g. a stabilizing effect under conditions of shear stress, e.g. stirring, which reduces aggregation of the formulated polypeptides of the invention. In exemplary, non-limiting embodiments, the concentration of the detergent may be in the range of 0.001 to 0.5%, e.g. 0.001, 0.002, 0.003, 0.004, 0.005, 0.01, 0.015, 0.02, 0.025, 0.03, 0.035, 0.04, 0.045, 0.05%, 0.1%, 0.2%, 0.3%, 0.4% or 0.5%, preferably in a concentration between 0.01 and 0.05%, more preferably between 0.01 and 0.02%, e.g. 0.01% (v/v).

The formulation of the invention may further comprise excipients such as preservatives.

A "preservative" is a compound which can be optionally included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. In one embodiment, the preservative herein is benzyl alcohol.

The formulation of the invention may further comprise stabilizing agents, such as a polyols.

A "polyol" is a substance with multiple hydroxyl groups, and includes sugars (reducing and nonreducing sugars), sugar alcohols and sugar acids. A polyol may optionally be included in the formulation, for instance to improve stability. In certain embodiments, polyols herein have a molecular weight which is less than about 600 kD (e.g. In the range from about 120 to about 400 kD). A "reducing sugar" is one which contains a hemi-acetal group that can reduce metal ions or react covalently with lysine and other amino groups in proteins and a "nonreducing sugar" is one which does not have these properties of a reducing sugar. Examples of reducing sugars are fructose, mannose, maltose, lactose, arabinose, xylose, ribose, rhamnose, galactose and glucose. Nonreducing sugars include sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof. Where it desired that the formulation is freeze-thaw stable, the polyol is preferably one which does not crystallize at freezing temperatures (e.g. −20° C.) such that it destabilizes the antibody in the formulation. In certain embodiments, nonreducing sugars such as sucrose and trehalose are examples of polyols, with sucrose being preferred, despite the solution stability of trehalose.

Therapeutic compounds of the invention used in accordance with the present invention are prepared for storage by mixing a polypeptide(s) having the desired degree of purity with optional pharmaceutically acceptable carriers, excipients or stabilizers (Remington's Pharmaceutical Sciences 16th edition, Osol, A. Ed. [1980]), in the form of lyophilized formulations or aqueous solutions. Acceptable carriers, excipients, or stabilizers are nontoxic to recipients at the dosages and concentrations employed. Accordingly, the formulations according to the invention may also optionally comprise one or more excipients.

Commonly used stabilizers and preservatives are well known to the skilled person (see e.g. WO2010/077422). Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, hydrophilic polymers such as polyvinyl pyrrolidone, cellulose based substances, polyethylene glycol, sodium carboxymethylcellulose, polyacrylates, waxes, gelatin, polyethylene polyoxypropylene block polymers, polyethylene glycol and wool fat. antioxidants including ascorbic acid and methionine; preservatives; low molecular weight (less than about 10 residues) polypeptides; proteins; and amino acids such as glycine, glutamine, asparagine, histidine, arginine, or lysine. In advantageous embodiments, the excipient may be one or more selected from the list consisting of NaCl, trehalose, sucrose, mannitol or glycine.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The polypeptides of the invention may be formulated into any pharmaceutically acceptable formulation. The formulation may be liquid or dry. The formulation may be generated via mixing, drying, lyophilization, vacuum drying, or any known method for formulating pharmaceutical compositions.

A preferred formulation of the invention comprises a polypeptide comprising at least one ISVD against vWF, such as ALX 0081, in a phosphate buffer solution (pH 7.1). Even more preferably, a formulation of the invention comprises a polypeptide comprising at least one ISVD against vWF, such as ALX 0081, in a phosphate buffer solution (pH 7.1), Glycine (0.2 M) and polysorbate 80 (0.02% v/v).

The polypeptides of the invention may further be formulated as described in PCT/EP14/060107.

A preferred formulation comprises:
(a) a polypeptide comprising at least one ISVD against vWF, such as ALX 0081 at a concentration from about 0.1 mg/mL to about 80 mg/mL;
(b) an excipient chosen from sucrose, glycine, mannitol, trehalose or NaCl at a concentration of about 1% to about 15% (w/v);
(c) Tween-80 at a concentration of about 0.001% to 0.5% (v/v); and
(d) a citrate buffer at a concentration of about 5 mM to about 200 mM such that the pH of the formulation is about 6.0 to 7.0.

A further preferred formulation of the invention comprises a polypeptide comprising at least one ISVD against vWF, such as ALX 0081, preferably at a concentration of 10 mg/ml, a citrate buffer at a concentration of 20 mM (pH 6.5), further comprising 7% sucrose (w/v), and Tween-80 at a concentration of 0.01% (v/v).

In some embodiments, a formulation is stored as a liquid. In other embodiments, a formulation is prepared as a liquid and then is dried, e.g., by lyophilization or spray-drying, prior to storage. A dried formulation can be used as a dry compound, e.g., as an aerosol or powder, or reconstituted to its original or another concentration, e.g., using water, a buffer, or other appropriate liquid.

The present invention also relates to vials comprising filled with lyophilisate containing 12.5 mg caplacizumab and excipients for solution for injection. Excipients (per mL of reconstituted solution): 0.21 mg citric acid, 5.58 mg tri sodium citrate di-hydrate, 70 mg sucrose, 0.11 mg polysorbate-80 per vial (pH 6.5 +/−0.5). After reconstitution with 1 mL Water for injection (WFI) strength is 12.5 mg/mL. caplacizumab (for administered nominal dose of 10 mg).

The invention also encompasses products obtainable by further processing of a liquid formulation, such as a frozen, lyophilized or spray-dried product. Upon reconstitution, these solid products can become liquid formulations as described herein (but are not limited thereto). In its broadest sense, therefore, the term "formulation" encompasses both liquid and solid formulations. However, solid formulations are understood as derivable from the liquid formulations (e.g. by freezing, freeze-drying or spray-drying), and hence have various characteristics that are defined by the features specified for liquid formulations herein. The invention does not exclude reconstitution that leads to a composition that deviates from the original composition before e.g. freeze- or spray drying. accordingly, the lyophilized formulation may be reconstituted to produce a formulation that has a concentration that differs from the original concentration (i.e., before lyophilization), depending upon the amount of water or diluent added to the lyophilate relative to the volume of liquid that was originally freeze-dried. Suitable formulations can be identified by assaying one or more parameters of antibody integrity.

In a preferred embodiment, the formulations according to the invention are isotonic in relation to human blood. Isotonic solutions possess the same osmotic pressure as blood plasma, and so can be intravenously infused into a subject without changing the osmotic pressure of the subject's blood plasma. Tonicity can be expressed in terms of osmolality, which can be a theoretical osmolality, or preferably an experimentally determined osmolality. Typically, osmolality will be in the range of 290±60 mOsm/kg, preferably 290 ±20 mOsm/kg.

The formulations of the invention may also comprise compounds that are specifically useful for protecting the polypeptide of the invention during freeze-drying. Such compounds are also known as lyoprotectants, and are well known to the skilled person. Specific examples include, but are not limited to sugars like sucrose, sorbitol or trehalose; amino acids such as glutamate, in particular monosodium glutamate or histidine; betain, magnesium sulfate, sugar alcohols, propylene glycol, polyethylene glycols and combinations thereof. By appreciating the invention, the required amount of such a compound to be added can readily be determined by the skilled person under consideration of stability of the formulation in liquid form and when undergoing lyophilization. Formulations that are particularly suitable for freeze-drying may furthermore comprise bulking agents. Suitable agents are widely known to the skilled person. It has been shown that a formulation comprising sucrose was not only particularly suited for maintaining the physical stability, during e.g. storage and freeze-thawing, of the vWF binders, but also as lyoprotectant.

As outlined, any of the above formulations can be further processed e.g. by lyophilization, spray-drying or freezing, e.g. bulk freezing. The resulting processed product has characteristics derived from the liquid starting formulation, as defined above. Where necessary, additional agents may be included for further processing, such as, for instance, lyoprotectants, etc.

The formulations of the present invention have the effect after lyophilization of maintaining the chemical and physical integrity of the polypeptides of the present invention, in particular ALX 0081, i.e. even after prolonged storage, e.g. for durations as defined above, at temperatures between −70° C. and +40° C., the purity/impurity profile of the product is essentially not changing. For example, prolonged storage after lyophilization did not have a significant effect on RP-HPLC, SE-HPLC or cIEF profiles.

The polypeptides of the invention can be produced by any commonly used method. Typical examples include the recombinant expression in suitable host systems, e.g. bacteria or yeast. The polypeptides of the invention will undergo a suitable purification regimen prior to being formulated in accordance to the present invention.

In general, the polypeptides of the invention are produced by living host cells that have been genetically engineered to produce the polypeptide. Methods of genetically engineering cells to produce proteins are well known in the art. See e.g. Ausubel et al., eds. (1990), Current Protocols in Molecular Biology (Wiley, New York). Such methods include introducing nucleic acids that encode and allow expression of the polypeptide into living host cells. These host cells can be bacterial cells, fungal cells, or animal cells grown in culture. Bacterial host cells include, but are not limited to, *Escherichia coli* cells. Examples of suitable *E. coli* strains include: HB101, DH5a, GM2929, JM109, KW251, NM538, NM539, and any *E. coli* strain that fails to cleave foreign DNA. Fungal host cells that can be used include, but are not limited to, *Saccharomyces cerevisiae*, *Pichia pastoris* and *Aspergillus* cells. A few examples of animal cell lines that can be used are CHO, VERO, BHK, HeLa, Cos, MDCK, 293, 3T3, and WI38. New animal cell lines can be established using methods well known by those skilled in the art (e.g., by transformation, viral infection, and/or selection). Optionally, the polypeptide can be secreted by the host cells into the medium.

In some embodiments, the polypeptides can be produced in bacterial cells, e.g., *E. coli* cells. For example, if the polypeptide is encoded by sequences in a phage display vector that includes a suppressible stop codon between the display entity and a bacteriophage protein (or fragment thereof), the vector nucleic acid can be transferred into a bacterial cell that cannot suppress a stop codon. In this case, the polypeptide is not fused to the gene III protein and is secreted into the periplasm and/or media.

The polypeptides can also be produced in eukaryotic cells. In one embodiment, the polypeptides are expressed in a yeast cell such as Pichia (see, e.g., Powers et al. J Immunol Methods 251:123-35 (2001)), *Hansenula*, or *Saccharomyces*.

In one embodiment, polypeptides are produced in mammalian cells. Typical mammalian host cells for expressing the clone antibodies or antigen-binding fragments thereof include Chinese Hamster Ovary (CHO cells) (including dhfr—CHO cells, described in Urlaub and Chasin, Proc. Natl. Acad. Sci. USA 77:4216-4220(1980), used with a DHFR selectable marker, e.g., as described in Kaufman and Sharp, Mol. Biol. 159:601-621 (1982)), lymphocytic cell lines, e.g., NS0 myeloma cells and SP2 cells, COS cells, and a cell from a transgenic animal, e.g., a transgenic mammal. For example, the cell is a mammary epithelial cell.

In addition to the nucleic acid sequences encoding the polypeptide, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216; 4,634,665; and 5,179,017). For example, typically the selectable marker gene confers resistance to drugs, such as G418, hygromycin, or methotrexate, on a host cell into which the vector has been introduced.

Standard molecular biology techniques can be used to prepare the recombinant expression vector, transfect the host cells, select for transformants, culture the host cells and recover the antibody molecule from the culture medium. For example, the polypeptides of the invention can be isolated by affinity chromatography.

In one embodiment, the polypeptide of the invention is purified as described in WO 10/056550. In an exemplary embodiment, the polypeptide is purified from one or more contaminants by: contacting a mixture of polypeptide and contaminant(s) with a Protein A-based support and/or an ion exchange support, under conditions that allow the polypeptide to bind to or adsorb to the support; removing one or more contaminants by washing the bound support under conditions where the polypeptide remains bound to the support, and selectively eluting the polypeptide from the support by eluting the adsorbed polypeptide molecule with an elution buffer.

The polypeptides of the invention can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody molecule and a signal sequence for secretion. The milk produced by females of such transgenic mammals includes, secreted therein, the single domain of interest. The antibody molecule can be purified from the milk, or for some applications, used directly.

The present invention encompasses methods of producing the formulations as defined herein.

The purification and formulation steps may coincide, e.g. when the polypeptides of the invention are eluted from a column using a buffer according to the present invention. Alternatively, the formulations of the invention can be prepared by exchanging a buffer by any suitable means, e.g. means widely used in the art such as dialyzing, ultrafiltration, etc.

In some embodiments the method of producing a formulation of the invention may also relate to the reconstitution of a lyophilized or spray-dried formulation, e.g. by addition of water or a suitable buffer (which may optionally comprise further excipients).

The methods for preparing a formulation according to the present invention may encompass further steps, such as filling it into vials suitable for clinical use, such as sealed containers and/or confectioning it in a dosage unit form. The methods may also comprise further steps such as spray-drying, lyophilization, or freezing, e.g. bulk freezing. The invention also encompasses the containers, dosage unit forms, or other products obtainable by any of the methods recited herein.

The formulations of the present invention can be used to store the polypeptides of the invention, e.g. polypeptides comprising at least one ISVD against vWF, such as ALX 0081, as defined herein. Thus, the invention encompasses a method of storage of the polypeptides of the invention as used herein, characterized by the use of a formulation as defined herein. More specifically, the invention encompasses methods for stabilizing the polypeptides of the invention for storage, comprising e.g. the preparation of a formulation as described herein. Storage can be 1-36 months, such as 1, 1.5, 3, 6, 9, 12, 18, 24, 30 or 36 months, e.g. at least 12 months, optionally at a temperature between −70° C. and +40° C., such as −70° C., −20° C., +5° C., +25° C. or +40° C., preferably a temperature between −70° C. and +25° C., more preferably at a temperature between −20° C. and +5° C. Thus, storage may encompass freezing, freeze-drying (lyophilization) and/or spray-drying. The storage methods may furthermore comprise the assessment of physical and chemical integrity of the vWF binders as defined herein.

The present invention also relates to methods for analyzing formulations comprising at least one of the vWF binders as defined herein. The formulations can be analyzed for any signs of chemical or physical instability of the vWF binders as defined herein. For example, the formulations can be assessed for the presence of degradation products, e.g. low molecular weight derivatives such as proteolytic fragments; and/or for chemical derivatives, e.g. pyroglutamate variants; and/or for high molecular weight derivatives such as aggregates, agglomerates, etc. The formulation can also be assessed for total protein content and/or potency. Each of the various assay methods as referred to herein can be used in the analysis method of the present invention.

Thus, the present invention also relates to a method for monitoring and/or assessing the quality and/or stability of a formulation, e.g. during one or more of manufacture, storage and use. The invention also relates to a method of quality control of a formulation, e.g. to assess that the formulation meets product specifications as further described herein. The invention in any of these aspects comprises one or more selected from the comparison with one or more reference samples, the analysis of batch to batch variation, and the ongoing monitoring of a production process.

The present invention relates to any product that is associated with the formulations of the present invention, e.g. by comprising them, or by being necessary for their production or confectioning, without any limitations.

For example, the present invention relates to an article of manufacture, e.g. a sealed container comprising one or more of the formulations according to the present invention.

The invention also relates to a pharmaceutical unit dosage form, e.g. a dosage form suitable for parenteral administration (e.g., intradermally, intramuscularly, intraperitoneally, intravenously and subcutaneously) to a patient, preferably a human patient, comprising one or more of the formulation according to any embodiment described herein.

The dosage unit form can be e.g. in the format of a prefilled syringe, an ampoule, cartridge or a vial.

Also provided are kits or articles of manufacture, comprising the formulation of the invention and instructions for use by, e.g., a healthcare professional. The kits or articles of manufacture may include a vial or a syringe containing the formulation of the invention as described herein.

Preferably, the vial or syringe is composed of glass, plastic, or a polymeric material chosen from a cyclic olefin polymer or copolymer. The syringe, ampoule, cartridge or vial can be manufactured of any suitable material, such as glass or plastic and may include rubber materials, such as rubber stoppers for vials and rubber plungers and rubber seals for syringes and cartridges. The invention also relates to a kit comprising one or more of the formulations according to the present invention. The kit may further comprise instructions for use and/or a clinical package leaflet. In any embodiment of the products as defined herein, the invention also encompasses the presence of packaging material, instructions for use, and/or clinical package leaflets, e.g. as required by regulatory aspects.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein.

Alternatively, the degree of sequence identity between two amino acid sequences may be calculated using a known computer algorithm, such as those mentioned above for determining the degree of sequence identity for nucleotide sequences, again using standard settings.

Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide.

Such conservative amino acid substitutions are well known in the art, for example from WO 04/037999, GB-A-3 357 768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein. Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Natl. Acad. Sci. USA 81: 140-144, 1984; Kyte & Doolittle; J Molec. Biol. 157: 105-132, 1981, and Goldman et al., Ann. Rev. Biophys. Chem. 15: 321-353, 1986, all incorporated herein in their entirety by reference. Information on the primary, secondary and tertiary structure of Nanobodies® is given in the description herein and in the general background art cited above. Also, for this purpose, the crystal structure of a $V_{HH}$ domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

The present invention also relates to a method of treating or preventing a vWF-related disease, such as e.g. acute coronary syndrome (ACS), transient cerebral ischemic attack, unstable or stable angina pectoris, stroke, myocardial infarction or thrombotic thrombocytopenic purpura (UP); said method comprising administering to a subject a pharmaceutical composition comprising the formulation of the invention, thereby reducing one or more symptoms associated with said vWF-related disease. In particular, said vWF-related disease is TTP.

In addition, the present invention relates to a method for the treatment of a human patient susceptible to or diagnosed with a disease characterized by a vWF-related disease, comprising administering an effective amount of a polypeptide comprising at least one immunoglobulin single variable domain (ISVD) against von Willebrand Factor (vWF) to the human patient.

The present invention provides a method of treating or preventing a vWF-related disease, such as TTP, comprising administering to a human, 5-40 mg dose of a polypeptide comprising at least one immunoglobulin single variable domain (ISVD) against von Willebrand Factor (vWF), thereby reducing one or more symptoms associated with the vWF-related disease.

The present invention provides a treatment as described herein, wherein said administering a polypeptide as described herein is followed within 5 min to 8 h by performing a first Plasma Exchange (PE).

The present invention provides a treatment as described herein, wherein said administering of a polypeptide as described herein is preceded by performing a preceded Plasma Exchange (PE), within 36 h, preferably 32, 30, 28, 26, 24, 22, 20, 18, or 16 h, preferably about 24 h of said first PE.

The present invention provides a treatment as described herein, wherein said first PE is followed by administering a second dose of 1-40 mg, preferably 10 mg of a polypeptide as described herein within 5 min to 8 h, such as within 10 min to 6 h or 15 min to 4 h, for instance within 8 h, 7 h, 6 h, 5 h, 4 h, 3 h, 3 h, 1 h, 45 min, 30 min, 20 min, 15 min, 10 min or even 5 min, for instance wherein said second dose of said polypeptide is administered within 1-60 min, such as 30 min of said first PE, preferably by subcutaneous injection.

The present invention provides a treatment as described herein, further comprising:
(i) performing a PE; (followed by)
(ii) administering a dose of 5-40 mg of a polypeptide as described herein 15 min to 4 h after said PE of step (i); and
(iii) optionally measuring the platelet count and/or ADAMTS13 activity of said patient,
wherein step (i) and step (ii) are repeated once per day until the platelet count of said patient is >150000/µl and/or the ADAMTS13 activity is at least 10% such as at least 15%, 20%, 25%, 30%, 35%, 45% or even 50% of the ADAMTS13 reference activity.

The present invention provides also a treatment as described herein, further comprising administering once per day a dose of 5-40 mg of a polypeptide as described herein for at least 5, 10, 15, 20, 25, or even 30 days after the platelet count of said patient is >150.000/µl.

The present invention provides a treatment as described herein, further comprising administering once per day a dose of 5-40 mg of a polypeptide as described herein until said human enters remission.

The present invention provides a treatment as described herein, comprising administering said polypeptide until the ADAMTS13 activity is at least 10% such as at least 15%, 20%, 25%, 30%, 35%, 45% or even 50% of the ADAMTS13 reference activity.

In another embodiment of the invention, an article of manufacture containing materials useful for the treatment of a disease as described above is provided. The article of manufacture comprises a contained, a label and a package insert. Suitable containers include, for example, bottles, vials, syringes, etc. The containers may be of a variety of materials such as glass or plastic. The container holds the composition which is effective in treating the condition and may have a sterile access port (for example the container may be an intravenous solution bag or a vial having a stopper pierceable by a hypodermic injection needle). At least one active agent in the composition is the polypeptide of the invention, such as ALX 0081. The label on, or associated with, the container indicates that the composition is used for treating the condition of choice. The article of manufacture may further comprise a second container comprising a pharmaceutically acceptable buffer, such as a phosphate buffer saline or a citrate buffered saline as described herein. It may further include other materials desirable from a user or commercial standpoint, including other buffers, diluents, filters, needles and syringes.

The present invention provides a kit or an article of manufacture, comprising a container containing the polypeptide as described herein or the formulation as described herein, and instructions for use.

The present invention provides a kit or article of manufacture as described herein, wherein the formulation is present in a vial or an injectable syringe.

The present invention provides a kit or article of manufacture as described herein, wherein the formulation is present in a prefilled injectable syringe.

The present invention provides a kit or article of manufacture as described herein, wherein the syringe or a vial is composed of glass, plastic, or a polymeric material chosen from a cyclic olefin polymer or copolymer.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The invention will now be further described by means of the following non-limiting preferred aspects, examples and figures.

The entire contents of all of the references (including literature references, issued patents, published patent applications, and co-pending patent applications) cited throughout this application are hereby expressly incorporated by reference, in particular for the teaching that is referenced hereinabove.

6. ABBREVIATIONS

AE adverse events
ACS acute coronary syndrome
ADAMTS13 a disintegrin-like and metalloprotease with thrombospondin repeats 13
ALX 0081 Caplacizumab
AMI Acute myocardial infarction
BNP brain natriuretic peptide
BMI body mass index
BU Bethesda Units
COR complementarity determining region
cIEF Capillary IsoElectric Focusing
dAb single domain antibody
ELISA enzyme-linked immunosorbent assay
HR Hazard Ratio
ISVD Immunoglobulin single variable domain
ITT intent-to-treat
i.v. intravenous
FR framework region
KA association constant
KD dissociation constant
LDH Lactate dehydrogenase
NSE neuron specific enolase
NT proBNP N-terminal pro brain natriuretic peptide
PE or PEX plasma exchange
PP per protocol
RICO Ristocetin cofactor activity RP-HPLC Reverse Phase High Performance Liquid Chromatography
SAE serious adverse event
s.c. subcutaneous
scFv single chain variable fragment
Solvent/Detergent
SE-HPLC Size Exclusion High Performance Liquid Chromatography
SPR surface plasmon resonance
TnI troponin I
TnT troponin T
TRALI Transfusion related acute lung injury
TTP Thrombotic thrombocytopenic purpura
TTR time-to-response
ULN Upper limit normal
ULvWF ultra-large vWF
VH heavy chain variable domain
VHH heavy chain variable domain sequence that is derived from a heavy chain antibody
VL light chain variable domain
vWF von Willebrand Factor

7. EXAMPLES

7.1 Applicable Regulations

All human samples used in the Examples section were either obtained from commercial sources or from human volunteers (after all required consents and approvals were obtained) and were used in according with the applicable legal and regulatory requirements (including those regarding medical secret and patient privacy).

Clinical trials were performed in accordance with applicable laws and regulations (including the Declaration of Helsinki and the principles of medical secret and the protection of patient privacy) and after all required approvals (including approvals by relevant ethics committees) and consents (including informed consent of subjects involved) were obtained.

The objectives and contents of this clinical study as well as its results were treated as confidential and have not been made accessible to third parties. Employees participating in the study were bound by confidentiality. All unused drugs were either returned to the applicant or destroyed.

7.2 Effects of ALX 0081 on Platelet Adhesion to Endothelial Cell-Derived ULvWF and on the Activity of ADAMTS13

Goal: the goal of this study was to evaluate if a polypeptide of the invention, such as ALX 0081 can inhibit adhesion of platelets to ULvWF. This could then serve as proof of concept for the use of a polypeptide of the invention, such as ALX-081, for treatment of TTP patients in an acute episode. The study also determines the effect of a polypeptide of the invention, such as ALX 0081, on the activity of ADAMTS13.

Method: the flow chamber test was used to test whether a polypeptide of the invention, such as ALX 0081, can inhibit the interaction between platelets and ULvWF according to Sixma (Sixma et al. 1998 Thromb Res 92: 543-546). In short, endothelial cells were cultivated on coverslips and stimulated, thereby secreting ULvWF. Plasma from TTP patients was supplemented with platelets and perfused over the stimulated cells. Strings of platelets adhering to ULvWF were visualized by real time video-microscopy. The experiment was repeated in the presence of increasing concentrations of a polypeptide of the invention, such as ALX 0081. In order to determine the effect of a polypeptide of the invention, such as ALX 0081, on the cleavage of ULvWF by ADAMTS13, two types of experiments were used. In the first experiment, cleavage of platelet strings by ADAMTS13 was evaluated in the absence of excess a polypeptide of the invention, such as ALX 0081. In the second experiment, a recombinant fragment composed of the A1-A2-A3 domain of vWF was used to evaluate the inhibitory effect of a polypeptide of the invention, such as ALX 0081, on ADAMTS13.

Results: ALX 0081 inhibited platelet string formation on ULvWF at all concentrations tested and had no effect on platelet string detachment by ADAMTS13. The polypeptide of the invention, such as ALX 0081, also had no effect on the cleavage of the recombinant A1-A2-A3 domain fragment of vWF by ADAMTS13. The polypeptide of the invention, such as ALX 0081, was also not able to dislodge the platelets from already formed strings in this experiment.

Conclusion: this study delivers a proof of concept that a polypeptide of the invention, such as ALX 0081, can be used to treat TTP patients. It also proves that a polypeptide of the invention, such as ALX 0081, does not interfere with the ADAMTS13 activity.

7.3 Eligibility Criteria

Patients had to fulfill all of the following criteria to be eligible for study admission:

Inclusion Criteria
1. 18 years of age or older
2. Men or women willing to accept an acceptable contraceptive regimen
3. Patients with clinical diagnosis of TTP
4. Necessitating PE (one, single PE session prior to randomisation into the study is allowed)
5. Subject accessible to follow-up
6. Obtained, signed and dated informed consent Exclusion Criteria
1. Platelet count greater or equal to 100,000/μL
2. Severe active infection indicated by sepsis (requirement for pressors with or without positive blood cultures)
3. Clinical evidence of enteric infection with *E. coli* 0157 or related organism
4. Anti-phospholipid syndrome
5. Diagnosis of DIC
6. Pregnancy or breast-feeding
7. Haematopoietic stem cell or bone marrow transplantation-associated thrombotic microangiopathy
8. Known congenital TTP
9. Active bleeding or high risk of bleeding
10. Uncontrolled arterial hypertension
11. Known chronic treatment with anticoagulant treatment that can not be stopped safely, including but not limited to vitamin K antagonists, heparin or LMWH, and non-acetyl salicylic acid non-steroidal anti-inflammatory molecules
12. Severe or life threatening clinical condition other than TTP that would impair participation in the trial
13. Subjects with malignancies resulting in a life expectation of less than 3 months
14. Subjects with known or suspected bone marrow carcinosis
15. Subjects who cannot comply with study protocol requirements and procedures.

16. Known hypersensitivity to the active substance or to excipients of the study drug
17. Severe liver impairment, corresponding to grade 3 toxicity defined by the CTCAE scale. For the key liver parameters, this is defined as follows:
    bilirubin>3×ULN (need to differentiate isolated increase in indirect bilirubin due to haemolysis, this is not an exclusion parameter but disease related)
    ALT/AST>5×ULN
    AP>5×ULN
    gamma glutamyl transpeptidase (GGT)>5×ULN
18. Severe chronic renal impairment, as defined by GFR<30 mL/min

7.4 Study Design

The present study was designed as a Phase II multicentre, single-blinded, parallel design, randomised, placebo-controlled study (Titan trial). The study population were symptomatic patients with acute episodes of acquired TTP, requiring treatment with PE. After confirmation of eligibility to study participation (cf. Example 7.3), patients were randomised in a ratio of 1:1 to either receive ALX 0081 or placebo as adjunctive therapy to PE (FIG. 1). Patients were randomised prior to the start of PE treatment. In exceptional cases however (due to need or ability to start PE in a time frame which did not allow all required screening and/or baseline study procedures to be performed), a patient was randomised after a preceding, single PE session ("preceding PE"), but prior to the start of the next PE session ("first PE"). This overall next PE session was started within 24 hours of the end of the preceding PE session, and was considered the first PE-on-study ("first PE").

The patients were followed in different phases during this study:
Screening and baseline measurements after admission to hospital
Treatment phase
    Single i.v. bolus study drug administered via push injection
    Daily PE adjunctive s.c. treatment phase
    Post-daily PE s.c. treatment phase (including PE tapering if applicable, and study drug post-PE for 30 days after the very last PE)
Follow-up phase The patients received the best medical care and treatment judged appropriate by the investigator at each site and according to the guidelines for treatment of TTP. The maximum total duration of individual study participation was a maximum of 15 months: a treatment phase of up to 90 days and a follow-up period of maximum of 1 year after remission or after 90 days of treatment, whichever came first. In general, patients were hospitalised for at least 1 day after the last daily PE.

The study drug was administered as an adjunctive treatment at specific times relative to PE procedures. The study drug consisted of 10 mg of Caplacizumab ("treatment group") or placebo ("placebo group"), once or twice daily.

7.4.1 First Drug Administration

Patients received a first i.v. bolus of 10 mg ALX 0081 or placebo via push injection 15 minutes to 6 h prior to the initiation of the first PE, This first PE was followed by s.c. administration of 10 mg study drug within 30 minutes after the end of the PE procedure.

During the complete PE treatment period (including tapering and PE given for exacerbations), the study drug was administered daily via s.c. injections.

If 1 PE per day was scheduled, 10 mg of study drug was administered within 30 minutes after the end of the PE procedure.

If 2 PEs per day were scheduled, 10 mg of study drug was administered within 30 minutes after the end of each PE procedure. The maximum total daily dose of study drug was hence 20 mg, If less than 1 PE per day was scheduled (i.e. during a tapering regimen), 10 mg of study drug was administered daily. On days with a PE, study drug administration was within 30 minutes after the end of the PE procedure; on days without PE, study drug administration was 24 h (±1 h) after previous administration.

Daily s.c. study drug administration of 10 mg continued for 30 days after the very last PE (including tapering),

7.4.2 Primary Endpoint

The primary endpoint of this phase II study was the time-to-response (TTR), based on the following criterion: recovery of platelets ≥150,000/μL. In order to qualify as meeting the endpoint, the response had to be confirmed at 48 hours after the initial reporting of platelet recovery equal to or above 150,000/μL by a de novo measure of platelets ≥150,000/μL and lactate dehydrogenase (LDH) ≤2×upper limit of normal (ULN), i.e., "confirmed platelet response". Platelet count is the pivotal laboratory marker for therapeutic decision making in patients with TTP. This is based on the fact that ULvWF-mediated platelet aggregation is the common pathophysiological mechanism behind TTP, leading to severe thrombocytopenia and microangiopathic hemolytic anemia, which are the main hallmarks in the diagnosis of TTP (Scully et al. supra).

7.4.3 Determination of ADAMTS13 Activity

ADAMTS13 activity and functional inhibitor activity were measured by a fluorogenic assay using the FRETS-VWF73 substrate (Kokame et al, 2005. Br J Haematol 129(1):93-100; Kremer Hovinga et al. 2006 J Thromb Haemost 4(5):1146-8).

Briefly, the FRETS-VWF73 assay were performed essentially as described (Kokame et al. 2005 supra) with the following modifications: Pefabloc SC (Boehringer, Mannheim, Germany) was added to the assay buffer (5 mmol L-1 Bis-Tris, 25 mmol L-1 CaCl2, 0.005% Tween-20, pH 6.0) at a final concentration of 1 mmol L-1. Assay calibration was obtained by using a normal human plasma pool (NHP; Swiss Red Cross Blood Services, Bern, Switzerland) diluted 1:25 (100%) in assay buffer. Further calibration samples were obtained by serial predilutions of NHP of 3:4 (75%), 1:2 (50%), 1:4 (25%), 1:10 (10%), 1:20 (5%), 1:50 (2%) and 1:100 (1%) in heat-inactivated NHP, incubated for 30 min at 56° C. followed by 15 min of centrifugation at 15 000×g) to correct for a plasma matrix effect in the lower activity range of the standard curve. All of these standard samples as well as heat-inactivated NHP (0% ADAMTS13 activity) and all test samples were subsequently diluted 1:25 in assay buffer. Next, 25 μL of each diluted standard or patient sample was incubated at 37° C. in a 384-well white plate (NUNC, Roskilde, Denmark). After 10 min, 25 μl of 4 μmol L-1 FRETS-VWF73 peptide substrate dissolved in assay buffer was added to each well and evolution of fluorescence recorded at 37° C. in a fluorescence microplate reader (GENios, Tecan, Zürich, Switzerland) equipped with a 340 nm excitation filter (band width 35 nm) and a 450 nm emission filter (band width 25 nm). Fluorescence evolution was measured over time (every 5 min for 42 cycles). The reaction rate was calculated by linear regression analysis (Passing-Bablok) of fluorescence evolution over time from 5 (cycle 2) to 60 min (cycle 13). The slope of the regression curve was calculated for each calibration sample, and used to generate the calibration curve (trend line: y=ax+b; with x=ADAMTS13 (%) and y=delta RFU/delta time). The ADAMTS13 activity (%) of a sample was then calculated as: (y−b)×1/a.

ADAMTS13 functional inhibitor activity was measured by the same fluorogenic FRETS-VWF73 method by determination of residual ADAMTS13 activity of normal human plasma after 1:1 (v:v) incubation for 2 hours at 37° C. with heat-inactivated patient's plasma (30 min at 56° C.).

For each analytical batch, a calibration curve was generated using a normal human plasma pool (NHP; Swiss Red Cross Blood Services, Bern, Switzerland) diluted 1:25 (100%) in assay buffer. Further calibration samples were obtained by serial predilutions of NHP of 1:2 (50%), 1:4 (25%), 1:10 (10%), 1:20 (5%), 1:50 (2%) and 1:100 (1%) in heat-inactivated NHP. All calibration points were applied in singlicate. Acceptance criteria: (1) The slope of the final regression of the standard curve line has to be >6.0; and (2) $R^2$ of the regression of the final plot has to be >0.98 (or R>0.9899). Otherwise, the assay was rejected.

7.5 Results in TTP Patients

7.5.1 Subject Disposition and Analysis of Populations

The phase II study comprised a sample size of 75 patients, which were randomized as set out in Table 2.

The primary analysis population was the intent-to-treat (ITT) population, which consisted of all randomised subjects according to a randomised treatment assignment. In addition, for the efficacy analyses, the per protocol population (PP) was used. The PP population is a subset of the ITT population and consists of all randomised subjects, according to the randomised treatment assignment, with exclusion of all major protocol deviations and violators.

TABLE 2

|  | Caplacizumab N (%) | Placebo N (%) | Total N (%) |
| --- | --- | --- | --- |
| Randomized | 36 | 39 | 75 |
| Not treated | 1 (2.8%) | 2 (5.1%) | 3 (4.0%) |
| ITT population | 36 (100%) | 39 (100%) | 75 (100%) |
| Safety population | 35 (97.2%) | 37 (94.9%) | 72 (96.0%) |

In conclusion, there was an even distribution in both treatment arms, i.e. patients receiving Caplacizumab (treatment group) and patients receiving placebo (placebo-group). The treatment arms were furthermore well-balanced for age, ethnicity/race and BMI.

The base line characteristics of various parameters were assessed in the patients of the treatment group and the placebo group. In Table 3 the baseline platelet counts and LDH are presented. The increased of LDH levels is a sign of increased haemolysis and/or tissue ischaemia.

TABLE 3

|  | Caplacizumab N = 35 | Placebo N = 37 | Total N = 72 |
| --- | --- | --- | --- |
| Platelets ($10^3/mm^3$) mean ± St Dev | 21.1 ± 18.2 | 28.0 ± 20.0 | 24.6 ± 193 |
| minimum, maximum | 2, 70 | 5, 84 | 2, 84 |
| LDH (U/L) mean ± St Dv | 1277.4 ± 852.5 | 1270.1 ± 939.3 | 1273.7 ± 891.0 |
| minimum, maximum | 240, 3874 | 247, 4703 | 240, 4703 |

There is a slightly lower mean baseline platelet count for the Caplacizumab arm. In both arms, the mean platelet counts were very low at baseline, which is consistent with a severe disease setting but is also indicative that all subjects presenting were considered for inclusion and there is no bias towards less severely thrombocytopenic subjects.

LDH means are comparable for both treatment arms.

In Table 4 the baseline vWF:Ag and ADAMTS13 activity are presented.

TABLE 4

|  | Caplacizumab N = 36 | Placebo N = 39 | Total N = 75 |
| --- | --- | --- | --- |
| vWF:Ag (%) mean ± St Dev; ULN = 150 | 180.3 ± 78.2 | 185.5 ± 80.8 | 183.1 ± 78.9 |
| ADAMTS13 activity n (%) |  |  |  |
| <5%, indicative of idiopathic TTP | 21 (58.3%) | 22 (56.4%) | 43 (57.3%) |
| ≥5% | 9 (25.0%) | 14 (35.9%) | 23 (30.7%) |
| missing | 6 (16.7%) | 3 (7.7%) | 9 (12%) |

Both treatment arms were well balanced for vWF:AG and ADAMTS13 activity. More than half of the subjects have idiopathic TTP as indicated by <5% ADAMTS13 activity.

7.5.2 Study Results: Primary Endpoints

The time-to-response of blood markers was monitored in a survival setting. The primary endpoint time-to-response of blood markers comprised recovery of platelets ≥150,000/μL. The platelet levels represent a reliable surrogate marker for TTP disease activity. Zero to time-to-event period was set at 30 days.

The results are depicted in Table 5.

Data were evaluated according to stratification (1 PEX prior to Randomization: YES & NO), which aggregates to an overall Hazard Ratio for the complete ITT population of 2.197 with a p value=0.013 for the overall ITT population. The Hazard Ratio means that at any time, subjects receiving Caplacizumab have more than twice the rate of achieving the primary endpoint of confirmed platelet recovery in comparison to subjects on Placebo.

Reduction in time to Confirmed Platelet Response (primary endpoint):
  In the group of subjects with no PEX prior to randomization, a median of 4.92 days for the Placebo arm reduced to 3.00 days for the Caplacizumab arm: 39% reduction (PEX prior to Randomization=NO)
  In the group of subjects which received one PEX prior to randomization, a median of 4.31 days for the Placebo arm reduced to 2.44 days for the Caplacizumab arm: 43% reduction (PEX prior to Randomization=YES)
The median times of 4.31 days and 4.92 days for the Placebo arms of the 2 strata (1 PEX prior to Randomization:

YES & NO) are lower than that expected from medical literature and investigators' data (6 days; cf. Bandarenko et al. Journal of Clinical Apheresis 1998; 13: 133-141). This implies that even with an improved standard of care treatment over historical data, the Caplacizumab treatment was superior.

The 95% CI of the time to Confirmed Platelet Response is 2 to 3 times narrower for the Caplacizumab arms versus the Placebo arms. This implies that the time to disease resolution is less variable in the Caplacizumab treatment arms than the Placebo arms.

TABLE 5

| PEX prior * | | Caplacizumab N = 36 | Placebo N = 39 |
|---|---|---|---|
| No | Subjects censored at 30 days n (%) | 5 (13.9%) | 11 (28.2%) |
| No | Subjects with confirmed platelet response n (%) | 29 (80.6%) | 24 (61.5%) |
| No | Medan (95% Cl) | 3.00 (2.74, 3.88) | 4.92 (3.21, 6.59) |
| No | 25$^{th}$ & 75$^{th}$ percentile | 2.72 & 4.31 | 3.01 & 11.37 |
| Yes | Subjects censored at 30 days n (%) | 0 | 0 |
| Yes | Subjects with confirmed platelet response n (%) | 2 (5.6%) | 4 (10.3%) |
| Yes | Median (95% Cl) | 2.44 (1.92, 2.97) | 4.31 (2.91, 5.68) |
| Yes | 25$^{th}$ & 75$^{th}$ percentile | 1.92 & 197 | 3.37 & 5.23 |
| Overall Hazard Rate Ratio for Caplacizumab versus Placebo (95% Cl) | | 2.197 (1.278, 3.778) | |
| Stratified Log-rank Test p-value | | 0.013 | |

* 1 PEX prior to randomization

7.5.3 Study Results: Exacerbations

Within the ITT population, the proportion of subjects with exacerbations was determined. Exacerbation refers to a recurrent thrombocytopenia following a confirmed platelet response and requiring a re-initiation of daily PE treatment after ≥1 day but ≤30 days after the last PE.

The results are depicted in Table 6.

TABLE 6

| | Caplacizumab N = 36 | Placebo N = 39 | Total N = 75 |
|---|---|---|---|
| Overall Population | 3 (8.3%) | 11 (28.2%) | 14 (18.7%) |

There are 3× more exacerbations in the Placebo arm versus the Caplacizumab arm.

This confirms the finding that the polypeptide of the invention, such as ALX 0081, can be solely responsible for treating and/or alleviating (the symptoms of) TTP.

7.5.4 Study Results: Relapses

The number of subjects relapsing of TTP was assessed. Relapse of TTP is defined as a de novo event of TTP that occurs later than 30 days after the last daily PE. In Table 7 the proportion of subjects with exacerbation and/or relapse in the 1st month after end of treatment in the ITT Population is depicted.

TABLE 7

| | Caplacizumab N = 36 | Placebo N = 39 | Total N = 75 |
|---|---|---|---|
| Overall Population Relapse (at least) | 13 (36.1%) | 13 (33.3%) | 26 (34.7%) |
| Baseline ADAMTS13 activity n (%) | 10 | 2 | 4 |
| <5% | 7 (19.4%) | 8 (20.5%) | 15 (20.0%) |
| ≥5% | 2 (5.6%) | 5 (12.8%) | 7 (9.3%) |

We see more Relapses in the Caplacizumab arm versus the Placebo (PLC) arm, which evens out the total numbers.

The Relapses in the Caplacizumab arm occur often within a few days of the Caplacizumab treatment termination. This implies a possible 'extended' exacerbation rather than a relapse. Therefore Caplacizumab (CAP) treatment may possibly have been too short duration for some subjects. Indeed, higher number of early relapses in the CAP arm substantiates a protective effect and warrants longer CAP treatment in some patients. This implies that Caplacizumab treatment should be continued for prolonged periods.

It is interesting to note that in both treatment arms, relapses are more prominent in patients with a baseline ADAMTS13 activity of <5%, even though the ADAMTS13 activity was only available in a subset of the patients. This may indicate that patients with baseline ADAMTS13 activity of <5% are more prone to relapses (or exacerbations) and Caplacizumab treatment should be continued for even longer periods compared to patients with higher activity (cf. Example 7.5.8).

7.5.5 Study Results: Complete Remission

The number of subjects with complete remission in the ITT population was assessed. Complete remission is here defined as confirmed platelet response and the absence of exacerbation. The results are depicted in Table 8.

TABLE 8

| | | Caplacizumab N = 36 | Placebo N = 39 |
|---|---|---|---|
| Overall | Number of subjects n (%) | 29 (80.6%) | 18 (46.2%) |
| | 95% Cl | (64.0%, 91.8%) | (30.1%, 62.8%) |
| Baseline ADAMTS13 activity <5% | Number of subjects n (%) | 17 (47.2%) | 12 (30.8%) |
| | 95% Cl | (58.1%, 94.6%) | (32.2%, 75.6%) |
| Baseline ADAMTS13 activity ≥5% | Number of subjects n (%) | 7 (19.4%) | 6 (15.4%) |
| | 95% Cl | (40.0%, 97.2%) | (17.7%, 71.1%) |

The Caplacizumab arm presents 1.6× more subjects with complete remission versus the Placebo arm. The greater proportion of complete remission, coupled with the faster and narrower distribution of time to confirmed platelet response supports a greater predictability of patient response to PE in the CAP arm, and is reflected in number of days of PE. The number of consecutive days of PE was (mean±st dev) 6.6±3.4 days for CAP versus 8.1±6.5 days for PLC with a total plasma volume administered including tapering of 22.5±15.9 liters for CAP versus 28.4±21.3 liters for PLC. The effect appears more pronounced for the subgroup of subjects with low Baseline ADAMTS13 activity, even though the baseline ADAMTS13 activity data is incomplete for the Caplacizumab group (cf. Example 7.5.8).

7.5.6 Study Results: Safety Assessment

The incidence of adverse events (AE) and serious adverse events (SAE) was assessed, focusing on bleeding related SAEs and immune-related SAEs. The SAE assessment included haemorrhage from catheter insertion, sepsis, catheter thrombosis, pneumothorax, fluid overload, hypoxia, hypotension, anaphylactoid reactions and TRALI. The number of serious adverse events was similar across both treatment arms: 57% in the Caplacizumab arm compared to 51% in the placebo arm. The number of adverse events was also similar across treatment arms: 97% in the Caplacizumab arm compared to 100% in the placebo arm. The number of subjects with bleeding related AEs was slightly elevated in the Caplacizumab arm (54%) compared to the placebo arm (38%).

The most prominent risk of the currently used non-specific antithrombotic agents is an elevated bleeding diathesis or apparent bleeding. Beside any unexpected effects, bleeding also represents the most relevant safety concern for Caplacizumab. In this context Caplacizumab was investigated in a preclinical surgical bleeding model. In this study, surgical blood loss in animals receiving Caplacizumab was comparable to blood loss in Heparin® treated animals, and 2- and 4 fold less than in Plavix® and ReoPro® treated animals, respectively. Although this is a positive indication that Caplacizumab may be safer than Plavix® and ReoPro® in terms of bleeding risk, this was assessed in healthy persons. As indicated above, TTP-patient differs in many aspects from a healthy person in respect of vWF. Study treatment was stopped due to an adverse event in 4 patients treated with Caplacizumab and in 2 patients treated with placebo. The increase in bleeding tendency was however well manageable.

TTP is potentially life threatening. There were 2 deaths (5.4%) reported in the trial, both in the placebo arm. It is noted that the number of deaths in the placebo arm is less than described in literature (10-30%). This may infer that the outcome of TTP has improved due to more effective standards of care (in the present study).

7.5.7 Study Results: Further Optimized Treatment Protocol

A further optimized treatment protocol was designed by the present inventors, based on the idea that the distribution of confirmed platelet response time is shorter and not skewed and biased to the right (longer time to response) in the CAP arm in comparison to the placebo arm.

In the further optimized treatment protocol, all subjects are treated in essence as set out before in point 7.4, "Study Design", but with the following major modification: the PE treatment period is set for 3-5 days, such as 3 days or 4 days or 5 days, preferably 3 days. The PE treatment period is independent of the recovery of platelets ($\geq 150,000/\mu l$). Daily s.c. study drug administration is continued for at least 10 days, such as 20 days or 30 days after the very last PE, but preferably for at least 10 days, such as 20 days or 30 days after the recovery of platelets to $\geq 150,000/\mu l$. In evaluating the further optimized treatment protocol, the primary endpoint will be the number of exacerbations as defined supra.

In the further optimized treatment protocol, the burden for the patient and the costs are decreased.

7.5.8 ADAMTS13 Activity

It was set out to further evaluate ADAMTS13 activity as marker for underlying disease activity and to evaluate ADAMTS13 activity as marker to guide optimal treatment duration of caplacizumab, to maintain treatment benefit.

In this case, when ADAMTS13 activity was <10% then underlying disease activity was assumed. An ADAMTS13 activity of $\geq 10\%$ assumed no underlying disease activity.

Exacerbations and relapses were related to the patient's available ADAMTS13 activity data. If a relapse was preceded by continuously low ADAMTS13 (<10%) during treatment, it was considered as relapse of presenting episode. If a relapse was preceded by ADAMTS13 activity $\geq 10\%$ during treatment, it was considered as a de novo TTP episode. Patients excluded from analysis were (i) non-ADAMTS13 mediated disease ($\geq 10\%$ at baseline) (n=3), and (ii) patients with insufficient data (n=12).

(i) Patients without Exacerbations or Relapses:
Caplacizumab: 13/16 (81%) had ADAMST13 activity values $\geq 10\%$ close to treatment stop
Placebo: 14/16 (88%) had ADAMST13 activity values $\geq 10\%$ close to treatment stop Hence, in the majority of patients without exacerbation or relapse, ADAMTS13 activity recovered to levels above 10%, suggesting resolution of the presenting TTP episode.

(ii) Patients with Exacerbations
Caplacizumab: 2/3 (67%) had ADAMTS13 activity <10% around their exacerbation
Placebo: 7/8 (88%) had ADAMTS13 activity <10% around their exacerbation Hence, in the majority of patients with exacerbations of TTP, ADAMTS13 activity was below 10%, suggesting unresolved disease activity leading to exacerbation.

(iii) Patients with Relapses of the Presenting TTP Episode
Caplacizumab: 7/7 (100%) had ADAMST13 activity values <10% close to treatment stop; relapses occurred within 10 days after treatment stop
Placebo: N/A—all were 'de novo' relapses Hence, all subjects in the caplacizumab group with relapses occurring soon after the end of treatment had continuously low ADAMTS13 activity (<10%), indicative of ongoing disease.

(iv) Patients with a De Nova Relapse Episode
Caplacizumab: 4/4 (100%) had ADAMST13 activity values $\geq 10\%$ close to treatment stop; relapses occurred within $\geq 30$ days after treatment stop (range: 30-167 days). All 4 patients had again ADAMTS13 activity <10% at the time of relapse.
Placebo: 2/3 (67%) had ADAMST13 activity values $\geq 10\%$ close to treatment stop; relapses occurred within X30 days after treatment stop (range: 30-167 days). There were no data available around the time of relapse.

Hence, in the majority of patients with a de novo relapse episode, ADAMTS13 activity recovered to levels above 10% near treatment stop, suggesting resolution of the presenting TTP episode; values were low again (<10%) at the time of relapse, indicating a new TTP episode (v) Conclusion
The data support the use of ADAMTS13 activity as predictive marker for recurrences of TTP and its potential for treatment decisions.

ADAMTS13 activity is able to predict relapses which occur shortly after stopping caplacizumab treatment.

These relapses are considered as relapses of the presenting TTP episode (unresolved disease activity, based on continuously low ADAMTS13 activity).

A 30-day treatment period (post PE) with caplacizumab has demonstrated a significant impact on the number of exacerbations.

Extending the caplacizumab treatment period for those patients at risk for relapse (i.e. with underlying disease activity based on ADAMTS13 activity) will maintain the protective effects of caplacizumab until the underlying disease is adequately treated and resolved.

Conversely, precautionary treatment with caplacizumab will reduce the risk of an acute episode of TTP.

7.5.9 Study Results: Organ Damage Markers

The characteristic microvascular occlusions in TTP patients can lead to organ ischaemia throughout the body including brain, heart and, to a lesser extent, kidneys.

Acute myocardial infarction (AMI) has been reported as an early complication of TTP based both on clinical diagnosis of AMI (Patschan et al. 2006 Nephrology, dialysis, transplantation 21: p. 1549-54) and autopsy findings (Hosier et at Archives of pathology & laboratory medicine, 2003. 127(7): p. 834-9). Based on high serum lactate dehydrogenase (LDH) and troponin I (TnI) elevations it was demonstrated that patients with clinically suspected TTP are at high risk to develop AMI. Raised troponin T levels were linked with mortality and acute morbidity. Subjects that died had higher troponin T levels, while there were no deaths in the group of normal troponin T levels. Histology confirmed widespread myocardial microvascular thrombosis in the subjects that died (Hughes et al. 2009 J. Thromb. Haemost. 7: p. 529-536). These results suggest that more rapidly reducing further microvascular cardiac ischemia, e.g. measured by troponin, of the presenting TTP episode could be expected to have a benefit on clinical outcome, e.g. reduces the risk on organ damage, such as brain, heart and kidneys. Other retrospective reports found similar results on acute and long-term cardiac involvement in TTP patients including myocardial infarctions (Wahla et al. 2008 Eur. J. Haem. 81: p. 311-6) and other cardiac events like infarctions, arrhythmias, cardiogenic shock and sudden cardiac death (Hawkins et al. 2008 Transfusion 48: p. 382-92).

In a retrospective study, high levels of LDH at presentation were linked with a worse long term outcome (mortality), reflective of a severe multiple organ involvement (Benhamou, et al. 2012 Haematologica 97: p. 1181-6). Hence, a fast normalization of LDH as marker for hemolysis and ischemic organ damage may also be beneficial for long term clinical outcome, and reduces the risk on organ damage.

Since ischaemic damage may result in both acute complications as well as in poorer longer term outcomes, an analysis was performed on specific and clinically relevant organ damage biomarkers of LDH, troponin T or I and creatinine. It was considered that cardiac troponin (I or T) is a specific marker for myocardial damage, creatinine is a biomarker for renal function, and LDH is a marker of haemolysis and even predominantly a marker of organ damage in this disease. In TTP patients, high baseline levels or a slower normalisation in some of these biomarkers have been linked with worse clinical outcomes (e.g. mortality, refractory disease).

The data suggest that more rapidly curtailing microvascular tissue ischemia as measured by organ damage biomarkers is expected to have a benefit on clinical outcome, e.g. a reduced risk on organ damage. However, it should be noted that the organ damage marker results are to some extent confounded by the dilutive effect of daily plasma exchange (both in the patient and placebo group).

(i) Lactate Dehydrogenase

LDH is an important marker of non-specific tissue ischemia. Proportions were calculated based on the number of subjects in the ITT Population. The number and proportion of subjects in the ITT Population with values for LDH≤2× ULN was summarized by planned treatment for the first 5 study days. A summary of results is provided in Table 9. The mean LDH/ULN ratio by study day is provided in Table 10.

On Day 1, 11 subjects (30.6%) in the ALX-0081 treatment group and 9 subjects (23.1%) in the placebo group had LDH values ≤2×ULN. The proportion of subjects remained higher in the ALX-0081 treatment group compared with the placebo group on Days 2 (28 subjects [77.8%] and 20 subjects [51.3%], respectively) and 3 (33 subjects [91.7%] and 29 subjects [74.4%], respectively). On Days 4 and 5, the proportion of subjects with values for LDH≤2×ULN was similar in both groups.

Mean ratios of LDH/ULN were comparable between the ALX 0081 and placebo treatment groups on Day 1 (3.93 and 3.98, respectively) and higher in the placebo group at all other time points included.

TABLE 9

Number and Proportion of Subjects in with Lactate Dehydrogenase Values ≤2× the Upper Limit of Normal by Study Day (Intent-To-Treat Population)

| Analysis Relative Day | Placebo N = 36 n (%) | ALX 0081 N = 39 n (%) |
|---|---|---|
| 1 | 11 (30.6) | 9 (23.1) |
| 2 | 28 (77.8) | 20 (51.3) |
| 3 | 33 (91.7) | 29 (74.4) |
| 4 | 34 (94.4) | 34 (87.2) |
| 5 | 34 (94.4) | 34 (87.2) |

N = number of subjects in the population of interest;
n = number of subjects with LDH ≤2× the ULN;
ULN = upper limit of the normal range

TABLE 10

Mean Lactate Dehydrogenase/Upper Limit of Normal Ratio by Study Day (Intent-To-Treat Population)

| Analysis Day | Relative | ALX 0081 N = 36 | Placebo N = 39 |
|---|---|---|---|
| 1 | n | 34 | 35 |
|   | Mean | 3.93 | 3.98 |
| 2 | n | 35 | 36 |
|   | Mean | 1.70 | 2.03 |
| 3 | n | 35 | 36 |
|   | Mean | 1.05 | 1.44 |
| 4 | n | 35 | 36 |
|   | Mean | 0.90 | 1.25 |
| 5 | n | 35 | 36 |
|   | Mean | 0.88 | 1.14 |

N = number of subjects in the population of interest;
n = number of subjects with available data A Kaplan-Meier analysis was conducted to compare the time to normalization of LDH values according to the planned treatment. Time to LDH normalization curves are provided in FIG. 2.

From the Kaplan-Meier analysis a more rapid return to normal levels of LDH is suggested for subjects receiving ALX 0081 as compared to subjects receiving placebo.

(ii) Troponin

A Kaplan-Meier analysis was conducted to compare the time to normalization of Troponin T or Troponin I values according to the planned treatment. As noted above, both TnT and TnI are relevant biomarkers of cardiac cell damage. Time to Troponin T or I normalization curves are provided in FIG. 3.

From the Kaplan-Meier analysis a more rapid return to normal levels of Troponin T or I is suggested for subjects receiving ALX 0081 as compared to subjects receiving placebo.

(iii) Creatinine

Also in this case a Kaplan-Meier analysis was conducted to compare the time to normalization of creatinine values according to the planned treatment. Time to creatinine normalization curves are provided in FIG. 4.

For creatinine a more rapid return to normal levels for subjects receiving ALX 0081 as compared to subjects receiving placebo is suggested by the Kaplan-Meier analysis.

(iv) Discussion

Given the pathophysiology of acquired TTP whereby ULvWF strings consume platelets in the formation of microthrombi, it was reasoned that the recovery of platelet counts is an indirect measure of prevention of further microthrombi formation. The morbidity and the acute mortality associated with acquired TTP is a result of these microthrombi.

Indeed, this reasoning is supported by the organ damage markers. In particular, the results indicate that the organ damage markers troponin I and T, LDH and creatinine return faster to normal levels in subjects receiving ALX 0081 than in subjects receiving placebo.

Hence, the results suggest that a faster normalization rate of these organ damage markers is linked to a better clinical outcome, i.e. a reduced risk of and less organ damage due to organ ischemia caused by microthrombi.

7.5.10 Dose Selection Rationale

The pharmacology of caplacizumab is two-fold. Caplacizumab affects the functionality of vWF, leading to inability of vWF to bind to platelets. It also affects the disposition of vWF, leading to transient reductions of total vWF:Ag levels during treatment.

A PK/PD model was used to evaluate the expected exposure and corresponding effect on total, free and complexed vWF levels for different dosing scenarios in a virtual TTP patient population, through simulations. A virtual population of TTP patients (n=500), with characteristics based on the population from the TITAN study, was created by sampling the truncated distributions of body weights (mean 81.9 kg±22.6 SD, range 47.5-150 kg) and model-estimated baseline vWF in the TTP population of the TITAN trial as well as gender distribution (M:F 40:60).

Simulated scenarios included an initial 8 days daily PE procedure with a concomitant s.c. daily administration of caplacizumab 1 h after the termination of each PE at doses of 2.5, 5, 10, 20 mg (period 1). Subsequently, caplacizumab was assumed to be administered at the same dose levels/regimen for additional 30 days in absence of any other PE procedure (period 2).

The % change of the free vWF from baseline increases with the dose, but less than dose-proportional. A large inter-individual variability, mainly related to the large variability of target expression (vWF) at study entry, is predicted at all the dose levels. The two lower doses (2.5 and 5 mg once daily) lead to a sub-optimal target inhibition, whereas a higher daily dose of caplacizumab than the one tested in the TITAN study (20 mg) does not substantially benefit the overall simulated TTP population. FIG. 5 shows the model-predicted % decrease from baseline of free vWF:Ag levels at the end of period 2 as a function of the dose level, including patients treated with placebo.

The simulated plasma profiles of the drug, free, complex and total vWF levels for a 10 mg once daily dose are illustrated in FIG. 6.

Next to change in levels of the free vWF as marker for target neutralization, the change in levels of total vWF as marker for bleeding risk was evaluated. A threshold of 0.4 IU/mL (or 16 nM) was used, linked to the highest vWF levels observed in von Willebrand's disease type I. It is considered that at these levels of vWF, sufficient levels of FVIII remain available. Panel D shows that total vWF levels for the proposed dose of 10 mg once daily would remain above this threshold considered for risk of bleeding events.

Based on the previous in vitro study results and model-predicted levels of biomarkers for efficacy (free vWF) and safety (total vWF), the dosing regimen used herein (5-40 mg, preferably 10 mg daily) is considered as adequate for reaching the desired suppression of the platelet-binding capacity of (UL)vWF in TTP patients, while bleeding events are minimal and at least controllable.

7.6 Conclusion

There is a large inter-individual variability of target expression (vWF) at study entry. Nevertheless, the doses used lead to an optimal target inhibition, substantially benefitting the overall treated TTP population.

Hence, ALX 0081 represents a novel approach to the treatment of TTP and provides a significant benefit in terms of efficacy, safety and quality of life for patients with TTP.

Proof of concept of Caplacizumab was demonstrated with statistically significant and clinically meaningful reduction of time to confirmed platelet response. The median days to confirmed platelet response was 3 days for Caplacizumab vs. 4.9 days for Placebo. The HR (Placebo over Caplacizumab) of 2.2 with 95% CI (1.28, 3.78), p=0.013.

There was a reduction in the number of exacerbations to 3 in the Caplacizumab arm from 11 in the Placebo arm. This underscores the protective effect of caplacizumab treatment.

There were no deaths in the Caplacizumab arm compared to 2 deaths in the Placebo arm.

The AEs and SAEs are consistent with serious, potentially life-threatening condition. Nearly twice as many bleeding events in Caplacizumab arm (66 events) vs. Placebo arm (35 events), although only 5 SAEs in 2 subjects for Caplacizumab arm vs. 2 SAEs in 2 subjects for Placebo arm.

Overall, the benefit risk assessment for patients with acquired TTP is very positive.

Through its inhibition of ULvWF-mediated platelet aggregation and resulting antithrombotic effect the polypeptides of the invention, such as ALX 0081, permits a more rapid control of acute bouts of UP when used in combination with PE and transfusion. This clearly reduces the risk of organ ischaemia. The more rapid normalisation of the platelet count also reduces the risk of haemorrhagic complications. Its use also results in improved outcomes in poorly responsive patients, including those with secondary TTP where mortality from the disease remains high.

In addition, the polypeptides of the invention, such as ALX 0081 are of value in the prevention of relapses after recovery from an acute episode.

TABLE A-1

Examples of polypeptides comprising ISVDs and CDRs against vWF

| Name | SEQ ID NO | Sequence |
|---|---|---|
| 12A02H1-3a-12A02H1 (ALX 0081) | 1 | EVQLVESGGGLVQPGGSLRLSCAASGRITSYNPMGWFRQAPGKGRELVA AISRTGGSTYYPDSVEGRFTISRDNAKRMVYLQMNSLRAEDTAVYYCAAA GVRAEDGRVRTLPSEYTFWGQGTQVTVSSAAAEVQLVESGGGLVQPGG SLRLSCAASGRTESYNPMGWFRQAPGKGRELVAAISRTGGSTYYPDSVEG RFTISRDNAKRMVYLQMNSLRAEDTAVYYCAAAGVRAEDGRVRTLPSEYT FWGQGTQVTVSS |
| 12A02-3a-12A02 | 2 | QVKLEESGGGLVQAGGALRLSCAASGRTFSYNPMGWERCIAPGKERDLV AAISRTGGSMPDSVEGRFTISRDNAKRMVYLQMNNLKPEDTAVYYCAA AGVRAEDGRVRTLPSEYTFWGQGTQVTVSSAAAEVQLVESGGGLVQAG GALRLSCAASGRTFSYNPMGWFRQAPGKERDLVAAISRTGGSTYYPDSVE GRFTISRDNAKRMVYLQMNNLKPEDTAVYYCAAAGVRAEDGRVRTLPSE YTFWGQGTQVTVSS |
| 12A02-GS9-12A02 | 3 | QVKLEESGGGLVQAGGALRLSCAASGRTFSYNPMGWFRQAPGKERDLV ANSRTGGSTYYPDSVEGRFTISRDNAKRMVYLQMNNLKPEDTAVYYCAA AGVRAEDGRVRTLPSEYTFWGQGTQWVSSGGGGSGGGGSEVQLVESGG GLVQAGGALRLSCAASGRTFSYNPMGWERQAPGKERDLVAAISRTGGST YYPDSVEGRFTISRDNAKRMVYLQMNNLKPEDTAVYYCAAAGVRAEDGR VRTLPSEYTFWGQGTQVTVSS |
| 12A02-GS30-12A02 | 4 | QVKLEESGGGLVQAGGALRLSCAASGRTFSYNPGFRQAPGKERDLV AAISRTGGSTYYPDSVEGRFTISRDNAKRMVYLQMNNLKPEDTAVYYCAA AGVRAEDGRVRTLPSEYTFWGQGTQVTVSSGGGGSGGGGSGGGGSGG GGSGGGGSGGGGSEVQLVESGGGLVQAGGALRLSCAASGRTFSYNPMG WERQAPGKERDLVAAISRTGGSTYYPDSVEGRFTISRDNAKRMVYLQMN NLKPEGTAVYYCAAAGVRAEDGRVRTLPSEYTFWGQGTQVTVSS |
| 12A05-3a-12A05 | 5 | AVQLVESGGGLVQPGGSLRLSCLASGRIFSIGAMGMYRQAPGKQRELVA TITSGGSTNYADPVKGRFTISRDGPKNTVYLQMNSLKPEDTAVYYCYANLK QGSYGYRENDYWGQGTQVTVSSAAAEVQLVESGGGLVQPGGSLRLSCLA SGRIFSIGAMGMYRQAPGKQRELVATITSGGSTNYADPVKGRFTISRDGP KNTVYLQMNSLKPEDTAVYYCYANLKQGSYGYRFNDYWGQGTQVTVSS |
| 12A05-GS9-12A05 | 6 | AVQLVESGGGLVQPGGSLRLSCLASGRIFSIGAMGMYRQAPGKCIRELVA TITSGGSTNYADPVKGRFTISRDGPKNIVYLQMNSIKPEDTAVYYCYANLK QGSYGYRFNDYWGQGTQVTVSSGGGGSGGGSEVQLVESGGGLVQPGG SLRLSCLASGRIFSIGAMGMYRQAPGKQRELVATITSGGSTNYADPVKGRF TISRDGPKNTVYLQMNSLKPEDTAVYYCYANLKQGSYGYRFNDYWGQGT QVTVSS |
| 12A05-GS30-12A05 | 7 | AVQLVESGGGLVQPGGSLRLSCLASGRIFSIGAMGMYRQAPGKQRELVA TITSGGSTNYADPVKGRFTISRDGPKNIVYLQMNSLKPEDTAVYYCYANLK QGSYGYRFNDYWGQGTQVTVSSGGGGSGGGGSGGGGSGGGGSGGGG SGGGGSEVQLVESGGGLVQPGGSLRLSCLASGRIFSIGAMGMYRQAPGK QRELVATITSGGSTNYADPVKGRFTISRDGPKNIVYLQMNSLKPEDTAVYY CYANLKQGSYGYRFNDYWGQGTQVTVSS |
| 2B06-3a-12606 | 8 | QVQLVESGGGLVQAGGALRLSCAASGRTFSYNPGFRQAPGKERDVV AAISRTGGSTYYARSVEGRFTISRDNAKRMVYLQMNALKPEDTAVYYCAA AGVRAEDGRVRTLPSEYNFWGQGTQVTVSSAAAEVQLVESGGGLVQAG GALRLSCAASGRTFSYNPMGWFRQAPGKERDVVAAISRTGGSTYYARSV EGRFTISRDNAKRMVYLQMNALKPEDTAVYYCAAAGVRAEDGRVRTLPS EYNFWGQGTQVTVSS |
| 12B06-GS9-12B06 | 9 | QVQLVESGGGLVQAGGALRLSCAASGRTFSYNPGFRQAPGKERDVV AAISRTGGSTYYARSVEGRFTISRDNAKRMVYLQMNALKPEDTAVYYCAA AGVRAEDGRVRTLPSEYNFWGQGTQTVSSGGGGSGGGSEVQLVESGG GLVQAGGALRLSCAASGRTFSYNPMGWFRQAPGKERDVVAAISRTGGST YYARSVEGRFTISRDNAKRMVYLQMNALKPEDTAVYYCAAAGVRAEDGR VRTLPSEYNFWGQGTQVTVSS |
| 12B06-GS30-12B06 | 10 | QVQLVESGGGLVQAGGALRLSCAASGRTFSYNPGFRQAPGKERDVV AAISRIGGSTYYARSVEGRFTISRDNAKRMVYLQMNALKPEDTAVYYCAA AGVRAEDGRVRTLPSEYNFWGQGTQVTVSSGGGGSGGGGSGGGGSGG GGSGGGGSGGGGSEVQLVESGGGLVQAGGALRLSCAASGRTFSYNPMG WFRQAPGKERDVVAAISRTGGSTYYARSVEGRFTISRDNAKRMVYLQMN ALKPEDTAVYYCAAAGVRAEDGRVRTLPSEYNFWGQGTQVTVSS |
| 12A02H4-3a-12A02H4 | 11 | EVQLVESGGGLVQPGGSLRLSCAASGRTFSYNPMGWFRQAPGKGRELVA AISRTGGSTYYPDSVEGRFTISRDNAKRSVYLQMNSLRAEDTAVYYCAAAG VRAEDGRVRTLPSEYTFWGQGTQVTVSSAAAEVQLVESGGGLVQPGGSL RLSCAASGRTFSYNPMGWFRQAPGKGRELVAAISRTGGSTYYPDSVEGRF TISRDNAKRSVYLQMNSLRAEDTAVYYCAAAGVRAEDGRVRTLPSEYTFW GQGTQVTVSS |

TABLE A-1-continued

Examples of polypeptides comprising ISVDs and CDRs against vWF

| Name | SEQ ID NO | Sequence |
|---|---|---|
| 12B06H2-3a-12B06H2 | 12 | EVQLVESGGGLVQPGGSLRLSCAASGRTFSYNPMGWFRQAPGKGREVV AAISRTGGSTYYARSVEGRFTISRDNAKRMVYLQMNSLRAEDTAVYYCAA AGVRAEDGRVRTLPSEYNFWGQGTQVTVSSAAAEVQLVESGGGLVQPG GSLRLSCAASGRTFSYNPMGWFRQAPGKGREVVAAISRTGGSTYYARSVE GRFTISRDNAKRMVYLQMNSLRAEDTAVYYCAAAGVRAEDGRVRTLPSE YNFWGQGTQVTVSS |
| 12A02H1-GS9-12A02H1 | 13 | EVQLVESGGGLVQPGGSLRLSCAASGRIFSYNPMGWFRQAPGKGRELVA AISRTGGSTYYPDSVEGRFTISRDNAKRMVYLQMNSLRAEDTAVYYCAAA GVRAEDGRVRTLPSEYTFWGQGTQVTVSSGGGGSGGGGSEVQLVESGGG LVQPGGSLRLSCAASGRTFSYNPMGWFRQAPGKGRELVAAISRTGGSTYY PDSVEGRFTISRDNAKRMVYLQMNSLRAEDTAVYYCAAAGVRAEDGRVR TLPSEYTFWGQGTQVTVSS |
| 12A02H4-GS9-12A02H4 | 14 | EVQLVESGGGLVQPGGSLRLSCAASGRTFSYNPMGWFRQAPGKGRELVA AISRTGGSTYYPDSVEGRFTISRDNAKRSVYLQMNSLRAEDTAVYYCAAAG VRAEDGRVRTLPSEYTFWGQGTQVTVSSGGGGSGGGGSEVQLVESGGGL VQPGGSLRLSCAASGRITSYNPMGWFRQAPGKGRELVAAISRTGGSTYY PDSVEGRFTISRDNAKRSVYLQMNSLRAEDTAVYYCAAAGVRAEDGRVRT LPSEYTFWGQGTQVTVSS |
| 12B06H2-GS9-12B06H2 | 15 | EVQLVESGGGLVQPGGSLRLSCAASGRTFSYNPGWFRQAPGKGREVV AAISRTGGSTYYARSVEGRFTISRDNAKRMVYLQMNSLRAEDTAVYYCAA AGVRAEDGRVRTLPSEYNFWGQGTQNTVSSGGGGSGGGGSEVQLVESGG GLVQPGGSLRLSCAASGRTFSYNPMGWFRQAPGKGREVVAAISRTGGST YYARSVEGRFTISRDNAKRMVYLQMNSLRAEDTAVYYCAAAGVRAEDGR VRTLPSEYNFWGQGTQVTVSS |
| 12A02H1-GS30-12A02H1 | 16 | EVQLVESGGGLVQPGGSLRLSCAASGRITSYNPMGWFRQAPGKGRELVA AISRTGGSTYYPDSVEGRFTISRDNAKRMVYLQMNSLRAEDTAVYYCAAA GVRAEDGRVRTLPSEYTEVVGQGTQVTVSSGGGGSGGGGSGGGGSGGG GSGGGGSGGGGSEVQLVESGGGLVQPGGSLRLSCAASGRTFSYNPMGW FRQAPGKGRELVAAISRTGGSTYYPDSVEGRFTISRDNAKRMVYLQMNSL RAEDTAVYYCAAAGVRAEDGRVRTLPSEYTFWGQGTQVTVSS |
| 12A02H4-GS30-12A02H4 | 17 | EVQLVESGGGLVQPGGSLRLSCAASGRTFSYNPMGWERQAPGKGRELVA AISRTGGSTYYPDSVEGRETISRDNAKRSVYLQMNSLRAEDTAVYYCAAAG VRAEDGRVRTLPSEYTFWGQGTQVTVSSGGGGSGGGGSGGGGSGGGG SGGGGSGGGGSEVTLVESGGGLVQPGGSLRLSCAASGRTFSYNPMGWF RQAPGKGRELVAAISRTGGSTYYPDSVEGRFTISRDNAKRSVYLTMNSIRA EDTAVYYCAAAGVRAEDGRVRTLPSEYTFWGQGTQVTVSS |
| 12B06H2-GS30-12B06H2 | 18 | EVQLVESGGGLVQPGGSLRLSCAASGRIFSYNPMGWERQAPGKGREVV AAISRIGGSTYYARSVEGRETISRDNAKRMVYLQMNSLRAEDTAVYYCAA AGVRAEDGRVRTLPSEYNFWGQGTQVTVSSGGGGSGGGGSGGGGSGG GGSGGGGSGGGGSEVQLVESGGGLVQPGGSLRLSCAASGRTFSYNPMG WERQAPGKGREVVAAISRTGGSTYYARSVEGRFTISRDNAKRMVYLQMN SLRAEDTAVYYCAAAGVRAEDGRVRTLPSEYNFWGQGTQVTVSS |
| 12A02H1 | 19 | EVQLVESGGGLVQPGGSLRLSCAASGRTFSYNPMGWFRQAPGKGRELVA AISRTGGSTYYPDSVEGRFTISRDNAKRMVYLQMNSLRAEDTAVYYCAAA GVRAEDGRVRTLPSEYTFWGQGTQVTVSS |
| 12A02H1 CDR1 | 21 | YNPMG |
| 12A02H1 CDR2 | 22 | AISRTGGSTYYPDSVEG |
| 12A02H1 CDR3 | 23 | AGVRAEDGRVRTLPSEYTF |

TABLE A-2

| Name | SEQ ID NO | Sequence |
|---|---|---|
| Human vWF | 20 | MIPARFAGVLLALAULPGTLCAEGTRGRSSTARCSLFGSDFVNTFDGSMYSFAGYCSYLLAG GCQKRSFSIIGDFQNGKRVSLSVYLGEFFDIHLFVNGTVTQGDQRVSMPYASKGLYLETEAG YYKLSGEAYGFVARIDGSGNFQVLLSDRYFNKTCGLCGNFNIFAEDDFMTQEGTLTSDPYDF ANSWALSSGEQWCERASPPSSSCNISSGEMQKGLWEQCQLLKSTSVFARCHPLVDPEPFV ALCEKTLCECAGGLECACPALLEYARTCAQEGMVLYGWTDHSACSPVCPAGMEYRQCVSP |

TABLE A-2-continued

| Name | SEQ ID NO | Sequence |
|---|---|---|
| | | CARTCQSLHINEMCQERCVDGCSCPEGQLLDEGLCVESTECPCVHSGKRYPPGTSLSRDCN<br>TCICRNSQWICSNEECPGECLVTGQSHFKSFDNRYFTFSGICQYLLARDCQDHSFSIVIETVQ<br>CADDRDAVCTRSVTVRLPGLHNSLVKLKHGAGVAMDGQDIQLPLLKGDLRIQHTVTASVRL<br>SYGEDLQMDWDGRGRLLVKLSPVYAGKTCGLCGNYNGNQGDDFLTPSGLAEPRVEDFGN<br>AWKLHGDCQDLQKQHSDPCALNPRMTRFSEEACAVLTSPTFEACHRAVSPLPYLRNCRYD<br>VCSCSDGRECLCGALASYAAACAGRGVRVAWREPGRCELNCPKGQVYLQCGTPCNLTCRS<br>LSYPDEECNEACLEGCFCPPGLYMDERGDCVPKAQCPCYYDGEIFQPEDIFSDHHTMCYCE<br>DGFMHCTMSGVPGSLLPDAVLSSPLSHRSKRSLSCRPPMVKLVCPADNLRAEGLECTKTCQ<br>NYDLECMSMGCVSGCLCPPGMVRHENRCVALERCPCFHQGKEYAPGETWIGCNTCVCR<br>DRKVVNCTDHVCDATCSTIGMAHYLTFDGLKYLFPGECQYVLVQDYCGSNPGTFRILVGNK<br>GCSHPSVKCKKRVTILVEGGEIELFDGEVNVKRPMKDETHFEVVESGRYIILLLGKALSVVWD<br>RHLSISVVLKQTYQEKVCGLCGNFDGIQNNDLTSSNLCWEEDPVIDEGNSWKVSSQCADTRK<br>VPLDSSPATCHNNIMKQTMVDSSCRILTSDVFQDCNKLVDPEPYLDVCIYDTCSCESIGDCA<br>CFCDTIAAYAHVCAQHGKVVTWRTATLCPQSCEERNLRENGYECEWRYNSCAPACQVIC<br>QHPEPLACPVQCVEGCHAHCPPGKILDELLQTCVDPEDCPVCEVAGRRFASGKKVTLNPSD<br>PEHCQICHCDVVNLICEACQEPGGLVVPPTDAPVSPTTLYVEDISEPPLHDFYCSRLLDLVFLL<br>DGSSRLSEAEFEVLKAFVVDMMERLRISQKWVRVAVVEYHDGSHAYIGLKDRKRPSELRRIA<br>SQVKYAGSQVASTSEVLKYTLFQIFSKIDRPEASRIALLLMASQEPQRMSRNFVRYVQGLKKK<br>KVIVIPVGIGPHANLKQIRLIEKQAPENKAFVLSSVDELEQQRDEIVSYLCDLAPEAPPPTLPP<br>HMAQVTVPGLRNSMVLDVAFVLEGSDKIGEADFNRSKEFMEEVIQRMDVGQDSIHVTV<br>QYSYMVTVEYPFSEAQSKGDILQVRVREIRYQGGNRTNTGLALRYLSDHSFLVSQGDREQA<br>PNLVYMVTGNPASDEIKRLPGDIQVVPIGVGPNANVQELERIGWPNAPILIQDFETLPREAP<br>DLVLQRCCSGEGLQIPTLSPAPDCSQPLDVILLLDGSSSFPASYFDEMKSFAKAFISKANIGPR<br>LTQVSVLQYGSITTIDVPWNVVPEKAHLLSLVDVMQREGGPSCKDALGFAVRYLTSEMHG<br>ARPGASKAVVILVTDVSVDSVDAAADAARSNRVTVFPIGIGDRYDAAQLRILAGPAGDSNV<br>VKLQRIEDLPTMVTLGNSFLHKLCSGFVRICMDEDGNEKRPGDVWTLPDCICHTVTCQPDG<br>QTLLKSHRVNCDRGLRPSCPNSQSPVKVEETCGCRWTCPCVCTGSSTRHIVTFDGQNFKLT<br>GSCSYVLFQNKEQDLEVILHNGACSPGARQGCMKSIEVKHSALSVELHSDMEVTVNGRLVS<br>VPYVGGNMEVNVYGAIMHEVRFNHLGHIFTFTPQNNEFQLQLSPKTFASKTYGLCGICDEN<br>GANNMLRDGTVITIDWKILVQEWTVQRPGQTCQPILEEQCLVPDSSHCQVIALPLFAECH<br>KVLAPATFYAICQQDSCHQEQVCVEIASYAHLCRTNGVCDWRTPDFCAMSCPPSLVYNH<br>CEHGCPRHCDGNVSSCGDHPSEGCFCPPDKVMLEGSCVPEEACTQCIGEDGVQHQFLEA<br>WVPDHCIPCQICTCLSGRKVNCTTQPCPTAKAPTCGLCEVARLRQNADQCCPEYECVCDPV<br>SCDLPPVPHCERGLQPTLTNPGECRPNFTCACRKEECKRVSPPSCPPHRLPTLRKTQCCDEY<br>ECACNCVNSTVSCPLGYLASTATNDCGCTTFTCLPDKVCVHRSTIYPVGQFWEEGCDVCTC<br>TDMEDAVMGLRVAQCSQKPCEDSCRSGFTYVLHEGECCGRCLPSACEVVTGSPRGDSQSS<br>WKSVGSQWASPENPCLINECVRVKEEVFIQQRNVSCPQLEVPVCPSGFQLSCKTSACCPSC<br>RCERMEACMLNGTVIGPGKTVMIDVCTTCRCMVQVGVISGFKLECRKTTCNPCPLGYKEE<br>NNTGECCGRCLPTACTIQLRGGQIMTLKRDETLQDGCDTHFCKVNERGEYFWEKRVTGCP<br>PFDEHKCLAEGGKIMKIPGTCCDTCEEPECNDITARLQYVKVGSCKSEVEVDIHYCQGKCAS<br>KAMYSIDINDVQDQCSCCSPTRTEPMQVALHCTNGSVVYHEVLNAMECKCSPRKCSK |

The invention claimed is:

1. A method for reducing the risk of an acute episode of thrombotic thrombocytopenic purpura (TTP) in a human subject in need thereof, comprising: (a) selecting a human subject with reduced ADAMTS13 activity; and (b) administering to said human subject a dose of 5-40 mg of a polypeptide comprising the amino acid sequence of SEQ ID NO: 1; wherein step (a) comprises:

(i) measuring the ADAMTS13 activity of said human subject;

(ii) comparing said ADAMTS13 activity with a reference ADAMTS13 activity; and (iii) identifying said human subject as having reduced ADAMTS13 activity if said ADAMTS13 activity is lower than 10% of said reference ADAMTS13 activity.

2. The method according to claim 1, wherein said risk of an acute episode of TTP, is reduced by factor of at least 1.2.

3. The method according to claim 2, wherein the risk is reduced by a factor of 1.5 or more.

4. The method according to claim 1, further comprising: (c) measuring a platelet number of said human subject; and (d) if said platelet number is lower than 150,000/μl, then repeating step (b).

5. A method for mitigating a symptom of and/or postponing the development of thrombotic thrombocytopenic purpura (TTP) in a human subject in need thereof, such that the condition of the human subject is improved or maintained, comprising measuring the ADAMTS13 activity of said human subject and administering a polypeptide comprising the amino acid sequence of SEQ ID NO: 1 until the ADAMTS13 activity is at least 10% of an ADAMTS13 reference activity.

6. A method for mitigating a symptom of and/or postponing the development of thrombotic thrombocytopenic purpura (TTP) in a human subject in need thereof, such that the condition of the human subject is improved or maintained, comprising: (a) selecting a human subject having reduced ADAMTS13 activity; and (b) administering to said human subject a dose of 5-40 mg of a polypeptide comprising the amino acid sequence of SEQ ID NO: 1; wherein step (a) comprises:

(i) performing a Plasma Exchange (PE);

(ii) administering to said human subject a dose of 5-40 mg of a polypeptide comprising the amino acid sequence of SEQ ID NO: 1;

(iii) measuring the ADAMTS13 activity of said human subject;

(iv) comparing said ADAMTS13 activity with a reference ADAMTS13 activity; and (v) identifying said human subject as having reduced ADAMTS13 if said ADAMTS13 activity is lower than 10% of said reference ADAMTS13 activity.

7. The method according to claim 6, wherein step (b) comprises administering to said human subject a dose of 5-40 mg of a polypeptide comprising the amino acid sequence of SEQ ID NO: 1 once or twice per day, for at most 7 days, and optionally preforming a PE one or twice per day.

8. The method according to claim 1, wherein said dose is 10-12 mg.

9. The method according to claim 8, wherein said dose is 11 mg.

10. The method according to claim 6, wherein said dose in step (a)(ii) and/or step (b) is 10-12 mg.

11. The method according to claim 10, wherein said dose in step (a)(ii) and/or step (b) is 11 mg.

12. The method according to claim 5, wherein the polypeptide is administered at a dose of 5-40 mg.

13. The method according to claim 12, wherein said dose is 10-12 mg.

14. The method according to claim 1, wherein said polypeptide consists of the amino acid sequence of SEQ ID NO: 1.

15. The method according to claim 5, wherein said polypeptide consists of the amino acid sequence of SEQ ID NO: 1.

16. The method according to claim 6, wherein said polypeptide consists of the amino acid sequence of SEQ ID NO: 1.

17. A method for mitigating a symptom of and/or postponing the development of thrombotic thrombocytopenic purpura (TTP) in a human subject in need thereof, comprising: (a) selecting a human subject with reduced ADAMTS13 activity; and (b) administering to said human subject a dose of 5-40 mg of a polypeptide comprising the amino acid sequence of SEQ ID NO: 1; wherein step (a) comprises:

(i) measuring the ADAMTS13 activity of said human subject;

(ii) comparing said ADAMTS13 activity with a reference ADAMTS13 activity; and (iii) identifying said human subject as having reduced ADAMTS13 activity if said ADAMTS13 activity is lower than 10% of said reference ADAMTS13 activity.

18. The method according to claim 17, wherein said dose is 10-12 mg.

19. The method according to claim 18, wherein said dose is 11 mg.

20. The method according to claim 17, wherein said polypeptide consists of the amino acid sequence of SEQ ID NO: 1.

* * * * *

SEQUENCE LISTING

<160> NUMBER OF SEQ ID NOS: 23

<210> SEQ ID NO 1
<211> LENGTH: 259
<212> TYPE: PRT
<213> ORGANISM: Artificial Sequence
<220> FEATURE:
<223> OTHER INFORMATION: 12A02H1-3a-12A02H1

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
```

```
                85                  90                  95
Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

Ala Ala Ala Glu Val Gln Leu Val Glu Ser Gly Gly Gly Leu Val Gln
            130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
                180                 185                 190

Asp Ser Val Glu Gly Arg Phe Thr Ile Ser Arg Asp Asn Ala Lys Arg
            195                 200                 205

Met Val Tyr Leu Gln Met Asn Ser Leu Arg Ala Glu Asp Thr Ala Val
            210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser

<210> SEQ ID NO 2
<211> LENGTH: 259
<212> TYPE: PRT
<213> ORGANISM: Artificial Sequence
<220> FEATURE:
<223> OTHER INFORMATION: 12A02-3a-12A02

<400> SEQUENCE: 2

Gln Val Lys Leu Glu Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Leu Val
        35                  40                  45

Ala Ala Ile Ser Arg Thr Gly Gly Ser Thr Tyr Tyr Pro Asp Ser Val
50                  55                  60

Glu Gly Arg Phe Thr Ile Ser Arg Asp Asn Ala Lys Arg Met Val Tyr
65                  70                  75                  80

Leu Gln Met Asn Asn Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

Ala Ala Ala Glu Val Gln Leu Val Glu Ser Gly Gly Gly Leu Val Gln
            130                 135                 140

Ala Gly Gly Ala Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Glu Arg
                165                 170                 175

Asp Leu Val Ala Ala Ile Ser Arg Thr Gly Gly Ser Thr Tyr Tyr Pro
            180                 185                 190
```

```
Asp Ser Val Glu Gly Arg Phe Thr Ile Ser Arg Asp Asn Ala Lys Arg
            195                 200                 205

Met Val Tyr Leu Gln Met Asn Asn Leu Lys Pro Glu Asp Thr Ala Val
    210                 215                 220

Tyr Tyr Cys Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser

<210> SEQ ID NO 3
<211> LENGTH: 265
<212> TYPE: PRT
<213> ORGANISM: Artificial Sequence
<220> FEATURE:
<223> OTHER INFORMATION: 12A02-GS9-12A02

<400> SEQUENCE: 3

Gln Val Lys Leu Glu Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Asn Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Gly Gly Gly Gly Ser Gly Gly Gly Ser Glu Val Gln Leu Val Glu Ser
    130                 135                 140

Gly Gly Gly Leu Val Gln Ala Gly Gly Ala Leu Arg Leu Ser Cys Ala
145                 150                 155                 160

Ala Ser Gly Arg Thr Phe Ser Tyr Asn Pro Met Gly Trp Phe Arg Gln
                165                 170                 175

Ala Pro Gly Lys Glu Arg Asp Leu Val Ala Ala Ile Ser Arg Thr Gly
            180                 185                 190

Gly Ser Thr Tyr Tyr Pro Asp Ser Val Glu Gly Arg Phe Thr Ile Ser
        195                 200                 205

Arg Asp Asn Ala Lys Arg Met Val Tyr Leu Gln Met Asn Asn Leu Lys
    210                 215                 220

Pro Glu Asp Thr Ala Val Tyr Tyr Cys Ala Ala Ala Gly Val Arg Ala
225                 230                 235                 240

Glu Asp Gly Arg Val Arg Thr Leu Pro Ser Glu Tyr Thr Phe Trp Gly
                245                 250                 255

Gln Gly Thr Gln Val Thr Val Ser Ser
            260                 265

<210> SEQ ID NO 4
<211> LENGTH: 286
```

```
<212> TYPE: PRT
<213> ORGANISM: Artificial Sequence
<220> FEATURE:
<223> OTHER INFORMATION: 12A02-GS30--12A02

<400> SEQUENCE: 4

Gln Val Lys Leu Glu Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Asn Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Gly Gly Gly Gly Ser Gly Gly Gly Ser Gly Gly Gly Gly Ser Gly
    130                 135                 140

Gly Gly Gly Ser Gly Gly Gly Ser Gly Gly Gly Ser Glu Val
145                 150                 155                 160

Gln Leu Val Glu Ser Gly Gly Gly Leu Val Gln Ala Gly Gly Ala Leu
                165                 170                 175

Arg Leu Ser Cys Ala Ala Ser Gly Arg Thr Phe Ser Tyr Asn Pro Met
            180                 185                 190

Gly Trp Phe Arg Gln Ala Pro Gly Lys Glu Arg Asp Leu Val Ala Ala
        195                 200                 205

Ile Ser Arg Thr Gly Gly Ser Thr Tyr Tyr Pro Asp Ser Val Glu Gly
    210                 215                 220

Arg Phe Thr Ile Ser Arg Asp Asn Ala Lys Arg Met Val Tyr Leu Gln
225                 230                 235                 240

Met Asn Asn Leu Lys Pro Glu Asp Thr Ala Val Tyr Tyr Cys Ala Ala
                245                 250                 255

Ala Gly Val Arg Ala Glu Asp Gly Arg Val Arg Thr Leu Pro Ser Glu
            260                 265                 270

Tyr Thr Phe Trp Gly Gln Gly Thr Gln Val Thr Val Ser Ser
        275                 280                 285

<210> SEQ ID NO 5
<211> LENGTH: 247
<212> TYPE: PRT
<213> ORGANISM: Artificial Sequence
<220> FEATURE:
<223> OTHER INFORMATION: 12A05-3a-12A05

<400> SEQUENCE: 5

Ala Val Gln Leu Val Glu Ser Gly Gly Gly Leu Val Gln Pro Gly Gly
1               5                   10                  15

Ser Leu Arg Leu Ser Cys Leu Ala Ser Gly Arg Ile Phe Ser Ile Gly
            20                  25                  30

Ala Met Gly Met Tyr Arg Gln Ala Pro Gly Lys Gln Arg Glu Leu Val
        35                  40                  45
```

Ala Thr Ile Thr Ser Gly Gly Ser Thr Asn Tyr Ala Asp Pro Val Lys
            50                  55                  60

Gly Arg Phe Thr Ile Ser Arg Asp Gly Pro Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asn Leu Lys Gln Gly Ser Tyr Gly Tyr Arg Phe Asn Asp Tyr Trp
            100                 105                 110

Gly Gln Gly Thr Gln Val Thr Val Ser Ser Ala Ala Ala Glu Val Gln
            115                 120                 125

Leu Val Glu Ser Gly Gly Leu Val Gln Pro Gly Gly Ser Leu Arg
130                 135                 140

Leu Ser Cys Leu Ala Ser Gly Arg Ile Phe Ser Ile Gly Ala Met Gly
145                 150                 155                 160

Met Tyr Arg Gln Ala Pro Gly Lys Gln Arg Glu Leu Val Ala Thr Ile
                165                 170                 175

Thr Ser Gly Gly Ser Thr Asn Tyr Ala Asp Pro Val Lys Gly Arg Phe
            180                 185                 190

Thr Ile Ser Arg Asp Gly Pro Lys Asn Thr Val Tyr Leu Gln Met Asn
            195                 200                 205

Ser Leu Lys Pro Glu Asp Thr Ala Val Tyr Tyr Cys Tyr Ala Asn Leu
210                 215                 220

Lys Gln Gly Ser Tyr Gly Tyr Arg Phe Asn Asp Tyr Trp Gly Gln Gly
225                 230                 235                 240

Thr Gln Val Thr Val Ser Ser
                245

<210> SEQ ID NO 6
<211> LENGTH: 253
<212> TYPE: PRT
<213> ORGANISM: Artificial Sequence
<220> FEATURE:
<223> OTHER INFORMATION: 12A05-GS9-12A05

<400> SEQUENCE: 6

Ala Val Gln Leu Val Glu Ser Gly Gly Gly Leu Val Gln Pro Gly Gly
1               5                   10                  15

Ser Leu Arg Leu Ser Cys Leu Ala Ser Gly Arg Ile Phe Ser Ile Gly
            20                  25                  30

Ala Met Gly Met Tyr Arg Gln Ala Pro Gly Lys Gln Arg Glu Leu Val
            35                  40                  45

Ala Thr Ile Thr Ser Gly Gly Ser Thr Asn Tyr Ala Asp Pro Val Lys
            50                  55                  60

Gly Arg Phe Thr Ile Ser Arg Asp Gly Pro Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asn Leu Lys Gln Gly Ser Tyr Gly Tyr Arg Phe Asn Asp Tyr Trp
            100                 105                 110

Gly Gln Gly Thr Gln Val Thr Val Ser Ser Gly Gly Gly Gly Ser Gly
            115                 120                 125

Gly Gly Ser Glu Val Gln Leu Val Glu Ser Gly Gly Gly Leu Val Gln
            130                 135                 140

Pro Gly Gly Ser Leu Arg Leu Ser Cys Leu Ala Ser Gly Arg Ile Phe
145                 150                 155                 160

Ser Ile Gly Ala Met Gly Met Tyr Arg Gln Ala Pro Gly Lys Gln Arg
            165                 170                 175

Glu Leu Val Ala Thr Ile Thr Ser Gly Gly Ser Thr Asn Tyr Ala Asp
            180                 185                 190

Pro Val Lys Gly Arg Phe Thr Ile Ser Arg Asp Gly Pro Lys Asn Thr
            195                 200                 205

Val Tyr Leu Gln Met Asn Ser Leu Lys Pro Glu Asp Thr Ala Val Tyr
            210                 215                 220

Tyr Cys Tyr Ala Asn Leu Lys Gln Gly Ser Tyr Gly Tyr Arg Phe Asn
225                 230                 235                 240

Asp Tyr Trp Gly Gln Gly Thr Gln Val Thr Val Ser Ser
            245                 250

<210> SEQ ID NO 7
<211> LENGTH: 274
<212> TYPE: PRT
<213> ORGANISM: Artificial Sequence
<220> FEATURE:
<223> OTHER INFORMATION: 12A05-GS30-12A05

<400> SEQUENCE: 7

Ala Val Gln Leu Val Glu Ser Gly Gly Gly Leu Val Gln Pro Gly Gly
1               5                   10                  15

Ser Leu Arg Leu Ser Cys Leu Ala Ser Gly Arg Ile Phe Ser Ile Gly
            20                  25                  30

Ala Met Gly Met Tyr Arg Gln Ala Pro Gly Lys Gln Arg Glu Leu Val
            35                  40                  45

Ala Thr Ile Thr Ser Gly Gly Ser Thr Asn Tyr Ala Asp Pro Val Lys
        50                  55                  60

Gly Arg Phe Thr Ile Ser Arg Asp Gly Pro Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asn Leu Lys Gln Gly Ser Tyr Gly Tyr Arg Phe Asn Asp Tyr Trp
            100                 105                 110

Gly Gln Gly Thr Gln Val Thr Val Ser Ser Gly Gly Gly Gly Ser Gly
            115                 120                 125

Gly Gly Gly Ser Gly Gly Gly Ser Gly Gly Gly Gly Ser Gly Gly Gly
        130                 135                 140

Gly Gly Ser Gly Gly Gly Gly Ser Glu Val Gln Leu Val Glu Ser Gly
145                 150                 155                 160

Gly Gly Leu Val Gln Pro Gly Gly Ser Leu Arg Leu Ser Cys Leu Ala
                165                 170                 175

Ser Gly Arg Ile Phe Ser Ile Gly Ala Met Gly Met Tyr Arg Gln Ala
            180                 185                 190

Pro Gly Lys Gln Arg Glu Leu Val Ala Thr Ile Thr Ser Gly Gly Ser
            195                 200                 205

Thr Asn Tyr Ala Asp Pro Val Lys Gly Arg Phe Thr Ile Ser Arg Asp
        210                 215                 220

Gly Pro Lys Asn Thr Val Tyr Leu Gln Met Asn Ser Leu Lys Pro Glu
225                 230                 235                 240

Asp Thr Ala Val Tyr Tyr Cys Tyr Ala Asn Leu Lys Gln Gly Ser Tyr
                245                 250                 255

Gly Tyr Arg Phe Asn Asp Tyr Trp Gly Gln Gly Thr Gln Val Thr Val
            260                 265                 270

-continued

Ser Ser

<210> SEQ ID NO 8
<211> LENGTH: 259
<212> TYPE: PRT
<213> ORGANISM: Artificial Sequence
<220> FEATURE:
<223> OTHER INFORMATION: 12B06-3a-12B06

<400> SEQUENCE: 8

Gln Val Gln Leu Val Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Val Val
        35                  40                  45

Ala Ala Ile Ser Arg Thr Gly Gly Ser Thr Tyr Tyr Ala Arg Ser Val
    50                  55                  60

Glu Gly Arg Phe Thr Ile Ser Arg Asp Asn Ala Lys Arg Met Val Tyr
65                  70                  75                  80

Leu Gln Met Asn Ala Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Ala Gly Gly Ala Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Glu Arg
                165                 170                 175

Asp Val Val Ala Ala Ile Ser Arg Thr Gly Gly Ser Thr Tyr Tyr Ala
            180                 185                 190

Arg Ser Val Glu Gly Arg Phe Thr Ile Ser Arg Asp Asn Ala Lys Arg
        195                 200                 205

Met Val Tyr Leu Gln Met Asn Ala Leu Lys Pro Glu Asp Thr Ala Val
    210                 215                 220

Tyr Tyr Cys Ala Ala Ala Gly Val Arg Ala Glu Asp Gly Arg Val Arg
225                 230                 235                 240

Thr Leu Pro Ser Glu Tyr Asn Phe Trp Gly Gln Gly Thr Gln Val Thr
                245                 250                 255

Val Ser Ser

<210> SEQ ID NO 9
<211> LENGTH: 265
<212> TYPE: PRT
<213> ORGANISM: Artificial Sequence
<220> FEATURE:
<223> OTHER INFORMATION: 12B06-GS9-12B06

<400> SEQUENCE: 9

Gln Val Gln Leu Val Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

```
Pro Met Gly Trp Phe Arg Gln Ala Pro Gly Lys Glu Arg Asp Val Val
            35                  40                  45

Ala Ala Ile Ser Arg Thr Gly Gly Ser Thr Tyr Tyr Ala Arg Ser Val
 50                  55                  60

Glu Gly Arg Phe Thr Ile Ser Arg Asp Asn Ala Lys Arg Met Val Tyr
 65                  70                  75                  80

Leu Gln Met Asn Ala Leu Lys Pro Glu Asp Thr Ala Val Tyr Tyr Cys
                 85                  90                  95

Ala Ala Ala Gly Val Arg Ala Glu Asp Gly Arg Val Arg Thr Leu Pro
                100                 105                 110

Ser Glu Tyr Asn Phe Trp Gly Gln Gly Thr Gln Val Thr Val Ser Ser
                115                 120                 125

Gly Gly Gly Gly Ser Gly Gly Ser Glu Val Gln Leu Val Glu Ser
        130                 135                 140

Gly Gly Gly Leu Val Gln Ala Gly Gly Ala Leu Arg Leu Ser Cys Ala
145                 150                 155                 160

Ala Ser Gly Arg Thr Phe Ser Tyr Asn Pro Met Gly Trp Phe Arg Gln
                165                 170                 175

Ala Pro Gly Lys Glu Arg Asp Val Val Ala Ala Ile Ser Arg Thr Gly
                180                 185                 190

Gly Ser Thr Tyr Tyr Ala Arg Ser Val Glu Gly Arg Phe Thr Ile Ser
                195                 200                 205

Arg Asp Asn Ala Lys Arg Met Val Tyr Leu Gln Met Asn Ala Leu Lys
        210                 215                 220

Pro Glu Asp Thr Ala Val Tyr Tyr Cys Ala Ala Ala Gly Val Arg Ala
225                 230                 235                 240

Glu Asp Gly Arg Val Arg Thr Leu Pro Ser Glu Tyr Asn Phe Trp Gly
                245                 250                 255

Gln Gly Thr Gln Val Thr Val Ser Ser
                260                 265

<210> SEQ ID NO 10
<211> LENGTH: 286
<212> TYPE: PRT
<213> ORGANISM: Artificial Sequence
<220> FEATURE:
<223> OTHER INFORMATION: 12B06-GS30-12B06

<400> SEQUENCE: 10

Gln Val Gln Leu Val Glu Ser Gly Gly Gly Leu Val Gln Ala Gly Gly
1               5                  10                  15

Ala Leu Arg Leu Ser Cys Ala Ala Ser Gly Arg Thr Phe Ser Tyr Asn
                20                  25                  30

Pro Met Gly Trp Phe Arg Gln Ala Pro Gly Lys Glu Arg Asp Val Val
            35                  40                  45

Ala Ala Ile Ser Arg Thr Gly Gly Ser Thr Tyr Tyr Ala Arg Ser Val
 50                  55                  60

Glu Gly Arg Phe Thr Ile Ser Arg Asp Asn Ala Lys Arg Met Val Tyr
 65                  70                  75                  80

Leu Gln Met Asn Ala Leu Lys Pro Glu Asp Thr Ala Val Tyr Tyr Cys
                 85                  90                  95

Ala Ala Ala Gly Val Arg Ala Glu Asp Gly Arg Val Arg Thr Leu Pro
                100                 105                 110

Ser Glu Tyr Asn Phe Trp Gly Gln Gly Thr Gln Val Thr Val Ser Ser
                115                 120                 125
```

Gly Gly Gly Ser Gly Gly Gly Ser Gly Gly Gly Ser Gly
130                 135                 140

Gly Gly Gly Ser Gly Gly Gly Ser Gly Gly Gly Ser Glu Val
145                 150                 155                 160

Gln Leu Val Glu Ser Gly Gly Gly Leu Val Gln Ala Gly Gly Ala Leu
            165                 170                 175

Arg Leu Ser Cys Ala Ala Ser Gly Arg Thr Phe Ser Tyr Asn Pro Met
            180                 185                 190

Gly Trp Phe Arg Gln Ala Pro Gly Lys Glu Arg Asp Val Val Ala Ala
            195                 200                 205

Ile Ser Arg Thr Gly Gly Ser Thr Tyr Tyr Ala Arg Ser Val Glu Gly
210                 215                 220

Arg Phe Thr Ile Ser Arg Asp Asn Ala Lys Arg Met Val Tyr Leu Gln
225                 230                 235                 240

Met Asn Ala Leu Lys Pro Glu Asp Thr Ala Val Tyr Tyr Cys Ala Ala
            245                 250                 255

Ala Gly Val Arg Ala Glu Asp Gly Arg Val Arg Thr Leu Pro Ser Glu
            260                 265                 270

Tyr Asn Phe Trp Gly Gln Gly Thr Gln Val Thr Val Ser Ser
            275                 280                 285

<210> SEQ ID NO 11
<211> LENGTH: 259
<212> TYPE: PRT
<213> ORGANISM: Artificial Sequence
<220> FEATURE:
<223> OTHER INFORMATION: 12A02H4-3a-12A02H4

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Ser Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Asp Ser Val Glu Gly Arg Phe Thr Ile Ser Arg Asp Asn Ala Lys Arg
        195                 200                 205

```
Ser Val Tyr Leu Gln Met Asn Ser Leu Arg Ala Glu Asp Thr Ala Val
    210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser
```

<210> SEQ ID NO 12
<211> LENGTH: 259
<212> TYPE: PRT
<213> ORGANISM: Artificial Sequence
<220> FEATURE:
<223> OTHER INFORMATION: 12B06H2-3a-12B06H2

<400> SEQUENCE: 12

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Val Val
        35                  40                  45

Ala Ala Ile Ser Arg Thr Gly Gly Ser Thr Tyr Tyr Ala Arg Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Val Val Ala Ala Ile Ser Arg Thr Gly Gly Ser Thr Tyr Tyr Ala
            180                 185                 190

Arg Ser Val Glu Gly Arg Phe Thr Ile Ser Arg Asp Asn Ala Lys Arg
        195                 200                 205

Met Val Tyr Leu Gln Met Asn Ser Leu Arg Ala Glu Asp Thr Ala Val
    210                 215                 220

Tyr Tyr Cys Ala Ala Ala Gly Val Arg Ala Glu Asp Gly Arg Val Arg
225                 230                 235                 240

Thr Leu Pro Ser Glu Tyr Asn Phe Trp Gly Gln Gly Thr Gln Val Thr
                245                 250                 255

Val Ser Ser
```

<210> SEQ ID NO 13
<211> LENGTH: 265
<212> TYPE: PRT
<213> ORGANISM: Artificial Sequence
<220> FEATURE:
<223> OTHER INFORMATION: 12A02H1-GS9-12A02H1

<400> SEQUENCE: 13

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Gly Gly Gly Gly Ser Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Arg Thr Phe Ser Tyr Asn Pro Met Gly Trp Phe Arg Gln
                165                 170                 175

Ala Pro Gly Lys Gly Arg Glu Leu Val Ala Ala Ile Ser Arg Thr Gly
            180                 185                 190

Gly Ser Thr Tyr Tyr Pro Asp Ser Val Glu Gly Arg Phe Thr Ile Ser
        195                 200                 205

Arg Asp Asn Ala Lys Arg Met Val Tyr Leu Gln Met Asn Ser Leu Arg
    210                 215                 220

Ala Glu Asp Thr Ala Val Tyr Tyr Cys Ala Ala Ala Gly Val Arg Ala
225                 230                 235                 240

Glu Asp Gly Arg Val Arg Thr Leu Pro Ser Glu Tyr Thr Phe Trp Gly
                245                 250                 255

Gln Gly Thr Gln Val Thr Val Ser Ser
            260                 265
```

<210> SEQ ID NO 14
<211> LENGTH: 265
<212> TYPE: PRT
<213> ORGANISM: Artificial Sequence
<220> FEATURE:
<223> OTHER INFORMATION: 12A02H4-GS9-12A02H4

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Ser Val Tyr
65                  70                  75                  80

Leu Gln Met Asn Ser Leu Arg Ala Glu Asp Thr Ala Val Tyr Tyr Cys
```

```
            85                  90                  95
Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

Gly Gly Gly Gly Ser Gly Gly Gly Ser Glu Val Gln Leu Val Glu Ser
            130                 135                 140

Gly Gly Gly Leu Val Gln Pro Gly Gly Ser Leu Arg Leu Ser Cys Ala
145                 150                 155                 160

Ala Ser Gly Arg Thr Phe Ser Tyr Asn Pro Met Gly Trp Phe Arg Gln
            165                 170                 175

Ala Pro Gly Lys Gly Arg Glu Leu Val Ala Ala Ile Ser Arg Thr Gly
            180                 185                 190

Gly Ser Thr Tyr Tyr Pro Asp Ser Val Glu Gly Arg Phe Thr Ile Ser
            195                 200                 205

Arg Asp Asn Ala Lys Arg Ser Val Tyr Leu Gln Met Asn Ser Leu Arg
210                 215                 220

Ala Glu Asp Thr Ala Val Tyr Tyr Cys Ala Ala Ala Gly Val Arg Ala
225                 230                 235                 240

Glu Asp Gly Arg Val Arg Thr Leu Pro Ser Glu Tyr Thr Phe Trp Gly
            245                 250                 255

Gln Gly Thr Gln Val Thr Val Ser Ser
            260                 265

<210> SEQ ID NO 15
<211> LENGTH: 265
<212> TYPE: PRT
<213> ORGANISM: Artificial Sequence
<220> FEATURE:
<223> OTHER INFORMATION: 12B06H2-GS9-12B06H2

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Val Val
            35                  40                  45

Ala Ala Ile Ser Arg Thr Gly Gly Ser Thr Tyr Tyr Ala Arg Ser Val
            50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
            85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
            115                 120                 125

Gly Gly Gly Gly Ser Gly Gly Gly Ser Glu Val Gln Leu Val Glu Ser
            130                 135                 140

Gly Gly Gly Leu Val Gln Pro Gly Gly Ser Leu Arg Leu Ser Cys Ala
145                 150                 155                 160

Ala Ser Gly Arg Thr Phe Ser Tyr Asn Pro Met Gly Trp Phe Arg Gln
            165                 170                 175

Ala Pro Gly Lys Gly Arg Glu Val Val Ala Ala Ile Ser Arg Thr Gly
```

```
                180                 185                 190
Gly Ser Thr Tyr Tyr Ala Arg Ser Val Glu Gly Arg Phe Thr Ile Ser
            195                 200                 205

Arg Asp Asn Ala Lys Arg Met Val Tyr Leu Gln Met Asn Ser Leu Arg
        210                 215                 220

Ala Glu Asp Thr Ala Val Tyr Tyr Cys Ala Ala Gly Val Arg Ala
225                 230                 235                 240

Glu Asp Gly Arg Val Arg Thr Leu Pro Ser Glu Tyr Asn Phe Trp Gly
            245                 250                 255

Gln Gly Thr Gln Val Thr Val Ser Ser
        260                 265

<210> SEQ ID NO 16
<211> LENGTH: 286
<212> TYPE: PRT
<213> ORGANISM: Artificial Sequence
<220> FEATURE:
<223> OTHER INFORMATION: 12A02H1-GS30-12A02H1

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Gly Gly Gly Gly Ser Gly Gly Gly Ser Gly Gly Gly Gly Ser Gly
    130                 135                 140

Gly Gly Gly Ser Gly Gly Gly Ser Gly Gly Gly Gly Ser Glu Val
145                 150                 155                 160

Gln Leu Val Glu Ser Gly Gly Gly Leu Val Gln Pro Gly Gly Ser Leu
                165                 170                 175

Arg Leu Ser Cys Ala Ala Ser Gly Arg Thr Phe Ser Tyr Asn Pro Met
            180                 185                 190

Gly Trp Phe Arg Gln Ala Pro Gly Lys Gly Arg Glu Leu Val Ala Ala
        195                 200                 205

Ile Ser Arg Thr Gly Gly Ser Thr Tyr Tyr Pro Asp Ser Val Glu Gly
    210                 215                 220

Arg Phe Thr Ile Ser Arg Asp Asn Ala Lys Arg Met Val Tyr Leu Gln
225                 230                 235                 240

Met Asn Ser Leu Arg Ala Glu Asp Thr Ala Val Tyr Tyr Cys Ala Ala
                245                 250                 255

Ala Gly Val Arg Ala Glu Asp Gly Arg Val Arg Thr Leu Pro Ser Glu
            260                 265                 270

Tyr Thr Phe Trp Gly Gln Gly Thr Gln Val Thr Val Ser Ser
```

<210> SEQ ID NO 17
<211> LENGTH: 286
<212> TYPE: PRT
<213> ORGANISM: Artificial Sequence
<220> FEATURE:
<223> OTHER INFORMATION: 12A02H4-GS30-12A02H4

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Ser Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Gly Gly Gly Gly Ser Gly Gly Gly Ser Gly Gly Gly Gly Ser Gly
    130                 135                 140

Gly Gly Ser Gly Gly Gly Ser Gly Gly Gly Ser Glu Val
145                 150                 155                 160

Gln Leu Val Glu Ser Gly Gly Gly Leu Val Gln Pro Gly Gly Ser Leu
                165                 170                 175

Arg Leu Ser Cys Ala Ala Ser Gly Arg Thr Phe Ser Tyr Asn Pro Met
            180                 185                 190

Gly Trp Phe Arg Gln Ala Pro Gly Lys Gly Arg Glu Leu Val Ala Ala
        195                 200                 205

Ile Ser Arg Thr Gly Gly Ser Thr Tyr Tyr Pro Asp Ser Val Glu Gly
    210                 215                 220

Arg Phe Thr Ile Ser Arg Asp Asn Ala Lys Arg Ser Val Tyr Leu Gln
225                 230                 235                 240

Met Asn Ser Leu Arg Ala Glu Asp Thr Ala Val Tyr Tyr Cys Ala Ala
                245                 250                 255

Ala Gly Val Arg Ala Glu Asp Gly Arg Val Arg Thr Leu Pro Ser Glu
            260                 265                 270

Tyr Thr Phe Trp Gly Gln Gly Thr Gln Val Thr Val Ser Ser
        275                 280                 285

<210> SEQ ID NO 18
<211> LENGTH: 286
<212> TYPE: PRT
<213> ORGANISM: Artificial Sequence
<220> FEATURE:
<223> OTHER INFORMATION: 12B06H2-GS30-12B06H2

<400> SEQUENCE: 18

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Val Val
        35                  40                  45

Ala Ala Ile Ser Arg Thr Gly Gly Ser Thr Tyr Tyr Ala Arg Ser Val
50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
        115                 120                 125

Gly Gly Gly Gly Ser Gly Gly Gly Ser Gly Gly Gly Gly Ser Gly
            130                 135                 140

Gly Gly Gly Ser Gly Gly Gly Ser Gly Gly Gly Ser Glu Val
145                 150                 155                 160

Gln Leu Val Glu Ser Gly Gly Leu Val Gln Pro Gly Gly Ser Leu
                165                 170                 175

Arg Leu Ser Cys Ala Ala Ser Gly Arg Thr Phe Ser Tyr Asn Pro Met
            180                 185                 190

Gly Trp Phe Arg Gln Ala Pro Gly Lys Gly Arg Glu Val Val Ala Ala
        195                 200                 205

Ile Ser Arg Thr Gly Gly Ser Thr Tyr Tyr Ala Arg Ser Val Glu Gly
210                 215                 220

Arg Phe Thr Ile Ser Arg Asp Asn Ala Lys Arg Met Val Tyr Leu Gln
225                 230                 235                 240

Met Asn Ser Leu Arg Ala Glu Asp Thr Ala Val Tyr Tyr Cys Ala Ala
            245                 250                 255

Ala Gly Val Arg Ala Glu Asp Gly Arg Val Arg Thr Leu Pro Ser Glu
            260                 265                 270

Tyr Asn Phe Trp Gly Gln Gly Thr Gln Val Thr Val Ser Ser
        275                 280                 285

<210> SEQ ID NO 19
<211> LENGTH: 128
<212> TYPE: PRT
<213> ORGANISM: Artificial Sequence
<220> FEATURE:
<223> OTHER INFORMATION: 12A02H1

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95
```

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

<210> SEQ ID NO 20
<211> LENGTH: 2804
<212> TYPE: PRT
<213> ORGANISM: Homo sapiens

<400> SEQUENCE: 20

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

```
          Ser Gly Lys Arg Tyr Pro Pro Gly Thr Ser Leu Ser Arg Asp Cys Asn
                  355                 360                 365

Thr Cys Ile Cys Arg Asn Ser Gln Trp Ile Cys Ser Asn Glu Glu Cys
                  370                 375                 380

Pro Gly Glu Cys Leu Val Thr Gly Gln Ser His Phe Lys Ser Phe Asp
          385                 390                 395                 400

Asn Arg Tyr Phe Thr Phe Ser Gly Ile Cys Gln Tyr Leu Leu Ala Arg
                          405                 410                 415

Asp Cys Gln Asp His Ser Phe Ser Ile Val Ile Glu Thr Val Gln Cys
                          420                 425                 430

Ala Asp Asp Arg Asp Ala Val Cys Thr Arg Ser Val Thr Val Arg Leu
                          435                 440                 445

Pro Gly Leu His Asn Ser Leu Val Lys Leu Lys His Gly Ala Gly Val
                          450                 455                 460

Ala Met Asp Gly Gln Asp Ile Gln Leu Pro Leu Leu Lys Gly Asp Leu
          465                 470                 475                 480

Arg Ile Gln His Thr Val Thr Ala Ser Val Arg Leu Ser Tyr Gly Glu
                              485                 490                 495

Asp Leu Gln Met Asp Trp Asp Gly Arg Gly Arg Leu Leu Val Lys Leu
                          500                 505                 510

Ser Pro Val Tyr Ala Gly Lys Thr Cys Gly Leu Cys Gly Asn Tyr Asn
                          515                 520                 525

Gly Asn Gln Gly Asp Asp Phe Leu Thr Pro Ser Gly Leu Ala Glu Pro
                      530                 535                 540

Arg Val Glu Asp Phe Gly Asn Ala Trp Lys Leu His Gly Asp Cys Gln
          545                 550                 555                 560

Asp Leu Gln Lys Gln His Ser Asp Pro Cys Ala Leu Asn Pro Arg Met
                          565                 570                 575

Thr Arg Phe Ser Glu Glu Ala Cys Ala Val Leu Thr Ser Pro Thr Phe
                          580                 585                 590

Glu Ala Cys His Arg Ala Val Ser Pro Leu Pro Tyr Leu Arg Asn Cys
                          595                 600                 605

Arg Tyr Asp Val Cys Ser Cys Ser Asp Gly Arg Glu Cys Leu Cys Gly
                  610                 615                 620

Ala Leu Ala Ser Tyr Ala Ala Ala Cys Ala Gly Arg Gly Val Arg Val
          625                 630                 635                 640

Ala Trp Arg Glu Pro Gly Arg Cys Glu Leu Asn Cys Pro Lys Gly Gln
                          645                 650                 655

Val Tyr Leu Gln Cys Gly Thr Pro Cys Asn Leu Thr Cys Arg Ser Leu
                          660                 665                 670

Ser Tyr Pro Asp Glu Glu Cys Asn Glu Ala Cys Leu Glu Gly Cys Phe
                  675                 680                 685

Cys Pro Pro Gly Leu Tyr Met Asp Glu Arg Gly Asp Cys Val Pro Lys
                  690                 695                 700

Ala Gln Cys Pro Cys Tyr Tyr Asp Gly Glu Ile Phe Gln Pro Glu Asp
          705                 710                 715                 720

Ile Phe Ser Asp His His Thr Met Cys Tyr Cys Glu Asp Gly Phe Met
                              725                 730                 735

His Cys Thr Met Ser Gly Val Pro Gly Ser Leu Leu Pro Asp Ala Val
                      740                 745                 750

Leu Ser Ser Pro Leu Ser His Arg Ser Lys Arg Ser Leu Ser Cys Arg
                      755                 760                 765
```

```
Pro Pro Met Val Lys Leu Val Cys Pro Ala Asp Asn Leu Arg Ala Glu
770                 775                 780
Gly Leu Glu Cys Thr Lys Thr Cys Gln Asn Tyr Asp Leu Glu Cys Met
785                 790                 795                 800
Ser Met Gly Cys Val Ser Gly Cys Leu Cys Pro Pro Gly Met Val Arg
                805                 810                 815
His Glu Asn Arg Cys Val Ala Leu Glu Arg Cys Pro Cys Phe His Gln
                820                 825                 830
Gly Lys Glu Tyr Ala Pro Gly Glu Thr Val Lys Ile Gly Cys Asn Thr
            835                 840                 845
Cys Val Cys Arg Asp Arg Lys Trp Asn Cys Thr Asp His Val Cys Asp
850                 855                 860
Ala Thr Cys Ser Thr Ile Gly Met Ala His Tyr Leu Thr Phe Asp Gly
865                 870                 875                 880
Leu Lys Tyr Leu Phe Pro Gly Glu Cys Gln Tyr Val Leu Val Gln Asp
                885                 890                 895
Tyr Cys Gly Ser Asn Pro Gly Thr Phe Arg Ile Leu Val Gly Asn Lys
            900                 905                 910
Gly Cys Ser His Pro Ser Val Lys Cys Lys Lys Arg Val Thr Ile Leu
        915                 920                 925
Val Glu Gly Gly Glu Ile Glu Leu Phe Asp Gly Glu Val Asn Val Lys
930                 935                 940
Arg Pro Met Lys Asp Glu Thr His Phe Glu Val Val Glu Ser Gly Arg
945                 950                 955                 960
Tyr Ile Ile Leu Leu Leu Gly Lys Ala Leu Ser Val Val Trp Asp Arg
            965                 970                 975
His Leu Ser Ile Ser Val Val Leu Lys Gln Thr Tyr Gln Glu Lys Val
        980                 985                 990
Cys Gly Leu Cys Gly Asn Phe Asp  Gly Ile Gln Asn Asn  Asp Leu Thr
        995                 1000                 1005
Ser Ser  Asn Leu Gln Val  Glu Asp Pro Val Asp  Phe Gly Asn
    1010                 1015                 1020
Ser Trp  Lys Val Ser Ser  Gln Cys Ala Asp Thr Arg  Lys Val Pro
    1025                 1030                 1035
Leu Asp  Ser Ser Pro Ala  Thr  Cys His Asn Asn Ile  Met Lys Gln
    1040                 1045                 1050
Thr Met  Val Asp Ser Ser  Cys  Arg Ile Leu Thr Ser  Asp Val Phe
    1055                 1060                 1065
Gln Asp  Cys Asn Lys Leu Val  Asp Pro Glu Pro  Tyr  Leu Asp Val
    1070                 1075                 1080
Cys Ile  Tyr Asp Thr Cys  Ser  Cys Glu Ser Ile Gly  Asp Cys Ala
    1085                 1090                 1095
Cys Phe  Cys Asp Thr Ile Ala  Ala Tyr Ala His Val  Cys Ala Gln
    1100                 1105                 1110
His Gly  Lys Val Val Thr  Trp  Arg Thr Ala Thr Leu  Cys Pro Gln
    1115                 1120                 1125
Ser Cys  Glu Glu Arg Asn Leu  Arg Glu Asn Gly Tyr  Glu Cys Glu
    1130                 1135                 1140
Trp Arg  Tyr Asn Ser Cys  Ala  Pro Ala Cys Gln Val  Thr Cys Gln
    1145                 1150                 1155
His Pro  Glu Pro Leu Ala  Cys  Pro Val Gln Cys Val  Glu Gly Cys
    1160                 1165                 1170
His Ala  His Cys Pro Pro  Gly  Lys Ile Leu Asp Glu  Leu Leu Gln
```

-continued

```
            1175                1180                1185

Thr Cys Val Asp Pro Glu Asp Cys Pro Val Cys Glu Val Ala Gly
            1190                1195                1200

Arg Arg Phe Ala Ser Gly Lys Lys Val Thr Leu Asn Pro Ser Asp
            1205                1210                1215

Pro Glu His Cys Gln Ile Cys His Cys Asp Val Val Asn Leu Thr
            1220                1225                1230

Cys Glu Ala Cys Gln Glu Pro Gly Gly Leu Val Val Pro Pro Thr
            1235                1240                1245

Asp Ala Pro Val Ser Pro Thr Thr Leu Tyr Val Glu Asp Ile Ser
            1250                1255                1260

Glu Pro Pro Leu His Asp Phe Tyr Cys Ser Arg Leu Leu Asp Leu
            1265                1270                1275

Val Phe Leu Leu Asp Gly Ser Ser Arg Leu Ser Glu Ala Glu Phe
            1280                1285                1290

Glu Val Leu Lys Ala Phe Val Val Asp Met Met Glu Arg Leu Arg
            1295                1300                1305

Ile Ser Gln Lys Trp Val Arg Val Ala Val Val Glu Tyr His Asp
            1310                1315                1320

Gly Ser His Ala Tyr Ile Gly Leu Lys Asp Arg Lys Arg Pro Ser
            1325                1330                1335

Glu Leu Arg Arg Ile Ala Ser Gln Val Lys Tyr Ala Gly Ser Gln
            1340                1345                1350

Val Ala Ser Thr Ser Glu Val Leu Lys Tyr Thr Leu Phe Gln Ile
            1355                1360                1365

Phe Ser Lys Ile Asp Arg Pro Glu Ala Ser Arg Ile Ala Leu Leu
            1370                1375                1380

Leu Met Ala Ser Gln Glu Pro Gln Arg Met Ser Arg Asn Phe Val
            1385                1390                1395

Arg Tyr Val Gln Gly Leu Lys Lys Lys Lys Val Ile Val Ile Pro
            1400                1405                1410

Val Gly Ile Gly Pro His Ala Asn Leu Lys Gln Ile Arg Leu Ile
            1415                1420                1425

Glu Lys Gln Ala Pro Glu Asn Lys Ala Phe Val Leu Ser Ser Val
            1430                1435                1440

Asp Glu Leu Glu Gln Gln Arg Asp Glu Ile Val Ser Tyr Leu Cys
            1445                1450                1455

Asp Leu Ala Pro Glu Ala Pro Pro Pro Thr Leu Pro Pro His Met
            1460                1465                1470

Ala Gln Val Thr Val Gly Pro Gly Leu Arg Asn Ser Met Val Leu
            1475                1480                1485

Asp Val Ala Phe Val Leu Glu Gly Ser Asp Lys Ile Gly Glu Ala
            1490                1495                1500

Asp Phe Asn Arg Ser Lys Glu Phe Met Glu Glu Val Ile Gln Arg
            1505                1510                1515

Met Asp Val Gly Gln Asp Ser Ile His Val Thr Val Leu Gln Tyr
            1520                1525                1530

Ser Tyr Met Val Thr Val Glu Tyr Pro Phe Ser Glu Ala Gln Ser
            1535                1540                1545

Lys Gly Asp Ile Leu Gln Arg Val Arg Glu Ile Arg Tyr Gln Gly
            1550                1555                1560

Gly Asn Arg Thr Asn Thr Gly Leu Ala Leu Arg Tyr Leu Ser Asp
            1565                1570                1575
```

```
His Ser Phe Leu Val Ser Gln Gly Asp Arg Glu Gln Ala Pro Asn
        1580            1585                1590

Leu Val Tyr Met Val Thr Gly Asn Pro Ala Ser Asp Glu Ile Lys
        1595            1600                1605

Arg Leu Pro Gly Asp Ile Gln Val Val Pro Ile Gly Val Gly Pro
        1610            1615                1620

Asn Ala Asn Val Gln Glu Leu Glu Arg Ile Gly Trp Pro Asn Ala
        1625            1630                1635

Pro Ile Leu Ile Gln Asp Phe Glu Thr Leu Pro Arg Glu Ala Pro
        1640            1645                1650

Asp Leu Val Leu Gln Arg Cys Cys Ser Gly Glu Gly Leu Gln Ile
        1655            1660                1665

Pro Thr Leu Ser Pro Ala Pro Asp Cys Ser Gln Pro Leu Asp Val
        1670            1675                1680

Ile Leu Leu Leu Asp Gly Ser Ser Ser Phe Pro Ala Ser Tyr Phe
        1685            1690                1695

Asp Glu Met Lys Ser Phe Ala Lys Ala Phe Ile Ser Lys Ala Asn
        1700            1705                1710

Ile Gly Pro Arg Leu Thr Gln Val Ser Val Leu Gln Tyr Gly Ser
        1715            1720                1725

Ile Thr Thr Ile Asp Val Pro Trp Asn Val Val Pro Glu Lys Ala
        1730            1735                1740

His Leu Leu Ser Leu Val Asp Val Met Gln Arg Glu Gly Gly Pro
        1745            1750                1755

Ser Gln Ile Gly Asp Ala Leu Gly Phe Ala Val Arg Tyr Leu Thr
        1760            1765                1770

Ser Glu Met His Gly Ala Arg Pro Gly Ala Ser Lys Ala Val Val
        1775            1780                1785

Ile Leu Val Thr Asp Val Ser Val Asp Ser Val Asp Ala Ala Ala
        1790            1795                1800

Asp Ala Ala Arg Ser Asn Arg Val Thr Val Phe Pro Ile Gly Ile
        1805            1810                1815

Gly Asp Arg Tyr Asp Ala Ala Gln Leu Arg Ile Leu Ala Gly Pro
        1820            1825                1830

Ala Gly Asp Ser Asn Val Val Lys Leu Gln Arg Ile Glu Asp Leu
        1835            1840                1845

Pro Thr Met Val Thr Leu Gly Asn Ser Phe Leu His Lys Leu Cys
        1850            1855                1860

Ser Gly Phe Val Arg Ile Cys Met Asp Glu Asp Gly Asn Glu Lys
        1865            1870                1875

Arg Pro Gly Asp Val Trp Thr Leu Pro Asp Gln Cys His Thr Val
        1880            1885                1890

Thr Cys Gln Pro Asp Gly Gln Thr Leu Leu Lys Ser His Arg Val
        1895            1900                1905

Asn Cys Asp Arg Gly Leu Arg Pro Ser Cys Pro Asn Ser Gln Ser
        1910            1915                1920

Pro Val Lys Val Glu Glu Thr Cys Gly Cys Arg Trp Thr Cys Pro
        1925            1930                1935

Cys Val Cys Thr Gly Ser Ser Thr Arg His Ile Val Thr Phe Asp
        1940            1945                1950

Gly Gln Asn Phe Lys Leu Thr Gly Ser Cys Ser Tyr Val Leu Phe
        1955            1960                1965
```

```
Gln Asn Lys Glu Gln Asp Leu Glu Val Ile Leu His Asn Gly Ala
    1970                1975                1980

Cys Ser Pro Gly Ala Arg Gln Gly Cys Met Lys Ser Ile Glu Val
    1985                1990                1995

Lys His Ser Ala Leu Ser Val Glu Leu His Ser Asp Met Glu Val
    2000                2005                2010

Thr Val Asn Gly Arg Leu Val Ser Val Pro Tyr Val Gly Gly Asn
    2015                2020                2025

Met Glu Val Asn Val Tyr Gly Ala Ile Met His Glu Val Arg Phe
    2030                2035                2040

Asn His Leu Gly His Ile Phe Thr Phe Thr Pro Gln Asn Asn Glu
    2045                2050                2055

Phe Gln Leu Gln Leu Ser Pro Lys Thr Phe Ala Ser Lys Thr Tyr
    2060                2065                2070

Gly Leu Cys Gly Ile Cys Asp Glu Asn Gly Ala Asn Asp Phe Met
    2075                2080                2085

Leu Arg Asp Gly Thr Val Thr Thr Asp Trp Lys Thr Leu Val Gln
    2090                2095                2100

Glu Trp Thr Val Gln Arg Pro Gly Gln Thr Cys Gln Pro Ile Leu
    2105                2110                2115

Glu Glu Gln Cys Leu Val Pro Asp Ser Ser His Cys Gln Val Leu
    2120                2125                2130

Leu Leu Pro Leu Phe Ala Glu Cys His Lys Val Leu Ala Pro Ala
    2135                2140                2145

Thr Phe Tyr Ala Ile Cys Gln Gln Asp Ser Cys His Gln Glu Gln
    2150                2155                2160

Val Cys Glu Val Ile Ala Ser Tyr Ala His Leu Cys Arg Thr Asn
    2165                2170                2175

Gly Val Cys Val Asp Trp Arg Thr Pro Asp Phe Cys Ala Met Ser
    2180                2185                2190

Cys Pro Pro Ser Leu Val Tyr Asn His Cys Glu His Gly Cys Pro
    2195                2200                2205

Arg His Cys Asp Gly Asn Val Ser Ser Cys Gly Asp His Pro Ser
    2210                2215                2220

Glu Gly Cys Phe Cys Pro Pro Asp Lys Val Met Leu Glu Gly Ser
    2225                2230                2235

Cys Val Pro Glu Glu Ala Cys Thr Gln Cys Ile Gly Glu Asp Gly
    2240                2245                2250

Val Gln His Gln Phe Leu Glu Ala Trp Val Pro Asp His Gln Pro
    2255                2260                2265

Cys Gln Ile Cys Thr Cys Leu Ser Gly Arg Lys Val Asn Cys Thr
    2270                2275                2280

Thr Gln Pro Cys Pro Thr Ala Lys Ala Pro Thr Cys Gly Leu Cys
    2285                2290                2295

Glu Val Ala Arg Leu Arg Gln Asn Ala Asp Gln Cys Cys Pro Glu
    2300                2305                2310

Tyr Glu Cys Val Cys Asp Pro Val Ser Cys Asp Leu Pro Pro Val
    2315                2320                2325

Pro His Cys Glu Arg Gly Leu Gln Pro Thr Leu Thr Asn Pro Gly
    2330                2335                2340

Glu Cys Arg Pro Asn Phe Thr Cys Ala Cys Arg Lys Glu Glu Cys
    2345                2350                2355

Lys Arg Val Ser Pro Pro Ser Cys Pro Pro His Arg Leu Pro Thr
```

```
              2360                2365                2370

Leu Arg Lys Thr Gln Cys Cys Asp Glu Tyr Glu Cys Ala Cys Asn
    2375                2380                2385

Cys Val Asn Ser Thr Val Ser Cys Pro Leu Gly Tyr Leu Ala Ser
    2390                2395                2400

Thr Ala Thr Asn Asp Cys Gly Cys Thr Thr Thr Cys Leu Pro
    2405                2410                2415

Asp Lys Val Cys Val His Arg Ser Thr Ile Tyr Pro Val Gly Gln
    2420                2425                2430

Phe Trp Glu Glu Gly Cys Asp Val Cys Thr Cys Thr Asp Met Glu
    2435                2440                2445

Asp Ala Val Met Gly Leu Arg Val Ala Gln Cys Ser Gln Lys Pro
    2450                2455                2460

Cys Glu Asp Ser Cys Arg Ser Gly Phe Thr Tyr Val Leu His Glu
    2465                2470                2475

Gly Glu Cys Cys Gly Arg Cys Leu Pro Ser Ala Cys Glu Val Val
    2480                2485                2490

Thr Gly Ser Pro Arg Gly Asp Ser Gln Ser Ser Trp Lys Ser Val
    2495                2500                2505

Gly Ser Gln Trp Ala Ser Pro Glu Asn Pro Cys Leu Ile Asn Glu
    2510                2515                2520

Cys Val Arg Val Lys Glu Glu Val Phe Ile Gln Gln Arg Asn Val
    2525                2530                2535

Ser Cys Pro Gln Leu Glu Val Pro Val Cys Pro Ser Gly Phe Gln
    2540                2545                2550

Leu Ser Cys Lys Thr Ser Ala Cys Cys Pro Ser Cys Arg Cys Glu
    2555                2560                2565

Arg Met Glu Ala Cys Met Leu Asn Gly Thr Val Ile Gly Pro Gly
    2570                2575                2580

Lys Thr Val Met Ile Asp Val Cys Thr Thr Cys Arg Cys Met Val
    2585                2590                2595

Gln Val Gly Val Ile Ser Gly Phe Lys Leu Glu Cys Arg Lys Thr
    2600                2605                2610

Thr Cys Asn Pro Cys Pro Leu Gly Tyr Lys Glu Glu Asn Asn Thr
    2615                2620                2625

Gly Glu Cys Cys Gly Arg Cys Leu Pro Thr Ala Cys Thr Ile Gln
    2630                2635                2640

Leu Arg Gly Gly Gln Ile Met Thr Leu Lys Arg Asp Glu Thr Leu
    2645                2650                2655

Gln Asp Gly Cys Asp Thr His Phe Cys Lys Val Asn Glu Arg Gly
    2660                2665                2670

Glu Tyr Phe Trp Glu Lys Arg Val Thr Gly Cys Pro Pro Phe Asp
    2675                2680                2685

Glu His Lys Cys Leu Ala Glu Gly Gly Lys Ile Met Lys Ile Pro
    2690                2695                2700

Gly Thr Cys Cys Asp Thr Cys Glu Glu Pro Glu Cys Asn Asp Ile
    2705                2710                2715

Thr Ala Arg Leu Gln Tyr Val Lys Val Gly Ser Cys Lys Ser Glu
    2720                2725                2730

Val Glu Val Asp Ile His Tyr Cys Gln Gly Lys Cys Ala Ser Lys
    2735                2740                2745

Ala Met Tyr Ser Ile Asp Ile Asn Asp Val Gln Asp Gln Cys Ser
    2750                2755                2760
```

```
Cys Cys Ser Pro Thr Arg Thr Glu Pro Met Gln Val Ala Leu His
    2765            2770            2775

Cys Thr Asn Gly Ser Val Val Tyr His Glu Val Leu Asn Ala Met
    2780            2785            2790

Glu Cys Lys Cys Ser Pro Arg Lys Cys Ser Lys
    2795            2800

<210> SEQ ID NO 21
<211> LENGTH: 5
<212> TYPE: PRT
<213> ORGANISM: Artificial Sequence
<220> FEATURE:
<223> OTHER INFORMATION: 12A02H1 CDR1

<400> SEQUENCE: 21

Tyr Asn Pro Met Gly
1               5

<210> SEQ ID NO 22
<211> LENGTH: 17
<212> TYPE: PRT
<213> ORGANISM: Artificial Sequence
<220> FEATURE:
<223> OTHER INFORMATION: 12A02H1 CDR2

<400> SEQUENCE: 22

Ala Ile Ser Arg Thr Gly Gly Ser Thr Tyr Tyr Pro Asp Ser Val Glu
1               5                   10                  15

Gly

<210> SEQ ID NO 23
<211> LENGTH: 19
<212> TYPE: PRT
<213> ORGANISM: Artificial Sequence
<220> FEATURE:
<223> OTHER INFORMATION: 12A02H1 CDR3

<400> SEQUENCE: 23

Ala Gly Val Arg Ala Glu Asp Gly Arg Val Arg Thr Leu Pro Ser Glu
1               5                   10                  15

Tyr Thr Phe
```